US008518889B2

(12) United States Patent
Kim et al.

(10) Patent No.: US 8,518,889 B2
(45) Date of Patent: Aug. 27, 2013

(54) METHOD OF TREATING CANCER WITH ANTIBODIES AGAINST LONG-FORM LEUKOTRIENE B4 RECEPTOR BLT2

(75) Inventors: Jae-Hong Kim, Gyeonggi-Do (KR); Jung-A Choi, Seoul (KR); Eun-Young Kim, Seoul (KR); Geun-Young Kim, Chungbuk (KR); Chul-Min Kim, Gyeongsangnam-Do (KR); Ji-Min Seo, Seoul (KR); Hyun-Ju Kim, Incheon (KR); Jin-Wook Lee, Daejeon (KR)

(73) Assignee: Korea University Research & Business Foundation, Seoul (KR)

( * ) Notice: Subject to any disclaimer, the term of this patent is extended or adjusted under 35 U.S.C. 154(b) by 0 days.

(21) Appl. No.: 13/316,098

(22) Filed: Dec. 9, 2011

(65) Prior Publication Data

US 2012/0213788 A1 Aug. 23, 2012

Related U.S. Application Data

(66) Continuation-in-part of application No. 12/450,335, filed as application No. PCT/KR2008/001649 on Mar. 24, 2008, now Pat. No. 8,288,357, Substitute for application No. 60/896,504, filed on Mar. 23, 2007.

(60) Provisional application No. 60/896,499, filed on Mar. 23, 2007.

(51) Int. Cl.
| | |
|---|---|
| *A61P 35/00* | (2006.01) |
| *A61K 39/00* | (2006.01) |
| *A61K 39/395* | (2006.01) |
| *C07K 16/28* | (2006.01) |
| *C07K 16/30* | (2006.01) |

(52) U.S. Cl.
USPC .............. 514/19.3; 424/130.1; 424/139.1; 424/142.1; 424/143.1; 424/155.1; 530/389.1

(58) Field of Classification Search
None
See application file for complete search history.

(56) References Cited

U.S. PATENT DOCUMENTS

| 2004/0053962 A1* | 3/2004 | Adrian ............................ 514/311 |
| 2004/0091863 A1* | 5/2004 | Ramakrishnan .................... 435/6 |

FOREIGN PATENT DOCUMENTS

| EP | 1 745 800 A1 | 1/2007 |
| WO | WO99/42484 | * 8/1999 |

OTHER PUBLICATIONS

Ding, XZ, et al., "A novel anti-pancreatic cancer agent, LY293111," Anticancer Drugs, vol. 16, No. 5, pp. 467-473 (Jun. 2005).
Tong, Wei-Gang, et al., "Leukotriene B4 Receptor Antagonist LY293111 Inhibits Proliferation and Induces Apoptosis in Human Pancreatic Cancer Cells," Clin. Cancer Res., vol. 3232, No. 8, pp. 3232-3242 (2002).
Yokomizo, T. et al., "Hydroxyeicosanoids Bind to and Activate the Low Affinity Leukotriene B4 Receptor, BLT2," The Jrl. of Biol. Chem., vol. 276, No. 15, pp. 12454-12459 (Apr. 13, 2001).
Yoo, Min-Hyuk et al., "Role of the BLT2, a leukotriene B4 receptor, in Ras transformation," Oncogene, vol. 23, pp. 9259-9268 (Oct. 18, 2004).
Hennig et al., "Leukotriene B4 receptor 2 (BLT2)—a specific marker and promoter in pancreatic carcinogenesis?", Chirurgisches Forum 2007, vol. 36, VI., Abstract only.
Choi et al., "Reactive oxygen species are generated through a BLT2-linked cascade in Ras-transformed cells", Free Radical Biology & Medicine 44 (2008), pp. 624-634, Available online Oct. 26, 2007.
Biroccio et al., "The future of antisense therapy: combination with anticancer treatments", Oncogene, 2003, vol. 22, pp. 6579-6588.

* cited by examiner

*Primary Examiner* — Elly-Gerald Stoica
(74) *Attorney, Agent, or Firm* — Edwards Wildman Palmer LLP

(57) ABSTRACT

The present invention relates to the use of inhibitors of leukotriene B4 receptor BLT2 for treating human cancers. More particularly, the present invention relates to a pharmaceutical composition for treating human cancers comprising BLT2 inhibitors and a method for treating human cancers using BLT2 inhibitors.

7 Claims, 22 Drawing Sheets

LY255283

MTT assay at 48 hr after LY255283 treatment

Hoechst 33258 staining at 36 hr after LY255283 treatment

DNA fragmentation assay and cell cycle analysis at 48 hr after LY255283 treatment

C (MDA-MB-468 breast cancer cell)

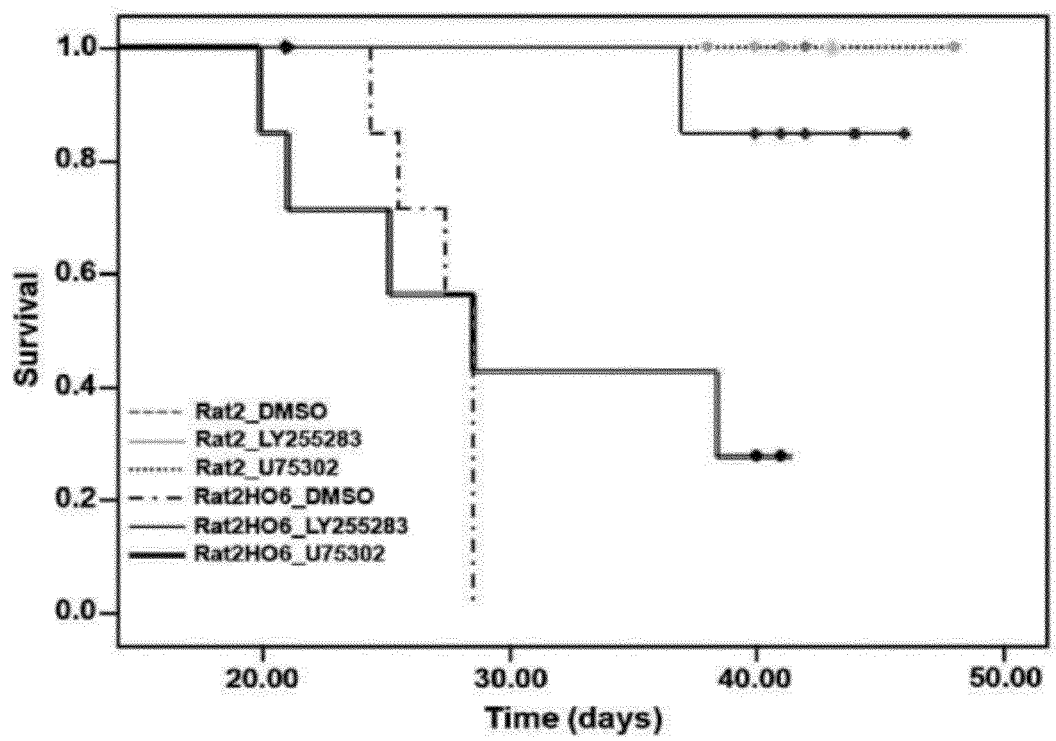

Figure 4b
A 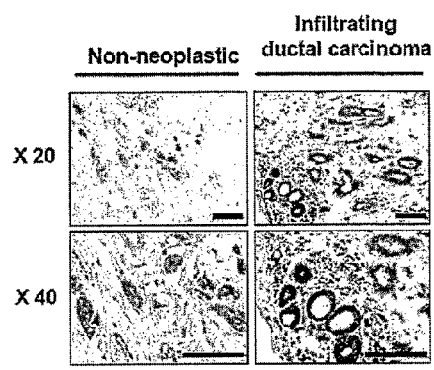 B 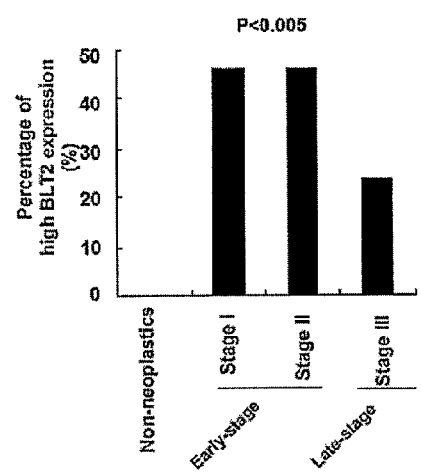
Figure 4c
| cytoplasmic (Total) | Low | Med | High |
|---|---|---|---|
| Stage 0 (4) | 4 (1) | 0 (1) | 0 (2) |
| Stage 1 (13) | 2 (4) | 5 (5) | 6 (5) |
| Stage 2 (39) | 8 (11) | 13 (14) | 18 (15) |
| Stage 3 (18) | 6 (5) | 18 (6) | 4 (7) |
( ) : Expected value Hepatocellular carcinoma (Liver)

Glioblastoma multiforme (Brain)

Infiltrating ductal carcinoma (Breast)

Invasive squamous cell carcinoma (Skin)

Papillary carcinoma (Thyroid)

Normal  Cancer a b

Transient transfection CHO cell
3.0X10⁴ cells/well
LTB$_4$ 300 nM for 3 hrs

Transient transfection CHO cell
3.0X10⁴ cells/well
LTB$_4$ 300 nM for 3 hrs a b a b

| | FACS mean | FACS fold | ELISA BLT2 |
|---|---|---|---|
| control | 175 | 1 | |
| 1 | 193 | 1.1 | 1.2 |
| 2 | 182 | 1.0 | 1.2 |
| 3 | 177 | 1.0 | 1.2 |
| 4 | 172 | 1.0 | 1.3 |
| 5 | 164 | 0.9 | 1.2 |
| 6 | 175 | 1.0 | 1.3 |
| 7 | 172 | 1.0 | 1.2 |
| 8 | 170 | 1.0 | 1.2 |
| 9 | 325 | 1.9 | 0.6 |
| 10 | 331 | 1.9 | 0.5 |
| 11 | 174 | 1.0 | 1.4 |
| 12 | 159 | 0.9 | 1.3 |
| 13 | 170 | 1.0 | 1.2 |
| 14 | 175 | 1.0 | 1.2 |
| 15 | 168 | 1.0 | 1.2 |
| 16 | 180 | 1.0 | 1.2 |
| 17 | 169 | 1.0 | 1.3 |
| 18 | 165 | 0.9 | 1.3 |
| 19 | 312 | 1.8 | 0.9 |
| 20 | 327 | 1.9 | 0.9 |
| 21 | 324 | 1.9 | 0.7 |
| 22 | 321 | 1.8 | 0.8 |

METHOD OF TREATING CANCER WITH ANTIBODIES AGAINST LONG-FORM LEUKOTRIENE B4 RECEPTOR BLT2

CROSS-REFERENCE TO RELATED APPLICATIONS

This application is a continuation-in-part of U.S. application Ser. No. 12/450,335, filed on Sep. 22, 2009, and published as U.S. Patent Application Publication No. 2011/0223152, which is the U.S. national phase, pursuant to 35 U.S.C. §371, of International Application No. PCT/KR2008/001649, filed on Mar. 24, 2008, designating the United States and published in English on Oct. 2, 2008, as International Publication No. WO 2008/117970, which claims the benefit of U.S. Provisional Application Nos. 60/896,499, which was filed on Mar. 23, 2007, and 60/896,504, which was filed on Mar. 23, 2007, the disclosures of which are hereby incorporated in their entireties.

FIELD OF INVENTION

The present invention relates to use of inhibitors of leukotriene B4 receptor BLT2 for treating human cancers. More particularly, the present invention relates to a pharmaceutical composition for treating human cancers comprising BLT2 inhibitors and a method for treating human cancers using BLT2 inhibitors.

BACKGROUND OF THE INVENTION

Leukotrienes are a family of inflammatory lipid mediators that are derived from arachidonic acid (AA) by the action of 5-lipoxygenase (5-LO) and 5-lipoxygenase activating protein (FLAP), which mediate acute and chronic inflammation. Leukotriene $B_4$ ($LTB_4$), the first leukotriene isolated, elicits a variety of inflammatory responses, including leukocyte activation, chemotaxis and degranulation (Samuelsson, 1987; Woo, 2002; Yokimizo, 1997). In addition, overproduction of $LTB_4$ is involved in such inflammation-related ailments as bronchial asthma and rheumatoid arthritis (Chen, 1994; Griffiths, 1995; Turner, 1996). It is known that $LTB_4$ produces its biological effects by binding to its receptors, BLT1 and BLT2 (Yokimizo, 1997; Choi, 2008). Most studies of $LTB_4$ receptors have focused on the high-affinity receptor, BLT1, which is expressed exclusively in inflammatory cells such as leukocytes, and plays a role in inflammatory processes (Yokimizo, 1997). In contrast to BLT1, BLT2 has a low affinity for $LTB_4$ and is expressed in a wide variety of tissues, with highest levels in spleen, leukocytes and ovary (Yokimizo, 1997; Kamohara, 2000). No clear physiological function has yet been identified for BLT2. Recently, BLT2 has been recognized as a downstream component of oncogenic Ras, thereby mediating Ras transformation (Choi, 2008). Consistent with the proposed role of 'LTB_4-BLT2'-cascade as downstream component of Ras signaling, enhanced production of $LTB_4$ has been noted in Rat2-HO6 cells (Yoo, 2004). Interestingly, enhanced production of $LTB_4$ in Rat2-BLT2 cells overexpressing BLT2 has been observed (Yoo, 2004), suggesting the possibility of crosstalk between $LTB_4$ and BLT2 such that each triggers induction of the other. Without being bound to a particular theory, these findings suggest that the transformed phenotype is elicited by an autocrine or paracrine effect of the high level of $LTB_4$ acting via BLT2 to amplify the $LTB_4$-dependent cascade. Consistent with the proposed function of $LTB_4$ and BLT2 as downstream intermediates in H-Ras$^{r12}$ signaling, Rat2-HO6 cells which express oncogenic H-Ras$^{r12}$ cells had increased levels of $cPLA_2$, 5-LO and FLAP, three proteins involved in the synthesis of $LTB_4$ (Yoo, 2004). In that regard, $CPLA_2$ expression is also upregulated in a number of cancer cell lines, and contributes to induction of the transformed phenotypes (Blaine, 2001; Heasley, 1997). Similarly, 5-LO is upregulated in human pancreatic, breast, and prostate cancers (Gupta, 2001; Hennig, 2002; Jiang, 2003; Matsuyama, 2004). In addition, 5-LO and $LTB_4$ receptors are highly expressed in human pancreatic cancers, but not in normal pancreatic duct tissue (Jiang, 2003; Ding, 2005), and the $LTB_4$ receptor BLT1 antagonist LY293111 inhibited the growth of and induced apoptosis of human pancreatic cancer cells (Tong, 2002). However, the role of BLT2 in malignant transformation remains to be elucidated.

Pancreatic cancer has the worst prognosis among solid tumors. It is a near fatal disease and one of the most aggressive human malignancies. The management of patients with pancreatic carcinoma depends on the extent of the disease at diagnosis. Surgical resection followed by adjuvant therapy is the standard care for patients diagnosed with early-stage disease. However, the majority of patients present with advanced-stage disease that precludes surgery. Early pancreatic cancer often does not cause symptoms, and the later symptoms are usually nonspecific and varied. Therefore, pancreatic cancer is often not diagnosed until it is advanced. Prognosis for advanced stage patients is extremely poor and the impact of standard therapy is minimal. At present, no effective treatment exists for pancreatic cancer. New methods of treatment for treating pancreatic cancer and other neoplasias are urgently required.

SUMMARY OF THE INVENTION

It is therefore an object of the present invention to provide use of a BLT2 inhibitor in a medicament for the treatment of human cancer.

Further, another object of the present invention is to provide a pharmaceutical composition for the treatment of human cancer comprising a BLT2 inhibitor as active ingredient.

Further, another object of the present invention is to provide a method for treating a patient with cancer, which comprises administering an effective amount of BLT2 inhibitor to the patient.

Further, another object of the present invention is to provide a method for screening a substance for treating human cancer, which comprises determining whether to reduce the expression or signaling level of BLT2.

Further, another object of the present invention is to provide a kit for detecting human cancer, which comprises a primer or probe for detecting a BLT2 nucleic acid molecule or an antibody foro detecting BLT2 protein.

Thus, the invention provides use of BLT2 inhibitors (e.g., anti-long form BLT2 antibody) for (1) inducing apoptosis of cancer cells, (2) suppressing metastatic potential of cancer cells, (3) blocking angiogenesis of cancer cells. Also, the invention includes (4) a novel strategy for screening BLT2 signaling inhibitors by measuring the cell growth of Rat2-BLT2 stable cells. Lastly, this invention includes (5) the novel observation of BLT2 overexpression in various human cancers, which is an important phenomenon in tumorigenesis. Thus, the invention claims the use of any strategy targeting BLT2 overexpression or over-activation as a tool for developing therapeutic composition against human cancer.

The invention is at least based in part on the finding that BLT2 inhibition leads to enhanced apoptosis in human cancer cells and also to suppressed metastasis of human cancer cells.

Additionally, the combined use of BLT2 antagonist LY255283 with epirubicin or other chemotherapeutic agents caused a synergistic apoptosis of human breast cancer cells. By employing novel BLT2 inhibitors such as BLT2 siRNA or antisense oligonucleotide, many BLT2-signaling inhibitory effects were observed. Thus, this invention provides a novel composition containing anti-long form BLT2 antibody, LY255283, BLT2 antisense oligonucleotide, or other BLT2 signaling inhibitors for preparing therapeutic agents against various human cancers such as bladder cancer, breast cancer, prostate cancer, and pancreatic cancer. The invention is also based on the finding that in most human cancers including bladder cancer, breast cancer, prostate cancer, pancreatic cancer, brain cancer, skin cancer, and liver cancer, BLT2 is highly overexpressed compared to normal tissues which express a minimal amount of BLT2. The finding that overexpression of BLT2 and over-activated signaling of BLT2 play important roles in mediating tumorigenesis serves as the basis for the development of new diagnostic tools and treatments for cancer In one aspect, the invention provides, a method of treating cancer in a patient, the method comprising administering to the patient a therapeutically effective amount of an agent that inhibits the expression or intracellular signaling of long-form BLT2.

In another aspect, the invention provides a method of reducing expression or activity of long-form BLT2 in a cancer cell, the method comprising contacting the cancer cell with an effective amount of an agent that inhibits the expression or intracellular signaling of long-form BLT2.

In still another aspect, the invention provides a monoclonal antibody that inhibits expression or intracellular signaling of long-form BLT2 in a cancer cell. In various embodiments, the monoclonal antibody is used for the treatment of cancer.

In a related aspect, the invention provides a pharmaceutical composition containing a monoclonal antibody that inhibits expression or intracellular signaling of long-form BLT2 in a cancer cell and a pharmaceutical carrier.

In yet another aspect, the invention provides a method for screening an agent for treating cancer, the method involving contacting a cancer cell containing a long-form BLT2 gene or long-form BLT2 protein; and (b) measuring the expression or activity of long-form BLT2 in the cancer cell, wherein a decrease in the expression or activity of long-form BLT2 indicates the agent can be used for treating cancer.

In an additional aspect, the invention provides a kit for the treatment of cancer, the kit comprising an agent that inhibits the expression or intracellular signaling of long-form BLT2.

In various embodiments of any of the aspects delineated herein, the agent selectively reduces the expression or intracellular signaling of long-form BLT2 to the patient while the expression or intracellular signaling of short-form BLT2 is not disrupted.

In various embodiments of any of the aspects delineated herein, the expression or activity of MMP-2 or the phosphorylation of STAT-3 is reduced. In various embodiments of any of the aspects delineated herein, the invasion activity or wound healing migration motility of a cancer cell is reduced. In various embodiments of any of the aspects delineated herein, the cancer cell is an ovarian cancer cell, a bladder cancer cell, or a breast cancer cell. In various embodiments of any of the aspects delineated herein, the method further comprises administering a therapeutically effective amount of an agent that inhibits the expression or activity of Rac.

In various embodiments of any of the aspects delineated herein, the agent is an antibody or fragment thereof that specifically binds long-form BLT-2. In various embodiments, the antibody or fragment thereof specifically binds long-form BLT-2 in the region set forth by amino acids 1-31 of SEQ ID NO: 3. In particular embodiments, the antibody or fragment thereof specifically binds long-form BLT-2 in the region set forth by amino acids 14-27 of SEQ ID NO: 3. In various embodiments of any of the aspects delineated herein, the antibody is a polyclonal or monoclonal antibody.

In various embodiments of any of the aspects delineated herein, the agent is an inhibitory nucleic acid that is complementary to at least a portion of a long-form BLT2 nucleic acid molecule. In various embodiments, the inhibitory nucleic acid is complementary to at least a portion of a long-form BLT2 nucleic acid molecule in the region set forth by nucleotides 1-93 of SEQ ID NO: 2. In various embodiments of any of the aspects delineated herein, the inhibitory nucleic acid is selected from the group consisting of an antisense molecule, and siRNA, and an shRNA.

Other objects and advantage of the present invention will become apparent from the detailed description to follow taken in conjugation with the appended claims and drawings.

BRIEF DESCRIPTION OF THE DRAWINGS

FIG. 2b shows the effect of BLT2 antagonist LY255283 on the survival of mouse injected with Ras-oncogene expressing transformed cells. The LY255283 extended the survival of mouse injected with Ras-cancer cells.

FIG. 4b shows enhanced overexpression of BLT2 in breast cancer clinical specimens. The induction of BLT2 was observed in human breast cancer. FIG. 4c shows enhanced overexpression of BLT2 in breast cancer clinical specimens. The induction of BLT2 was observed in human breast cancer.

FIG. 6a depicts RT-PCR analysis showing that LF-BLT2 and SF-BLT2 transcript levels are similar. FIG. 6b is a graph showing that LF-BLT2 or SF-BLT2 protein expression levels were similar as determined by FACS analysis.

FIG. 7a is a graph showing enhanced chemotactic motility of LF-BLT2 transfected CHO cells in the presence of $LTB_4$ compared to SF-BLT2 transfected CHO cells. FIG. 7b is a graph showing enhanced ROS generation in LF-BLT2 transfected CHO cells in the presence of $LTB_4$ compared to SF-BLT2 transfected CHO cells.

FIG. 8a depicts images of Rat-2 cells transfected with empty vector (left panel), hLFBLT2 construct (middle panel), and hSF-BLT2 construct (right panel). FIG. 8b depicts Western blot analysis of ERK in transfected cells, showing that Rat-2 cells transfected with the hLFBLT2 construct had a significantly enhanced ERK activation in the presence of $LTB_4$ compared to Rat-2 cells transfected with the hSF-BLT2 construct.

FIG. 9a is a graph showing that BLT2 expression enhanced invasiveness in CAOV-3 cells. Cells were transfected with pcDNA3.1-LFBLT2 or pcDNA3.1-SFBLT2 for 24 hr, and the loaded into the upper wells of Matrigel-invasion chambers. After 48 hr, invaded cells were fixed, stained and quantified. Data are expressed as the mean relative to transfected with pcDNA3.1 cells (control) invaded. FIG. 9b depicts RT-PCR analysis showing that BLT2 overexpression induced NOX4 and MMP-2 mRNA levels. CAOV-3 cells were transiently transfected with pcDNA3.1, pcDNA3.1-LFBLT2 or pcDNA3.1-SFBLT2 for 48 hr. The cells were harvested for detection of BLT1, BLT2, NOX4 and MMP-2 transcripts by semiquantitative RT-PCR with specific primers. FIG. 9c depicts Western blot analysis showing that p-STAT3 activated by transient expression of BLT2 in CAOV-3 cells. Cells were transiently transfected with 1 µg of pcDNA3.1-LFBLT2 or pcDNA3.1-SFBLT2, and levels of p-STAT3 (Y705, S727) were detected by Western blot analysis.

FIG. 10a depicts representative results of three independent experiments with similar results. FIG. 10b is a chart showing that out of 22 potential candidates, 6 BLT2 (long-form)-recognizing antibodies were selected by FACS analysis. The 6 BLT2-recognizing antibodies are designated in red.

FIG. 11a is a graph depicting the effect of anti-LF BLT2 antibody on CHO or CHO-BLT2 stable cells exposed to 300 nM $LTB_4$ for 3 hr. $LTB_4$-induced chemotactic motility was determined in the presence of BLT2 IgG Ab (BLT2-LF-26-22; 10 and 20 µg) and negative antibody control (BLT2-LF-13 IgG Ab; 10 and 20 µg). After migration, cells were fixed and stained with hematoxylin/eosin. FIG. 11b is a graph depicting the effect of anti-LF BLT2 antibody on pcDNA3.1 or BLT2 transfected CHO cells exposed to 300 nM $LTB_4$ for 3 hr. $LTB_4$-induced chemotactic motility was determined in the presence of BLT2 IgG Ab (BLT2-LF-26-22; 10 and 20 µg) or control antibody (BLT2-LF-13 IgG Ab; 10 and 20 µg). After migration, cells were fixed and stained with hematoxylin/eosin. FIG. 11c is a graph showing that BLT1-induced chemotactic migration was not affected by anti-BLT2 Ab (BLT2-LF-26-22), control Ab control (BLT2-LF-13, 20 µg), or pcDNA3.1. The BLT1 transfected CHO cells were exposed to 10 nM $LTB_4$ for 3 hr with BLT2 IgG Ab (BLT2-LF-26-22, 20 µg) and negative IgG Ab control (BLT2-LF-13, 20 µg).

DETAILED DESCRIPTION OF THE INVENTION

Figure 1A:
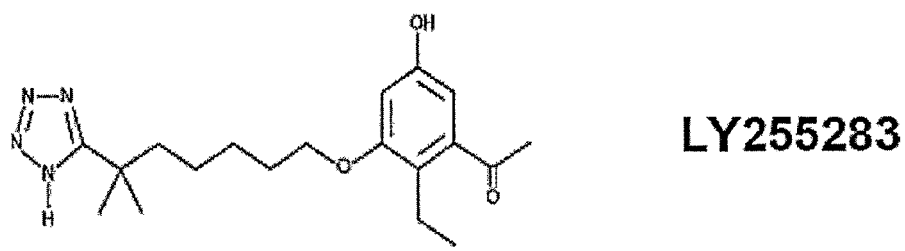
FIG. 1a shows the chemical structure of LY255283, a BLT2 antagonist.

The present invention generally features compositions and methods for treating human cancers involving inhibitors of leukotriene B4 receptor BLT2, including long form BLT2.

According to one aspect of the present invention, there is provided a use of a substance that inhibits the expression or intracellular signaling of BLT2 for the manufacture of a medicament for the treatment of human cancer. In this specification, the phrase "inhibit(s) the expression of BLT2" means to inhibit any step among the transcription, mRNA processing, translation, translocation, and maturation of BLT2, and the phrase "inhibit(s) the intracellular signaling of BLT2" means to inhibit any step among the binding of LTB4 to BLT2, the activation of BLT2 and its intracellular signaling pathway to induce human cancer.

The nucleotide sequence of human BLT2 gene is available at the NCBI (NM_019839) and denoted as SEQ ID NO: 1 in this specification. The BLT2 gene has 2 kinds of CDS form, long form CDS (1618-2787) and short form CDS (1711-2787), the nucleotide sequences of which are denoted as SEQ ID NO: 2 and SEQ ID NO: 4, respectively. The amino acid sequence of the long form BLT2protein is available at the NCBI (NM_019839) and is denoted as SEQ ID NO: 3. The amino acid sequence of the short form BLT2 protein is available at the NCBI (AB029892) and is denoted as SEQ ID NO: 5.

In a preferred embodiment, the substance may be an antibody to BLT2 (e.g., long form BLT2). The antibody to BLT2 inhibits the intracellular signaling of BLT2. The antibody binds to BLT2 competitively with LTB4, so that can inhibit the intracellular signaling of BLT2. The antibody can be produced according to the conventional methods for producing polyclonal or monoclonal antibody by using BLT2 or its fragment as an antigen.

In a preferred embodiment, the substance may be a compound that binds to BLT2 and inhibits the intracellular signaling of BLT2. The compound is also referred to as BLT2 antagonist, which means a compound that antagonizes an action of LTB4 on BLT2. The compound can be screened according to the present screening method from the commercially available chemical database.

In a preferred embodiment, the compound may be LY255283 (1-[5-ethyl-2-hydroxy-4-[[6-methyl-6-(1H-tetrazol-5-yl)heptyl]oxy]phenyl]-ethanone). FIG. 1 a shows a chemical structure of LY255283. LY255283 is a competitive antagonist of the BLT2 receptor. LY255283 have been known to inhibit eosinophil chemotaxis by 80% at a concentration of 10 µM, and inhibits the binding of radiolabeled LTB4 to eosinophil membranes with an IC50 of 260 nM [Ann N Y Acad Sci 629 274-287 (1991)]. Also, LY255283 have been known to be a novel leukotriene B4 receptor antagonist, which limits activation of neutrophils and prevents acute lung injury induced by endotoxin in pigs [Surgery. 1993 August; 114(2): 191-8]. However, the anticancer activity of LY25583 was revealed by the present inventors for the first time.

In a preferred embodiment, the substance may be an antisense or siRNA oligonucleotide that inhibits the expression of BLT2. The antisense or siRNA oligonucleotide has a nucleotide sequence complementary to the nucleotide sequence of BLT2 mRNA as set forth in SEQ ID NO: 2.

The term "antisense oligonucleotide" used herein is intended to refer to nucleic acids, preferably, DNA, RNA or its derivatives, that are complementary to the nucleotide sequences of a target mRNA, characterized in that they binds to the target mRNA and interfere its translation to protein. The antisense oligonucleotide of this invention means DNA or RNA sequences complementary and binding to BLT2 mRNA, that are able to inhibit translation, translocation, maturation or other biological functions of BLT2 mRNA. The antisense nucleic acid is 6-100, preferably, 8-60, more preferably, 10-40 nucleotides in length.

The antisense oligonucleotide may comprise at lease one modification in its base, sugar or backbone for its higher inhibition efficacy (De Mesmaeker et al., Curr Opin Struct Biol., 5(3):343-55 (1995)). The modified nucleic acid backbone comprises phosphorothioate, phosphotriester, methyl phosphonate, short chain alkyl or cycloalkyl intersugar linkages or short chain heteroatomic or heterocyclic intersugar linkages. The antisense oligonucleotide may also contain one or more substituted sugar moieties. The antisense nucleic acid may include one or more modified bases, for example, hypoxanthine, 6-methyladenine, 5-me pyrimidines (particularly, 5-methylcytosine), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine. Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., Proc. Natl. Acad. Sci. USA, 86:6553 (1989)), cholic acid (Manoharan et al. Bioorg. Med. Chem. Let, 4:1053 (1994)), a thioether, e.g., hexyl-5-tritylthiol (Manoharan et al. Ann. N.Y. Acad. ScL, 660:306 (1992); Manoharan et al. Bioorg. Med. Chem. Let, 3: 2765 (1993)), a thiocholesterol (Oberhauser et al., Nucl. Acids Res., 20:533 (1992)), an aliphatic chain, e.g., dodecandiol or undecyl residues (Saison-Behmoaras et al. EMBO J., 10:111 (1991); Kabanov et al. FEBS Lett., 259:327 (1990); Svinarchuk et al. Biochimie, 75:49 (1993), a phospholipid, e.g., di-hexadecyl-rac-glycerol or triethylammonium 1,2-di-O-hexadecyl-rac-glycero-3-H-phosphonate (Manoharan et al. Tetrahedron Lett., 36:3651 (1995); Shea et al. Nucl. Acids Res., 18:3777 (1990)), a polyamine or a polyethylene glycol chain (Manoharan et al. Nucleosides & Nucleotides, 14:969 (1995)), or adamantane acetic acid (Manoharan et al. Tetrahedron Lett, 36: 3651 (1995)). Oligonucleotides comprising lipophilic moieties, and methods for preparing such oligonucleotides are known in the art, for example, U.S. Pat. Nos. 5,138,045, 5,218,105 and 5,459,255. The modifications described above enhance stability against nuclease degradation and increase affinity of the antisense oligonucleotide toward its target mRNA.

The antisense molecule is conventionally synthesized in vitro and then transmitted to cells. In addition, it is intracellular produced by transcription from foreign sequence. In vitro synthesis involves RNA polymerase I. In vivo transcription for preparing antisense RNA uses vector having origin of recognition region (MCS) in opposite orientation. The antisense RNA preferably comprises a translation stop codon for inhibiting translation to peptide.

According to a preferred embodiment, the antisense oligonucleotide may have the nucleotide sequence of SEQ ID NO: 6, which is complementary to the target region (1738-1752) of SEQ ID NO: 2. According to a preferred embodiment, the siRNA oligonucleotide may have a sense sequence of SEQ ID NO: 7 and an antisense sequence of SEQ ID NO: 8, which is complementary to the target region (1705-1724) of SEQ ID NO: 2.

The term "siRNA" used herein refers to a nucleic acid molecule mediating RNA interference or gene silencing (see WO 00/44895, WO 01/36646, WO 99/32619, WO 01/29058, WO 99/07409 and WO 00/44914). The siRNA to inhibit expression of a target gene provides effective gene knockdown method or gene therapy method. It was been first in plants, insects, *Drosophila melanogaster* and parasites and recently has been used for mammalian cell researches. The siRNA molecule of this invention may consist of a sense RNA strand (having sequence corresponding to BLT2 mRNA) and an antisense RNA strand (having sequence complementary to BLT2 mRNA) and form a duplex structure. Alternatively, the siRNA molecule of this invention may have a single strand structure comprising self-complementary sense and antisense strands.

The siRNA of this invention is not restricted to a RNA duplex of which two strands are completely paired and may comprise non-paired portion such as mismatched portion with non-complementary bases and bulge with no opposite bases. The overall length of the siRNA is 10-100 nucleotides, preferably, 15-80 nucleotides, and more preferably, 20-70 nucleotides. The siRNA may comprise either blunt or cohesive end so long as it enables to silent the BLT2 expression due to RNAi effect. The cohesive end may be prepared in 3'-end overhanging structure or 5'-end overhanging structure.

The siRNA may be constructed by inserting a short nucleotide sequence (e.g., about 5-15 nt) between self-complementary sense and antisense strands. The siRNA expressed forms a hairpin structure by intramolecular hybridization, resulting in the formation of stem-and-loop structure. The stem-and-loop structure is processed in vitro or in vivo to generate active siRNA molecule mediating RNAi.

In a preferred embodiment, the substance may be a compound that inhibits the upstream or downstream signaling pathway of BLT2. In certain embodiments, a compound of the invention can prevent, inhibit, or disrupt, or reduce by at least 10%, 25%, 50%, 75%, or 100% the activity of a BLT2 pathway by binding to BLT, e.g., long-form BLT2. An anti-neoplasia therapeutic, such as antibody against long-form BLT2, may be administered in combination with any other standard anti-neoplasia therapy or conventional chemotherapeutic agent, such as an alkylating agent; such methods are known to the skilled artisan and described in Remington's Pharmaceutical Sciences by E. W. Martin. If desired, agents of the invention are administered in combination with any conventional anti-neoplastic therapy, including but not limited to, surgery, radiation therapy, or chemotherapy. Conventional chemotherapeutic agents include, but are not limited to, alemtuzumab, altretamine, aminoglutethimide, amsacrine, anastrozole, azacitidine, bleomycin, bicalutamide, busulfan, capecitabine, carboplatin, carmustine, celecoxib, chlorambucil, 2-chlorodeoxyadenosine, cisplatin, colchicine, cyclophosphamide, cytarabine, cytoxan, dacarbazine, dactinomycin, daunorubicin, docetaxel, doxorubicin, epirubicin, estramustine phosphate, etodolac, etoposide, exemestane, floxuridine, fludarabine, 5-fluorouracil, flutamide, formestane, gemcitabine, gentuzumab, goserelin, hexamethylmelamine, hydroxyurea, hypericin, ifosfamide, imatinib, interferon, irinotecan, letrozole, leuporelin, lomustine, mechlorethamine, melphalen, mercaptopurine, 6-mercaptopurine, methotrexate, mitomycin, mitotane, mitoxantrone, nilutamide, nocodazole, paclitaxel, pentostatin, procarbazine, raltitrexed, rituximab, rofecoxib, streptozocin, tamoxifen, temozolomide, teniposide, 6-thioguanine, topotecan, toremofine, trastuzumab, vinblastine, vincristine, vindesine, and vinorelbine.

In the preferred embodiment, the human cancer may be any cancer that is induced by over-expression of BLT2 protein or oncogenic Ras. The present inventors have found that BLT2 protein was over-expressed in bladder cancer, breast cancer, prostate cancer, liver cancer, brain cancer, skin cancer, etc. and that the inhibition of the over-expression of BLT2 can suppress cancer transformation. Therefore, any anti-cancer therapy strategy based on the inhibition of BLT2 overexpression is claimed as the present invention.

In the preferred embodiment, the human cancer may be selected from the group consisting of bladder, prostate, pancreatic, and breast cancer. The present inventors demonstrated that the present BLT2 inhibitors have the anti-cancer effects against bladder, prostate, pancreatic, and breast cancer in Examples.

In the preferred embodiment, the treatment of human cancer may be accomplished by inducing the apoptosis of cancer cells, inhibiting the metastasis of cancer cells, or inhibiting the angiogenesis of tumor.

Therefore, any use of BLT2 inhibitors as apoptosis-inducing therapeutic composition against human cancer cells is claimed in the present invention. The present inventors have found that BLT2 antagonist LY255283 has an apoptosis-inducing activity against bladder, prostate, pancreatic, and breast cancer in Examples. Further, any use of BLT2 inhibitors as cancer cell metastasis-inhibiting therapeutic composition is claimed in the present invention. The present inventors have found that treatment of BLT2-signaling inhibitor LY255283 or BLT2 anti-sense oligonucleotide remarkably suppresses the metastasis of cancer cells induced by over-expression of oncogenic Ras in mouse. Further, any use of BLT2 inhibitors as tumor angiogenesis-inhibiting therapeutic composition is claimed in the present invention. The present inventors have found that BLT2 antagonist LY255283 or BLT2 antisense oligonucleotide remarkably suppresses a tumor angiogenesis.

According to another aspect of the present invention, there is provided a use of a combination of (a) a substance that inhibits the expression or intracellular signaling of BLT2, and (b) other anti-cancer drugs for the manufacture of a medicament for the treatment of human cancer.

In a preferred embodiment, the combination of BLT2 antagonist LY255283 and epirubicin may be used for the manufacture of a medicament for the treatment of breast cancer. The epirubicin is an anthracycline drug used for chemotherapy. The epirubicin is primarily used against breast and ovarian cancer, gastric cancer, lung cancer, and lymphomas. The present inventors have found that a combined use of BLT2 antagonist LY255283 and a convensional anti-cancer drug epirubicin represents remarkable and synergetic anti-cancer effects against breast cancer.

In a preferred embodiment, the combination of BLT2 antagonist LY255283 and androgen receptor antagonist may be used for the manufacture of a medicament for the treatment of prostate cancer. It is well known that the androgen receptor antagonist, such as bicalutamide, has an anti-cancer activity against human prostate cancer [Biochemical and Biophysical Research Communications, Vol. 357, No. 2, 341-346, 2007]. Many kinds of androgen receptor antagonist is available, for example 6-sulfonamido-quinolin-2-one and 6-sulfonamido-2-oxo-chromene derivatives (U.S. Pat. No. 7,064,207). Therefore, the combined use of BLT2 antagonist LY255283 and an androgen receptor antagonist may represents synergetic anticancer effects against prostate cancer.

According to another aspect of the present invention, there is provided a pharmaceutical composition for the treatment of human cancer, which comprises a substance that inhibits the expression or intracellular signaling of BLT2 as an active ingredient. In the pharmaceutical composition of the present invention, the substance may be chemical compounds, peptides, antibody proteins, nucleotides, antisense oligonucleotides, siRNA oligonucleotides or extract of natural source. The present pharmaceutical composition may comprise a pharmaceutically acceptable carrier in addition.

According to another aspect of the present invention, there is provided a pharmaceutical composition for the treatment of human cancer, which comprises a combination of (a) a substance that inhibits the expression or intracellular signaling of BLT2 and (b) other anti-cancer drugs as active ingredients. The other anti-cancer drugs may be any conventional anti-cancer drugs known to be effective to the corresponding cancers.

According to another aspect of the present invention, there is provided a method for treating a patient with cancer, which comprises administering a therapeutically effective amount of a substance that inhibits the expression or intracellular signaling of BLT2 to the patient. According to another aspect of the present invention, there is provided a method for treating a patient with cancer, which comprises administering a therapeutically effective amount of (a) a substance that inhibits the expression or intracellular signaling of BLT2 and (b) other anti-cancer drugs to the patient.

After a subject is diagnosed as having a neoplasia (e.g., pancreatic, breast, prostate cancer cancer) a method of treatment is selected. In pancreatic cancer, for example, a number of standard treatment regimens are available. In general, pancreatic cancers are one of the most aggressive forms of cancer, and advanced pancreatic cancers are rarely susceptible to conventional treatment methods. For aggressive pancreatic cancer, few therapeutic options are available, and such tumors often correlate with poor clinical outcomes, such as metastasis or death. A subject having aggressive pancreatic cancer is identified as likely to benefit from treatment with a composition of the invention comprising anti-long form BLT2. Thus, the invention provides methods for selecting a therapy for a subject, the method involving identifying a subject as having aggressive neoplasia, such as pancreatic cancer, and administering to the subject a therapeutic combination of the invention.

Even when a subject with neoplasia (e.g., pancreatic, breast, prostate cancer) is identified as having a good clinical outcome, the subject is also likely to benefit from treatment with the methods of the invention (e.g., lower side effects). When methods of the invention indicate that a neoplasia is very aggressive, an aggressive method of treatment should be selected. Aggressive therapeutic regimens typically include one or more of the following therapies: radical mastectomy, radiation therapy, hormone therapy, and chemotherapy. Such methods may be used in combination with the therapeutic methods described herein, particularly for the treatment of pancreatic cancer, which is prone to relapse.

According to another aspect of the present invention, there is provided a method for screening a substance for treating human cancer, which comprises the steps of:
(a) contacting the substance to be analyzed to a cell containing BLT2 gene or protein; and,
(b) measuring the expression or intracellular signaling level of BLT2, wherein if the expression or intracellular signaling level of BLT2 is down-regulated, the substance is determined to have a potency to treat human cancer.

According to the present method, the cell containing the BLT2 gene or protein can be easily prepared by obtaining cells containing their original BLT2 gene or by transfecting cells with a foreign BLT 2 gene. Preferably, the cells containing the BLT2 gene or protein are transformed cancer cells. The cells are first contacted to substances to be analyzed. The term "substance" used herein in conjunction with the present screening method refers to a material tested in the present method for analyzing the influence on the expression level of the BLT2 gene, the amount of the BLT2 protein or the intracellular signaling level of the BLT2 receptor. The substance includes chemical compounds, peptides, antibody proteins, nucleotides, antisense-RNA, siRNA (small interference RNA) and extract of natural source, but not limited to. Afterwards, the expression level of the BLT2 gene, the amount of the BLT2 protein or the intracellular signaling level of the BLT2 receptor in cells is measured. Where the expression level of the BLT2 gene, the amount of the BLT2 protein or the intracellular signaling level of the BLT2 receptor is measured to be down-regulated, the substance is determined to be a candidate to treat human cancers.

The measurement of the expression level of the BLT2 gene could be carried out by a variety of methods known in the art. For example, RT-PCR (Sambrook et al., Molecular Cloning. A Laboratory Manual, 3rd ed. Cold Spring Harbor Press (2001)), Northern blotting (Peter B. Kaufma et al., Molecular and Cellular Methods in Biology and Medicine, 102-108, CRC press), hybridization using cDNA microarray (Sambrook et al., Molecular Cloning. A Laboratory Manual, 3rd ed. Cold Spring Harbor Press (2001)) and in situ hybridization (Sambrook et al., Molecular Cloning. A Laboratory Manual, 3rd ed. Cold Spring Harbor Press (2001)) may be used.

Where the expression level of the BLT2 gene is analyzed by RT-PCT, total RNA is first isolated from cells treated with a substance to be analyzed and a first cDNA strand is then synthesized using oligo dT primer and reverse transcriptase. Then, PCR amplifications are performed using the first cDNA strand as templates and a BLT2-specific primer set. Finally, the PCR amplified products are resolved by electrophoresis and bands are analyzed for assessing the expression level of the BLT2 gene.

The amount of the BLT2 protein may be determined by various immunoassays known in the art. For example, radio-immunoas say, radioimmuno-precipitation, enzyme-linked immunosorbent assay (ELISA), capture-ELISA, inhibition or competition assay and sandwich assay are used for analyzing the amount of the BLT2 protein.

The intracellular signaling level of the BLT2 receptor may be determined by monitoring an event induced by LTB4, e.g., monitoring the rise of the intracellular calcium concentration as described in example using BLT2-expressing cells etc. (e.g., BLT2 overexpressing cells etc.). For example, if the substance reduces the intracellular calcium concentration by LTB4 in BLT2-expressing cells, it can be judged as BLT2 antagonist.

According to another aspect of the present invention, there is provided a kit for detecting human cancer, which comprises a primer or probe having a nucleotide sequence complementary to the nucleotide sequence of BLT2 gene as set forth in SEQ ID NO: 2. Therefore, any methodology or kit developed based on the information that BLT2 overexpression is detected at various human cancer may be included in the present invention.

The probes or primers used in the present kit has a complementary sequence to the nucleotide sequence of the BLT2 gene. The term "complementary" with reference to sequence used herein refers to a sequence having complementarity to the extent that the sequence anneals or hybridizes specifically with the nucleotide sequence of the BLT2 gene under certain annealing or hybridization conditions. In this regard, the term "complementary" used herein has different meaning from the term "perfectly complementary". The probes or primers used in the present invention can be one or more mismatch, so long as such mismatches are not sufficient to completely preclude specific annealing or hybridization to the BLT2 gene.

As used herein the term "probe" means a linear oligomer of natural or modified monomers or linkages, including deoxyribonucleotides and ribonucleotides, capable of specifically binding to a target polynucleotide. The probe may be naturally occurring or artificially synthesized. The probe is preferably single stranded.

Preferably, the probes used in the present invention are oligodeoxyribonucleotides.

The probe of this invention can be comprised of naturally occurring dNMP (i.e., dAMP, dGM, dCMP and dTMP), modified nucleotide, or non-natural nucleotide. The primer can also include ribonucleotides. For instance, the probes of this invention may include nucleotides with backbone modifications such as peptide nucleic acid (PNA) (M. Egholm et al., Nature, 365:566-568 (1993)), phosphorothioate DNA, phosphorodithioate DNA, phosphoramidate DNA, amide-linked DNA, MMI-linked DNA, 2'-O-methyl RNA, alpha-DNA and methylphosphonate DNA, nucleotides with sugar modifications such as 2'-O-methyl RNA, 2'-fluoro RNA, 2'-amino RNA, 2'-O-alkyl DNA, 2'-O-allyl DNA, 2'-O-alkynyl DNA$_1$ hexose DNA, pyranosyl RNA, and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-), inosine, and diaminopurine.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. The suitable length of primers will depend on many factors, including temperature, application and source of primer, generally, 15-30 nucleotides in length. Shorter primers generally need lower temperature to form stable hybridization duplexes to templates.

The sequences of primers are not required to have perfectly complementary sequence to templates. The sequences of primers may comprise some mismatches, so long as they can be hybridized with templates and serve as primers. Therefore, the primers of this invention are not required to have perfectly complementary sequence to the BLT2 gene as templates; it is sufficient that they have complementarity to the extent that they anneals specifically to the nucleotide sequence of the BLT2 gene for acting as a point of initiation of synthesis. The primer design may be conveniently performed with referring to the BLT2 gDNA or cDNA sequences, preferably, cDNA sequence. For instance, the primer design may be carried out using computer programs for primer design (e.g., PRIMER 3 program).

Exemplified primers of this invention is set forth in SEQ ID NO: 9 (sense primer) and SEQ ID NO: 10 (antisense primer).

According to a preferred embodiment, the diagnosis or detection kit for human cancers comprising probes is in the form of microarray, more preferably DNA or cDNA microarray, most preferably cDNA microarray.

In microarray, the present probes serve as hybridizable array elements and are immobilized on substrates. A preferable substrate includes suitable solid or semisolid supporters, such as membrane, filter, chip, slide, wafer, fiber, magnetic or nonmagnetic bead, gel, tubing, plate, macromolecule, microparticle and capillary tube. The hybridizable array elements are arranged and immobilized on the substrate. Such immobilization occurs through chemical binding or covalent binding such as UV. In an embodiment of this invention, the hybridizable array elements are bound to a glass surface modified to contain epoxi compound or aldehyde group or to a polylysin-coated surface. Further, the hybridizable array elements are bound to a substrate through linkers (e.g. ethylene glycol oligomer and diamine).

DNAs to be examined with a microarry of this invention may be labeled, and hybridized with array elements on microarray. Various hybridization conditions are applicable, and for the detection and analysis of the extent of hybridization, various methods are available depending on labels used.

The present method for diagnosing human cancer may be carried out in accordance with hybridization. For such analysis, probes, which have a complementary sequence to the nucleotide sequence of the BLT2 gene, are used.

Using probes hybridizable with the BLT2 gene or cDNA, preferably cDNA, human cancer is diagnosed or detected by hybridization-based assay. According to a preferred embodiment, some modifications in the probes of this invention can be made unless the modifications abolish the advantages of the probes. Such modifications, i.e., labels linking to the probes generate a signal to detect hybridization. Suitable labels include fluorophores (e.g., fluorescein), phycoerythrin, rhodamine, lissamine, Cy3 and Cy5 (Pharmacia), chromophores, chemiluminescers, magnetic particles, radioisotopes (e.g., $P^{32}$ and $S^{35}$), mass labels, electron dense particles, enzymes (e.g., alkaline phosphatase and horseradish peroxidase), cofactors, substrates for enzymes, heavy metals (e.g., gold), and haptens having specific binding partners, e.g., an antibody, streptavidin, biotin, digoxigenin and chelating group, but not limited to. Labeling is performed according to various methods known in the art, such as nick translation, random priming (Multiprime DNA labeling systems booklet, "Amersham" (1989)) and kination (Maxam & Gilbert, Methods in Enzymology, 65:499 (1986)). The labels generate signal detectable by fluorescence, radioactivity, measurement of color development, mass measurement, X-ray diffraction or absorption, magnetic force, enzymatic activity, mass analysis, binding affinity, high frequency hybridization or nanocrystal.

The nucleic acid sample (preferably, cDNA) to be analyzed may be prepared using mRNA from various biosamples. The biosample is preferably a cell from bladder, prostate, pancreatic or breast cancer. Instead of probes, cDNA may be labeled for hybridization-based analysis.

Probes are hybridized with cDNA molecules under stringent conditions for detecting human cancers. Suitable hybridization conditions may be routinely determined by optimization procedures. Conditions such as temperature, concentration of components, hybridization and washing times, buffer components, and their pH and ionic strength may be varied depending on various factors, including the length and GC content of probes and target nucleotide sequence. The detailed conditions for hybridization can be found in Joseph Sambrook, et al., Molecular Cloning, A Laboratory Manual, Cold Spring Harbor Laboratory Press, Cold Spring Harbor, N.Y. (2001); and M. L. M. Anderson, Nucleic Acid Hybridization, Springer-Verlag New York Inc. N.Y. (1999). For example, the high stringent condition includes hybridization in 0.5 M NaHPO$_4$, 7% SDS (sodium dodecyl sulfate) and 1 mM EDTA at 65° C. and washing in 0.1×SSC (standard saline citrate)/0.1% SDS at 68° C. Also, the high stringent condition includes washing in 6×SSC/0.05% sodium pyrophosphate at 48° C. The low stringent condition includes e.g., washing in 0.2×SSC/0.1% SDS at 42° C.

Following hybridization reactions, a hybridization signal indicative of the occurrence of hybridization is then measured. The hybridization signal may be analyzed by a variety of methods depending on labels. For example, where probes are labeled with enzymes, the occurrence of hybridization may be detected by reacting substrates for enzymes with hybridization resultants. The enzyme/substrate pair useful in this invention includes, but not limited to, a pair of peroxidase (e.g., horseradish peroxidase) and chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) or naphtol/pyronine; a pair of alkaline phosphatase and bromochloroindolylphosphate (BCIP), nitro blue tetrazolium (NBT), naphthol-AS-B1-phosphate or ECF substrate; and a pair of glucosidase and t-NBT (nitroblue tetrazolium) or m-PMS (phenzaine methosulfate). Where probes are labeled with gold particles, the occurrence of hybridization may be detected by silver staining method using silver nitrate.

In these connections, where the present method for diagnosing human cancers is carried out by hybridization, it comprises the steps of (i) contacting a nucleic acid sample to a probe having a nucleotide sequence complementary to the nucleotide sequence of the BLT2 gene; and (ii) detecting the occurrence of hybridization.

The signal intensity from hybridization is indicative of human cancers. When the hybridization signal to BLT2 cDNA from a sample to be diagnosed is measured to be stronger than normal samples, the sample can be determined to have human cancers.

According to a preferred embodiment, the primers of this invention are used for amplification reactions.

The term used herein "amplification reactions" refers to reactions for amplifying nucleic acid molecules. A multitude of amplification reactions have been suggested in the art, including polymerase chain reaction (hereinafter referred to as PCR) (U.S. Pat. Nos. 4,683,195, 4,683,202, and 4,800,159), reverse transcription-polymerase chain reaction (hereinafter referred to as RT-PCR) (Sambrook, J. et al., Molecular Cloning. A Laboratory Manual, 3rd ed. Cold Spring Harbor Press (2001)), the methods of Miller, H. I. (WO 89/06700) and Davey, C. et al. (EP 329,822), ligase chain reaction (LCR) (17, 18), Gap-LCR (WO 90/01069), repair chain reaction (EP 439,182), transcription-mediated amplification (TMA)(19) (WO 88/10315), self sustained sequence replication (WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245), nucleic acid sequence based amplification (NASBA) (U.S. Pat. Nos. 5,130,238, 5,409,818, 5,554,517, and 6,063,603), strand displacement amplification and loop-mediated isothermal amplification (LAMP), but not limited to. Other amplification methods that may be used are described in, U.S. Pat. Nos. 5,242,794, 5,494,810, 4,988,617 and in U.S. Ser. No. 09/854,317.

According to the most preferred embodiment, the amplification reaction is carried out in accordance with PCR (polymerase chain reaction) which is disclosed in U.S. Pat. Nos. 4,683,195, 4,683,202, and 4,800,159.

PCR is one of the most predominant processes for nucleic acid amplification and a number of its variations and applications have been developed. For example, for improving PCR specificity or sensitivity, touchdown PCR(24), hot start PCR(25, 26), nested PCR(2) and booster PCR(27) have been developed with modifying traditional PCR procedures. In addition, real-time PCR, differential display PCR (DD-PCR), rapid amplification of cDNA ends (RACE), multiplex PCR, inverse polymerase chain reaction (IPCR), vectorette PCR, thermal asymmetric interlaced PCR (TAIL-PCR) and multiplex PCR have been suggested for certain applications. The details of PCR can be found in McPherson, M J., and Moller, S. G. PCR. BIOS Scientific Publishers, Springer-Verlag New York Berlin Heidelberg, N.Y. (2000), the teachings of which are incorporated herein by reference in its entity.

Where the present method for diagnosing human cancers is carried out using primers, the nucleic acid amplification is executed for analyzing the expression level of the BLT2 gene. Because the present invention is intended to assess the expression level of the BLT2 gene, the level of the BLT2 mRNA in samples is analyzed.

Therefore, the present invention performs nucleic acid amplifications using mRNA molecules in samples as templates and primers to be annealed to mRNA or cDNA.

For obtaining mRNA molecules, total RNA is isolated from samples. The isolation of total RNA may be performed by various methods (Sambrook, J. et al., Molecular Cloning. A Laboratory Manual, 3rd ed. Cold Spring Harbor Press (2001); Tesniere, C. et al., Plant Mol. Biol. Rep., 9:242 (1991); Ausubel, F. M. et al., Current Protocols in Molecular Biology, John Willey & Sons (1987); and Chomczynski, P. et al., Anal. Biochem. 162:156 (1987)). For example, total RNA in cells may be isolated using Trizol. Afterwards, cDNA molecules are synthesized using mRNA molecules isolated and then amplified. Since total RNA molecules used in the present invention are isolated from human samples, mRNA molecules have poly-A tails and converted to cDNA by use of dT primer and reverse transcriptase (PNAS USA, 85:8998 (1988); Libert F, et al., Science, 244:569 (1989); and Sambrook, J. et al., Molecular Cloning. A Laboratory Manual, 3rd ed. Cold Spring Harbor Press (2001)). cDNA molecules synthesized are then amplified by amplification reactions.

The primers used for the present invention is hybridized or annealed to a region on template so that double-stranded structure is formed. Conditions of nucleic acid hybridization suitable for forming such double stranded structures are described by Joseph Sambrook, et al., Molecular Cloning, A Laboratory Manual, Cold Spring Harbor Laboratory Press, Cold Spring Harbor, N.Y. (2001) and Haymes, B. D., et al., Nucleic Acid Hybridization, A Practical Approach, IRL Press, Washington, D.C. (1985).

A variety of DNA polymerases can be used in the amplification step of the present methods, which includes "Klenow" fragment of *E. coli* DNA polymerase I, a thermostable DNA polymerase and bacteriophage T7 DNA polymerase. Preferably, the polymerase is a thermostable DNA polymerase such as may be obtained from a variety of bacterial species, including *Thermus aquaticus* (Taq), *Thermus thermophilus* (Tth), *Thermus filiformis, Thermis flavus, Thermococcus literalis,* and *Pyrococcus furiosus* (Pfu).

When a polymerization reaction is being conducted, it is preferable to provide the components required for such reaction in excess in the reaction vessel. Excess in reference to components of the amplification reaction refers to an amount of each component such that the ability to achieve the desired amplification is not substantially limited by the concentration of that component. It is desirable to provide to the reaction mixture an amount of required cofactors such as $Mg^{2+}$, and dATP, dCTP, dGTP and dTTP in sufficient quantity to support the degree of amplification desired. All of the enzymes used in this amplification reaction may be active under the same reaction conditions. Indeed, buffers exist in which all enzymes are near their optimal reaction conditions. Therefore, the amplification process of the present invention can be done in a single reaction volume without any change of conditions such as addition of reactants.

Annealing or hybridization in the present method is performed under stringent conditions that allow for specific binding between the primer and the template nucleic acid. Such stringent conditions for annealing will be sequence-dependent and varied depending on environmental parameters.

The amplified BLT2 cDNA molecules are then analyzed to assess the expression level of the BLT2 gene. For example, the amplified products are resolved by a gel electrophoresis and the bands generated are analyzed to assess the expression level of the BLT2 gene. When the expression level of the BLT2 gene from a sample to be diagnosed is measured to be higher than normal samples, the sample can be determined to have human cancers.

In these connections, where the present method for diagnosing human cancers is carried out by amplification, it comprises the steps of (i) amplifying a nucleic acid sample by use of a primer having a nucleotide sequence complementary to the nucleotide sequence of the BLT2 gene; and (ii) analyzing the amplified products to determine the expression level of the BLT2 gene.

In a preferred embodiment, the kit may comprise a pair of primers having a forward sequence of SEQ ID NO: 9 and a reverse sequence of SEQ ID NO: 10. This primer set can detect both of the long form and short form BLT2.

In a preferred embodiment, the kit may comprise a pair of primers having a forward sequence of SEQ ID NO: 11 and a reverse sequence of SEQ ID NO: 12. This primer set can detect only long form of BLT2 because the primer recognizes the front part of long form CDS.

According to another aspect of the present invention, there is provided a kit for detecting human cancer, which comprises an antibody binding specifically to BLT2 protein. The diagnosing kit for human cancer may be constructed by incorporating an antibody binding specifically to the BLT2 protein.

The antibody against the BLT2 protein used in this invention may polyclonal or monoclonal, preferably monoclonal. The antibody could be prepared according to conventional techniques such as a fusion method (Kohler and Milstein, European Journal of Immunology, 6:511-519 (1976)), a recombinant DNA method (U.S. Pat. No. 4,816,56) or a phage antibody library (Clackson et al, Nature, 352:624-628 (1991) and Marks et al, J. Mol. Biol., 222:58, 1-597 (1991)). The general procedures for antibody production are described in Harlow, E. and Lane, D., Antibodies: A Laboratory Manual, Cold Spring Harbor Press, New York, 1988; Zola, H., Monoclonal Antibodies: A Manual of Techniques, CRC Press, Inc., Boca Raton, Fla., 1984; and Coligan, CURRENT PROTOCOLS IN IMMUNOLOGY, Wiley/Greene, NY, 1991, which are incorporated herein by references. For example, the preparation of hybridoma cell lines for monoclonal antibody production is done by fusion of an immortal cell line and the antibody producing lymphocytes. This can be done by techniques well known in the art. Polyclonal antibodies may be prepared by injection of the BLT2 protein antigen to suitable animal, collecting antiserum containing antibodies from the animal, and isolating specific antibodies by any of the known affinity techniques.

Where the diagnosing method of this invention is performed using antibodies to the BLT2 protein, it could be carried out according to conventional immunoassay procedures for detecting human cancer.

Such immunoassay may be executed by quantitative or qualitative immunoassay protocols, including radioimmunoassay, radioimmuno-precipitation, enzyme-linked immunosorbent assay (ELISA), capture-ELISA, inhibition or competition assay, sandwich assay, flow cytometry, immunofluorescence assay and immuoaffinity assay, but not limited to. The immunoassay and immuostaining procedures can be found in Enzyme Immunoassay, E. T. Maggio, ed., CRC Press, Boca Raton, Fla., 1980; Gaastra, W., Enzyme-linked immunosorbent assay (ELISA), in Methods in Molecular Biology, Vol. 1, Walker, J. M. ed., Humana Press, NJ, 1984; and Ed Harlow and David Lane, Using Antibodies: A Laboratory Manual, Cold Spring Harbor Press, 1999, which are incorporated herein by references.

For example, according to the radioimmunoassay method, the radioisotope (e.g., $C^{14}$, $I^{125}$, $P^{32}$ and $S^{35}$) labeled antibody may be used to detect the BLT2 protein.

In addition, according to the ELISA method, the example of the present method may comprise the steps of: (i) coating a surface of solid substrates with cell lysate to be analyzed; (ii) incubating the coated cell lysate with a primary antibody to the BLT2 protein; (iii) incubating the resultant with a secondary antibody conjugated with an enzyme; and (iv) measuring the activity of the enzyme.

The solid substrate useful in this invention includes carbohydrate polymer (e.g., polystyrene and polypropylene), glass, metal and gel, most preferably microtiter plates.

The enzyme conjugated with the secondary antibody is that catalyzing colorimetric, fluorometric, luminescence or infrared reactions, e.g., including alkaline phosphatase, β-galactosidase, luciferase, Cytochrome $P_{450}$ and horseradish peroxidase. Where using alkaline phosphatase, bromochloroindolylphosphate (BCIP), nitro blue tetrazolium (NBT) or ECF may be used as a substrate for color-developing reactions; in the case of using horseradish peroxidase, chloronaphtol, aminoethylcarbazol, diaminobenzidine, D-luciferin, lucigenin (bis-N/-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) or naphtol/pyronine may be used as a substrate; and in the case of using glucose oxidase, t-NBT (nitroblue tetrazolium) or m-PMS (phenzaine methosulfate) may be used as a substrate.

Where the present method is performed in accordance with the capture-ELISA method, the specific example of the present method may comprise the steps of: (i) coating a surface of a solid substrate with a capturing antibody capable of binding specifically to the BLT2 protein; (ii) incubating the capturing antibody with a cell sample to be analyzed; (iii) incubating the resultant of step (ii) with a detecting antibody which is capable of binding specifically to the BLT2 protein and conjugated with a label generating a detectable signal; and (iv) detecting the signal generated from the label conjugated with the detecting antibody.

The detecting antibody has a label generating a detectable signal. The label includes, but not limited to, a chemical (e.g., biotin), an enzymatic (e.g., alkaline phosphatase, horseradish peroxidase, β-galactosidase and Cytochrome P450X a radioactive (e.g., $C^{14}$, $I^{125}$, $P^{32}$ and $S^{35}$), a fluorescent (e.g., fluorescein), a luminescent, a chemiluminescent and a FRET (fluorescence resonance energy transfer) label. Various labels and methods for labeling antibodies are well known in the art (Ed Harlow and David Lane, Using Antibodies, A Laboratory Manual, Cold Spring Harbor Laboratory Press, 1999).

The detection of the signal generated from the label conjugated with the detecting antibody can be carried out by various processes well known in the art. The detection of the signal enables to analyze the BLT2 protein in a quantitative or qualitative manner. Where biotin and luciferase are used as labels, the signal detection may be achieved by use of streptavidin and luciferin, respectively.

The measurement of signal intensities generated from the immunoassay described above is indicative of human cancer. When the signal to the BLT2 protein in a biosample to be diagnosed is measured to be higher than normal samples, the biosample can be determined to have human cancer.

The kit of the present invention may optionally include other reagents along with primers, probes or antibodies described above. For instance, where the present kit may be used for nucleic acid amplification, it may optionally include the reagents required for performing PCR reactions such as buffers, DNA polymerase (thermostable DNA polymerase obtained from *Thermus aquaticus* (Taq), *Thermus thermophilus* (Tth), *Thermus filiformis*, *Thermis flavus*, *Thermococcus literalis*, and *Pyrococcus furiosus* (Pfu)), DNA polymerase cofactors, and deoxyribonucleotide-5-triphosphates.

The kits, typically, are adapted to contain in separate packaging or compartments the constituents afore-described.

The kits for detecting or diagnosing human cancer permit to determine the development, aggravation and alleviation of human cancer. In this regard, the term used herein "detecting or diagnosing" with reference to disease means not only the determination of the existence of disease but also the development, aggravation and alleviation of disease.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriersand formulations can be found in Remington's Pharmaceutical Sciences (19th ed., 1995), which is incorporated herein by reference. A pharmaceutical composition of this invention may be administered orally or parenterally (e.g., intravenous injection, subcutaneous injection, intramuscular injection and local injection).

The administration of a compound or a combination of compounds for the treatment of a neoplasia may be by any suitable means that results in a concentration of the therapeutic that, combined with other components, is effective in ameliorating, reducing, or stabilizing a neoplasia. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

The term "therapeutically effective amount" as used herein means an amount of the substance that is capable of producing a medically desirable result in a treated subject. The correct dosage of the pharmaceutical compositions of this invention will be varied according to the particular formulation, the mode of application, age, body weight and sex of the patient, diet, time of administration, condition of the patient, drug combinations, reaction sensitivities and severity of the disease. According to a preferred embodiment of this invention, a daily suitable dosage unit for human host ranges from 0.001-100 mg/kg (body weight). Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 µg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 mg/Kg body weight. In other embodiments, it is envisaged that doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

According to the conventional techniques known to those skilled in the art, the pharmaceutical compositions of this invention can be formulated with pharmaceutical acceptable carrier and/or vehicle as described above, finally providing several forms including a unit dosage form. Non-limiting examples of the formulations include, but not limited to, a solution, a suspension or an emulsion, an extract, an elixir, a powder, a granule, a tablet, a capsule, emplastra, a liniment, a lotion and an ointment.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with the thymus; (v) formulations that allow for convenient dosing, such that doses are administered, for example, once every one or two weeks; and (vi) formulations that target a neoplasia by using carriers or chemical derivatives to deliver the therapeutic agent to a particular cell type (e.g., neoplastic cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a neoplasia, the composition may include suitable parenterally acceptable carriers and/or excipients. The active therapeutic agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active antineoplastic therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Practical and presently preferred embodiments of the present invention are illustrated as shown in the following Examples. However, it will be appreciated that those skilled in the art, on consideration of this disclosure, may make modifications and improvements within the spirit and scope of the present invention.

EXAMPLES

Example 1

Figure 1B:
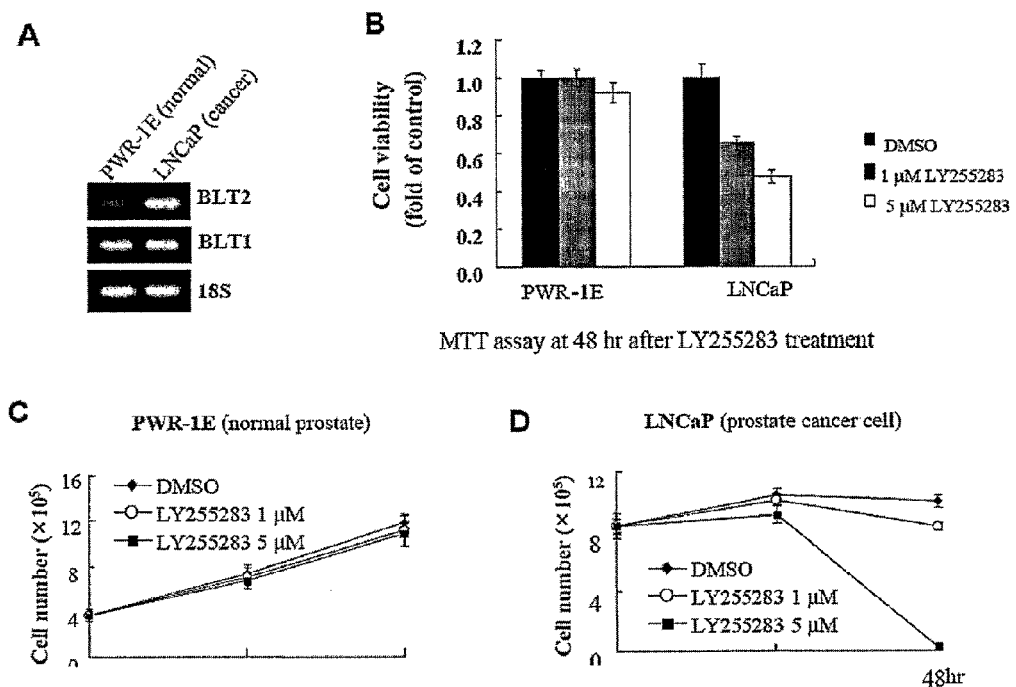
FIG. 1b shows the effect of BLT2 antagonist LY255283 on prostate cancer cell viability. The BLT2 antagonist significantly reduced prostate cancer cells viability.

BLT2 Antagonist Significantly Reduces Prostate Cancer Cells Viability (1) RT-PCR (Panel A of FIG. 1b)

In prostate cancer cells and normal cells, BLT2 mRNA level was analyzed by RT-PCR. Total cellular RNA was extracted using Easy-Blue reagent (Intron Co.) and dissolved in diethylpyrocarbonate-treated water. 2 μg of RNA was reverse transcribed for 30 min at 45° C. and pre-denatured for 5 min at 94° C. in 20 μl in buffer containing 10 mM Tris (pH 8.3), 50 mM KCl, 5 mM $MgCl_2$, 1 mM each of dATP, dCTP, dGTP, and dTTP, and oligo(dT) primers. Then PCR reaction was performed as follows. For BLT1 and BLT2, samples denatured at 94° C. for 30 sec, annealed at 67° C. for 30 sec and extended at 72° C. for 30 sec for 33 repetitive cycles. For 18 s, samples were denatured at 94° C. for 30 sec, annealed at 55° C. for 30 sec and extended at 72° C. for 30 sec for 19 repetitive cycles. The products were separated by electrophoresis on 1.5% agarose gels and visualized with ethidium bromide staining. The primers, purchased from Genotech Inc. (Korea) were as follows. BLT1 forward: 5'-TAT GTC TGC GGA GTC AGC ATG TAC GC-3' (SEQ ID NO: 13); reverse: 5'-CCT GTA GCC GAC GCC CTA TGT CCG-3' (SEQ ID NO: 14)); BLT2 forward: 5'-AGC CTG GAG ACT CTG ACC GCT TTC G-3' (SEQ ID NO: 9), reverse: 5'-GAC GTA GAG CAC CGG GTT GAC GCT A-3' (SEQ ID NO:10); 18 s forward: 5'-TTC GGA ACT GAG GCC ATG AT-3' (SEQ ID NO: 15), reverse: 5'-TTT CGC TCT GGT CCG TCT TG-3' (SEQ ID NO: 16)). The expression of housekeeping gene 18s RNA was used to normalize for transcription and amplifications among samples. The result showed that the level of BLT2 mRNA was elevated in LNCaP cells, prostate cancer cells, as compared with PWR-1 E, prostate normal epithelial cells.

(2) MTT Assay (Panel B of FIG. 1b)

The effect of LY255283, BLT2 antagonist, on cell viability was examined by MTT assay. PWR-1E cells were seeded at a density of $1.0 \times 10^4$ cells/well and LNCaP cells were seeded at a density of $1.5 \times 10^4$ cells/well in 96-well culture dishes. After 36 hr, the medium was replaced with serum free RPMI 1640 and cells were stimulated with DMSO or LY255283 of increasing concentration. MTT (1 mg/mu) was added at 48 hr after LY255283 treatment and after 4 hr of further incubation the medium was replaced with DMSO. Then cells were incubated at room temperature for 10 min. The spectrophotometric absorbance of the samples was determined by using Ultra Multifunctional Microplate Reader at 540 nm. LNCaP cells and PWR-1E cells were stimulated with LY255283 of various concentration in serum free RPM11640. The treatment with LY255283 resulted in a dose dependent reduction of LNCaP cell viability with no effect on PWR-1 E cells.

(3) Cell Counting (Panels C and D of FIG. 1b)

The effect of LY255283 was observed by counting of cell number. The cells were grown in 6-well cluster dishes to 70% confluence with 10% FBS-supplemented medium. At day 0, the medium was replaced with serum free RPMI 1640 and cells were stimulated with DMSO or 1 μM and 5 μM LY255283. The cells were harvested at various intervals. Cells were washed with PBS and collected by brief trypsinization. Total cell number was determined by counting each sample in duplicate with a hemocytometer using trypan blue dye. The cells treated with LY255283 in serum free RPM11640 were harvested at various intervals. The number of LNCaP cells was significantly reduced by LY255283, but not PWR-1 E cells. These results indicated that the reduction of cell viability by LY255283 was significant in LNCaP cells which expressed elevated level of BLT2 mRNA. In contrast, PWR-1 E cells which expressed few level of BLT2 were not affected by LY255283.

Example 2

Figure 1C:
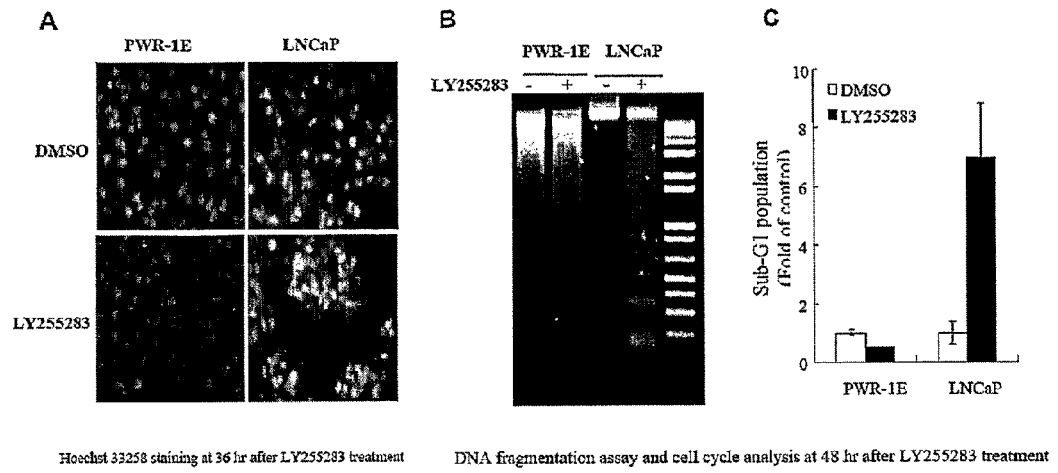
FIG. 1c shows the effect of BLT2 antagonist LY255283 on prostate cancer cell apoptosis. The BLT2 blockade induced apoptosis in prostate cancer cells.

Apoptosis Induced by BLT2 Blockade in Prostate Cancer Cells (1) Hoechst 33258 Staining (Panel A of FIG. 1c)

Prostate cancer cells grown in 6-well cluster dishes were stimulated with 5 μM LY255283 for 36 hr in serum free RPMI 1640. The cells were fixed for 10 min with 4% formaldehyde and stained with Hoechst 33258 (50 μg/ml) (Sigma) for 10 min at 37° C. and observed under fluorescence microscopy (Carl Zeiss). Nuclei condensation of fragmentation was observed in LY255283-treated LNCaP cells, but not PWR-1E cells.

(2) DNA Fragmentation Assay (Panel B of FIG. 1c)

LNCaP and PWR-1 E cells were treated with 5 μM LY255283 for 48 hr and DNA fragmentation assay was performed. DNA fragmentation was shown by the harvesting of total cellular DNA. Cells were grown in 10 cm plates to 70% confluence with 10% FBS-supplemented medium. Then the media was replaced with serum free RPMI 1640 and the cells were treated with 5 μM LY255283 for 48 hr. Cellular DNA from cells was extracted incubating with lysis buffer (1 mM EDTA, 10 mM Tris, 120 mM NaCl, 1% SDS and 100 μg/ml proteinase K, pH 8.0) for 12 hr at 50° C. The lysate was centrifuged for 10 min at 13,000×g to separate the fragment DNA. The supernatant was then extracted twice with phenol/chloroform/isoamyl alcohol and precipitated with absolute ethanol. The pellet was resuspended in Tris-EDTA and 10 mg/ml RNase A and the DNA was separated on a 1.8% agarose gel. After electrophoresis, gels were stained with ethidium bromide, and the DNA was visualized by UV light. A smear of different sizes of DNA fragments was observed in LY255283-treated LNCaP cells.

(3) Cell Cycle Analysis (Panel C of FIG. 1c)

After LNCaP cells and PWR-1E cells were treated with 5 μM LY255283 for 48 hr, the cells were fixed with 70% ethanol and stained with Pl. Cell cycle was analyzed using flow cytometry. The cells grown in 6-well cluster dishes were stimulated with 5 μM LY255283 for 48 h in serum free RPMI 1640. The cells which were collected by brief trypsinization were fixed for 12 hr with 70% ethanol at 4° C. The cells were resuspended in PBS containing RNase A (100 μg/ml) and incubated for 30 min at 37° C. The cells were stained with propidium iodide (50 μg/ml) (Sigma). Acquisition and analysis was performed by FACS using Cell Quest Alias software (BD Bioscience). The graph showed the relative fold of sub-G1 population in LY255283-treated LNCaP and PWR-1E cells. The increased population of cells with sub-GI DNA content was detected in LY255283-treated LNCaP cells. The various methods for the measurement of apoptosis showed similar results, indicating that LY255283 induce apoptosis in prostate cancer LNCaP cells, but not prostate normal cells. In prostate cancer and normal cells, the differential effect on LY255283-induced apoptosis indicated that BLT2 plays an important role in survival of prostate cancer cells which expressed elevated level of BLT2. FIG. 1c showed that the LY255283-induced cell death was involved in apoptosis concomitantly. The apoptotic cells were detected by staining of fragmented nuclei by Hoechst33258 and Pl and DNA fragmentation assay.

Example 3

Figure 1D:
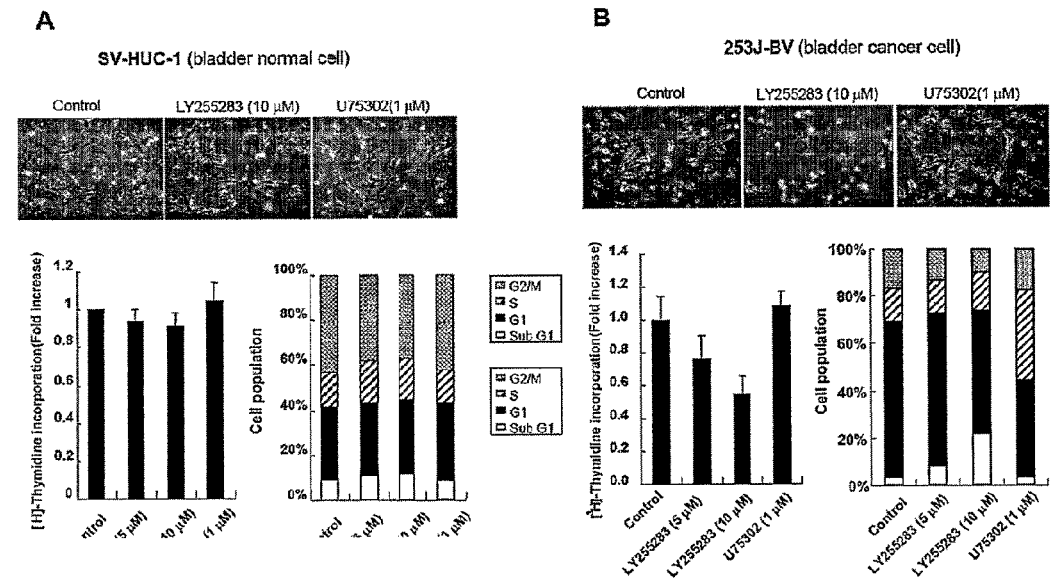
FIG. 1d shows the effect of BLT2 antagonist on bladder cancer cell cycle and apoptosis. The LY255283 induced cell cycle arrest in sub-G1 phase and apoptosis of bladder cancer cells.

LY255283 Induced Cell Cycle Arrest in sub-G1 Phase and Apoptosis of Bladder Cancer Cells (1) Morphological Changes Using Light Microscopy (Panels A and B of FIG. 1d)

Bladder cancer cells grown in 6 well-plate were treated with 10 μM LY255283, 1 uM U75302 for 48 hr. Cells were then viewed using light microscopy (×100). SV-HUC-1 cell (normal bladder cell) and 253J-BV cell (bladder cancer cell) were treated with different concentrations (1-10 μM) of LY255283 (BLT2 specific antagonist), U75302 (BLT1 specific antagonist) for 48 hr. As shown in panels A and B of FIG. 1d, 253J-BV cells exhibited membrane blebbing, detached from plate treated only LY255283. But normal bladder cell line was not effect on morphological change treated with BLT antagonists.

(2) [$^3$H]-Thymidine Incorporation Assay (Lower Left Graphs in Panels A and B of FIG. 1d)

Cells were seed in 96-well plate at the density of $1.0 \times 10^4$/well. After 24 hr incubation in RPMI 1640 supplemented with 10% FBS, the media was replaced with RPMI 1640 containing 0.5% FBS for 12 hr. After cells were treated with different concentration BLT antagonists. Then [$^3$H]-thymidine (1 μCi/ml) (PerkinElmer Life Sciences) was added at 12 hr after antagonists treatment and after 36 hr of further incubation, cells were harvested on the filtermat (PerkinElmer Life Science) and filtermat was dried and packaged in the sample bag (PerkinElmer Life Science). Finally, Betaplate scint (PerkinElmer Life Science) was added to the filtermat, and the radioactivity was counted in a liquid scintillation counter (MicroBeta, Wallac/PerkinElmer). The specific LTB4 receptor 2 antagonist LY255283 caused a concentration dependent inhibition of thymidine incorporation in 253J-BV cells, but not SV-HUC-1 cells. LY255283 inhibited proliferation by at least 50% at a concentration of 10 μM at 48 hr.

(3) Cell Cycle Analysis (Bottom Right Graphs of Panels A and B of FIG. 1d)

The cells grown in 6-well plate were stimulated with 5 μM and 10 μM LY255283, 1 μM U75302 for 48 h in RPMI 1640 containing 0.5% FBS. The cells which were collected by brief trypsinization were fixed overnight with 70% ethanol at 4° C. The cells were resuspended in PBS containing RNase A (100 μg/ml) and incubated for 30 min at 37° C. The cells were stained with propidium iodide (50 μg/ml) (Sigma). Acquisition and analysis was performed by FACS using Cell Quest Alias software (BD Bioscience). Similar effects were seen in the cell cycle progression. Cells were treated with BLT antagonist for 48 hours and the cell cycle population was measured by flow cytometry. In brief, cells were plated in 6 well plate and then treated with LY255283, U75302 for 48 hr. At the end of the treatment, the cells were harvested and then centrifuged. The cells fixed in ice-cold 70% ethanol for 24 hr and centrifuged. The pellet were resuspended in 0.5 ml phosphate-buffered saline (PBS) and incubated with Pl 1 mg/ml treatment for 15 min. LY255283 inhibited cell growth by arresting cell cycle at sub-G1 in dose dependent manner.

LTB4 receptor 1 specific antagonist U75302 was not effect on cell proliferation and cell cycle in both SV-HUC-1 and 253J-BV cells. Then LY255283 10 μM and U75302 1 μM, these concentration only effect on bladder cancer cell line 253J-BV, was used for further studied.

Example 4

LY255283 Induced Apoptosis and Loss of Mitochondrial Membrane Potential in 253J-BV Bladder Cancer Cell A selective BLT2 antagonist LY255283 has been shown to inhibit proliferation and induced cell death of human bladder cancer cells. LY255283-induced cell death was examined to determine whether it was apoptosis or not.

Figure 1E:
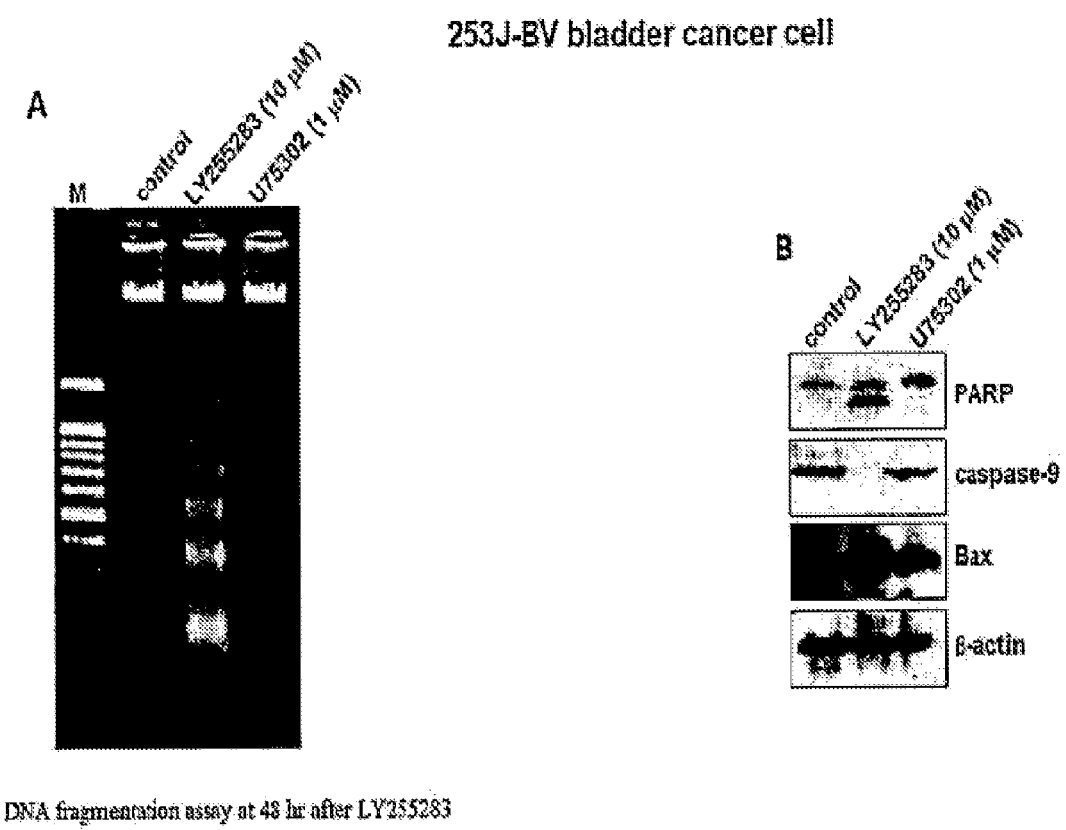
FIG. 1e shows the effect of BLT2 antagonist LY255283 on bladder cancer cell apoptosis. The LY255283 induced apoptosis and loss of mitochondrial membrane potential in 253J-BV bladder cancer cell.
Figure 1E:
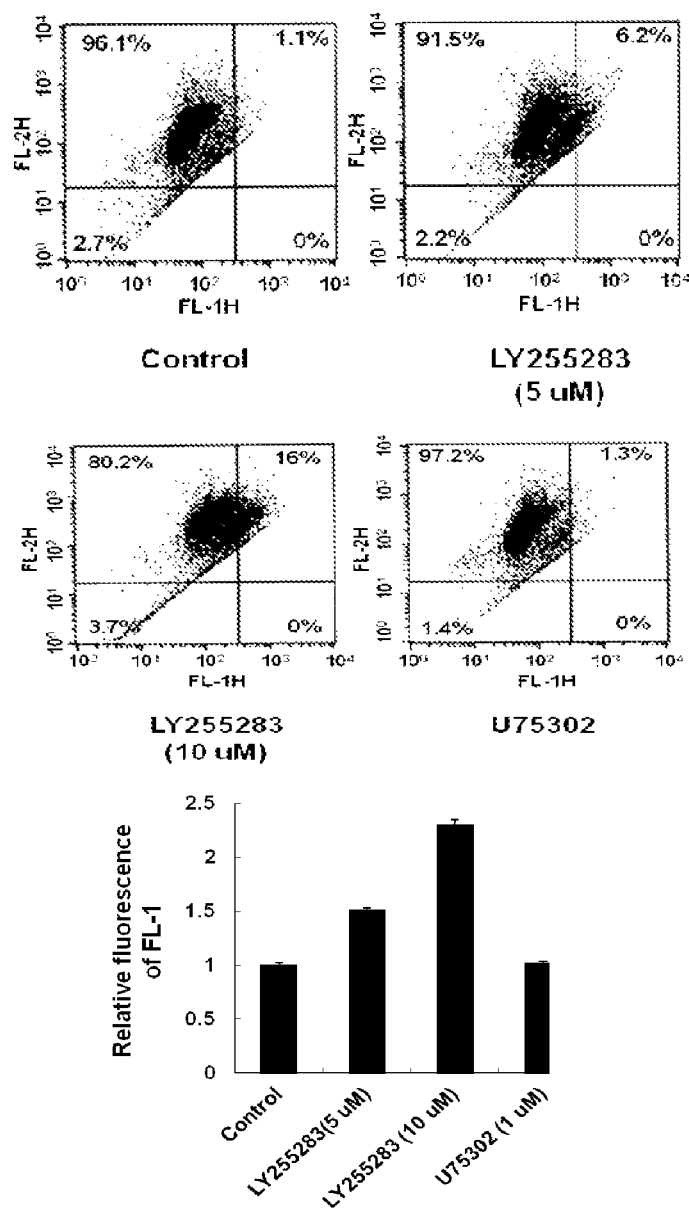
Figure 1F:
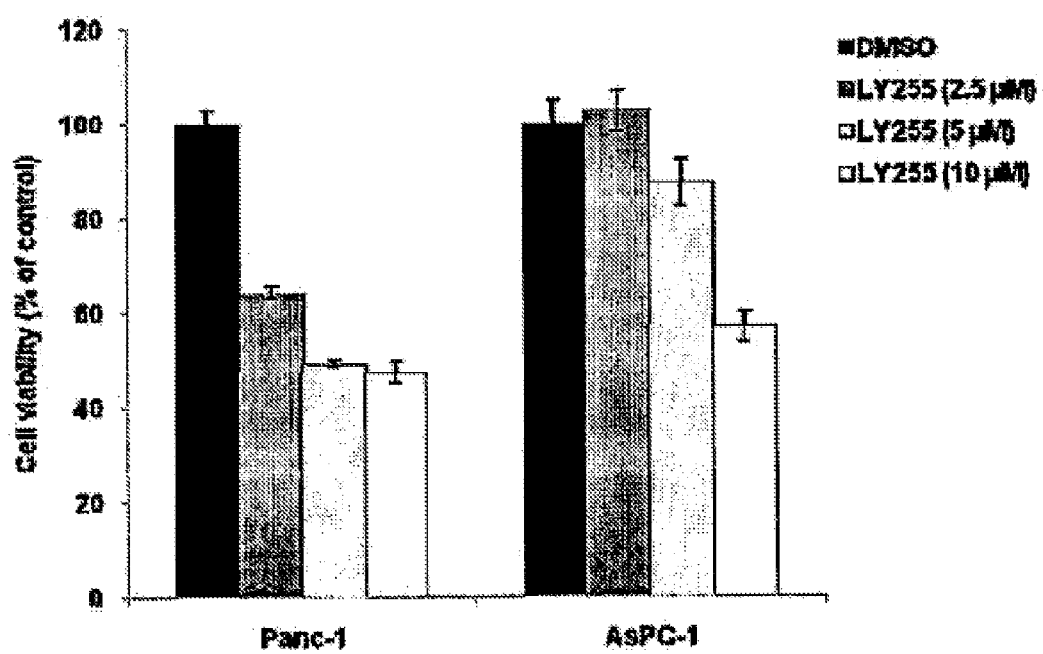
FIG. 1f shows the effect of BLT2 antagonist LY255283 on pancreatic cancer cell apoptosis. The LY255283 induced apoptosis in pancreatic cancer cells (Panc-1 &AsPC-1).

(1) DNA Fragmentation (Panel A of FIG. 1e)

DNA fragmentation was shown by the harvesting of total cellular DNA. Cells were grown in 100 mm plates to 80% confluence with 10% FBS-supplemented medium. Then the media was replaced with RPMI 1640 with 0.5% FBS and the cells were treated with 10 μM LY255283 and 1 μM for 48 hr. Cellular DNA from cells extracted incubating with lysis buffer (1 mM EDTA, 10 mM Tris, 120 mM NaCl, 1% SDS and 100 μg/ml proteinase K, pH 8.0) for 12 hr at 50° C. The lysate was centrifuged for 10 min at 13,000×g to separate the fragment DNA from intact chromatin (nuclear pellet). The supernatant was then extracted twice with phenol/chloroform/isoamyl alcohol and precipitated with absolute ethanol. The pellet was resuspended in Tris-EDTA and 10 mg/ml RNaseA and the DNA was separated on a 1.8% agarose gel.

After electrophoresis, gels were stained with ethidium bromide, and the DNA was visualized by UV light. Apoptosis is characterized by fragmentation of chromosomal DNA. The effect of BLT antagonists on DNA damage of bladder cancer cell line was investigated. As expected, cells treated with LY255283 for 48 hr was observed a ladder like pattern of DNA fragments. In contrast, the control cell and treated U75302 cell not observed DNA fragments.

(2) Western Blot (Panel B of FIG. 1e)

Cells were washed with cold PBS and cells were scraped into lysis buffer [20 mM Tris-HCl (pH 7.5), 15 OmM NaCl, 0.5% NP-40, 5 mM EDTA, 1% triton X-100 added protease inhibitors] at 4° C. Harvested protein samples were heated at 95° C. for 5 min and then subjected to SDS-PAGE on acrylamide gels, followed by transfer to polyvinylidene difluoride membranes for 90 min at 100 V. The membranes were blocked for 1 h with Tris-buffered saline (TBS) containing 0.05% (vol/vol) Tween 20 plus 5% (wt/vol) nonfat dry milk and then incubated with appropriate antibodies (PARP, 1:2000 dilution, Caspase-9, 1:2000 dilution, Bax 1:2000 dilution, actin, 1:3000 dilution) in 5% nonfat milk overnight at 4° C. Then membrane bound protein-antibody complex incubated for 2 hr with HRP-conjugated secondary antibody before development with an enhanced chemiluminescence kit (Amersham Biosciences, UK). The poly ADP-ribose polymerase (PARP) cleavage have been well established as important indices of apoptosis. Apoptosis induction was observed in 253J-BV cell line after 48 hr LY255283 treatment. Western blot analysis showed that LY255283 caused a reduction of pro-caspase 9. These result indicate that LY255283 induced apoptosis was caspase dependent manner. And pro-apoptotic protein, Bax, was significant increased when cells were treated with 10 μM LY255283 for 48 hr. However, there was no significant change in the level of protein in cells treated with U75302 compared with control.

(3) Measurement of Mitochondrial Membrane Potential (Panel C of FIG. 1e)

Mitochondrial damage is important to the apoptosis affected by the caspase-9 pathway. To evaluate the effect of LY255283 on the mitochondria membrane potential (MMP), cell were pretreated with the fluorescent mitochondria specific cationic dye, JC-1, and changes in membrane potential were measured by flow cytometry. Cells grown in 6 well-plates for 24 hr washed PBS and incubated in RPMI 1640 with 0.5% FBS containing different concentrations of LY255283 and U75302 for 48 hr. After cells were treated with 5 μg/ml of JC-1 for 30 min. Then removal of JC-1, washed with PBS, harvested by trypsinization, and resuspended in PBS. Sample was measured at 530 nm (FL-1 green) and 590 nm (FL-2 red) using a flow cytometry. LY255283 led to a drop in mitochondria potential after 48 hr of treatment at a concentration of 10 μM. LY255283 treatment increased green fluorescence (FL-1) about 2.5 fold compare with control cells. These result that LY255283 induced apoptosis might be linked to mitochondrial function and membrane permeability. And because of the loss of mitochondrial membrane potential in a LY255283 treated cells, it was speculated that caspase may play an essential role in the process of apoptosis.

Example 5

LY255283 Induced Apoptosis in Pancreatic Cancer Cells (Panc-1 & AsPC-1)

To investigate the effect of the selective BLT2 antagonist LY255283 on pancreatic cancer cell proliferation and survival, cell viability was determined by MTT assay after Panc-1 and AsPC-1 cells were exposed to LY255283 for 48 hr.

(1) Human Pancreatic Cancer Cell Lines and Cell Culture

Two human pancreatic cancer cell lines were used: Panc-1 and AsPC-1. Panc-1 cells were grown in DMEM, and AsPC-1 cells were grown in RPMl 1640. Cells were plated as monolayers in the medium supplemented with 10% heat inactivated FBS, 100 units/ml penicillin, and 100 μg/ml streptomycin at 37° C. under a humidified 95%/5% (v/v) mixture of air and $CO_2$.

Figure 10:
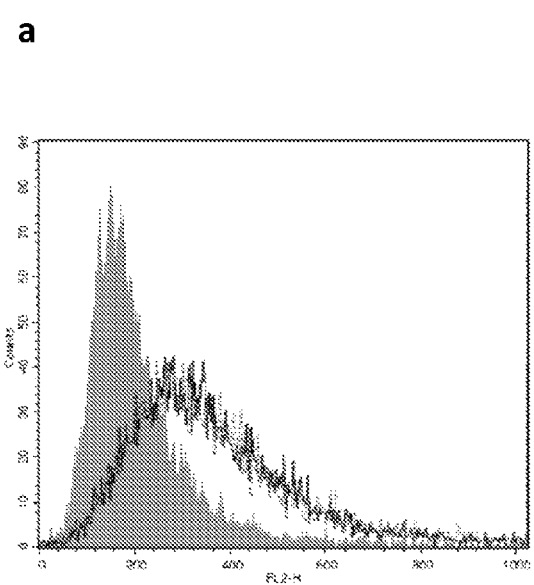
FIGS. 10a and 10b depict the production of antibody to long form BLT2 having BLT neutralizing activity. 253J-BV bladder cancer cells were incubated with FITC-conjugated anti-BLT2 or an isotype control antibody, and BLT2 expression was evaluated by flow cytometry (red and green color). Fluorescence intensity of BLT2 expression level was measured.

(2) MTT Assay (FIG. 10

Cells were plated in 96-well plates at a concentration of 10,000 cells/well. After incubation for 24 h, cells were serum-starved for 3 h, and then various concentrations (2.5 μM, 5 μM and 10 μM) of LY255283 were added. At the end of experiments, 25μ! of a 5 mg/ml MTT solution, diluted in PBS, was added into the 96-well plates. The plates were incubated at 37° C. in 5% $CO_2$ atmosphere for 3 hr, allowing viable cells to reduce the yellow tetrazolium salt (MTT) into dark blue formazan crystals. At the end of the 3 h incubation, the MTT solution was removed and 100 μl of dimethyl sulfoxide was added to dissolve the formazan crystals. To ensure complete dissolution of the formazan crystals, the plates were vortexed gently at low speed for 10 min. The absorbance in individual wells was determined at 540 nm by a microplate reader.

The BLT2 antagonist LY255283 reduced a significant cell viability in pancreatic cancer cells in a dose-dependent manner in both Panc-1 and AsPC-3 cells at 48 h relative to control cells. LY255283 diminished cell viability in dose-dependent manner in both Panc-1 and AsPC-3 cells.

Example 6

Figure 1G:
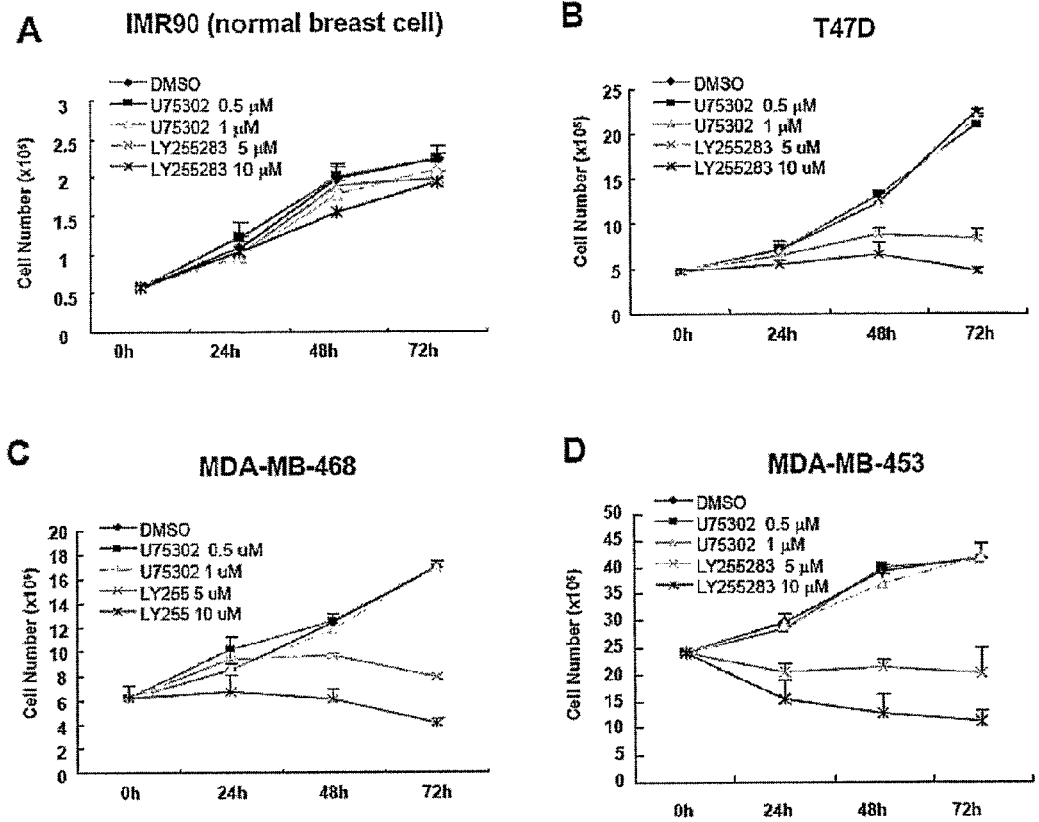
FIG. 1g shows the effect of BLT2 antagonist LY255283 on breast cancer cell viability. The BLT2 antagonist significantly reduced breast cancer cells viability.

BLT2 Antagonist Significantly Reduced Breast Cancer Cells Viability (1) Cell Growth Assay (Panels A-D of FIG. 1g)

To investigate the effect of BLT2 antagonist, LY255283 and BLT1 antagonist, U75302 on growth of breast cancer, breast cancer cell line, T47D (ER+), MDA-MB-468 (ER−), MDA-MB-453 (ER−) and normal IMR-90 cells were used. Cells were treated with LY255283 and U75302 in a dose-dependent manner and analyzed for cell number using the trypan blue dye exclusion method. Cells were plated at a density of $0.5 \times 10^5$ or $5 \times 10^5$ cells/well on 12-well plate. After 24 h, cells were incubated in media containing 0.5% serum for 3 hr. Then, cells were treated with U75302 (0.5, 1 μM), LY255283 (5, 10 μM) and incubated at 37° C. for indicated time (24, 48, and 72 hr). To measure the growth of cell, the treated cells were then trypsinized at each time point, and counted by the trypan-blue exclusion method The treatment of LY255283 for blockade of BLT2 signaling significantly inhibits the growth of all of the breast cancer cell lines via a dose- and time-dependent manner. In addition, normal IMR-90 did not affect by LY255283. Contrast to LY255283, U75302 had no effect on growth of both breast cancer cells and normal cells. These results indicate that BLT2 signaling plays a key role in growth in breast cancer. This indicates the possibility that BLT2 is a potential therapeutic target in breast cancer.

Example 7

LY255283 Induced Partial Apoptotic Cell Death in Breast Cancer Cells

To test involvement of BLT2 signaling on survival of breast cancer cells, the treated cell with BLT antagonist were analyzed for measure of apoptosis using DAPl staining and DNA fragmentation assay.

Figure 1H:
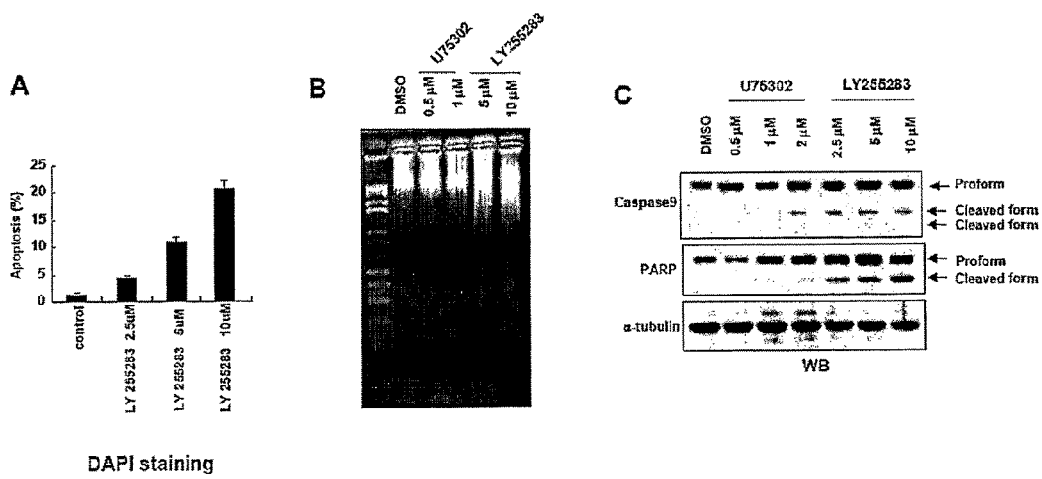
FIG. 1h shows the effect of BLT2 antagonist LY255283 on breast cancer cell apoptosis. The LY255283 induced a partial apoptotic cell death in breast cancer cells.

(1) DAPI Staining (Panel A of FIG. 1h)

Cells were grown on sterile coverslips at a density of $7\times10^5$ cells/plate in 35-mm plate. After 24 h, cells incubated in media containing serum-free for 3 h. Then, cells were treated with U75302 (0.5, 1 μM), LY255283 (5, 10 μM) and incubated at 37° C. for 48 h. Then, cells were fixed with 70% cold-ethanol for 30 min at room temperature, and then washed once with PBS. DAPI (50 ng/ml) was added to the fixed cells, incubated for 20 min at room temperature, and washed with PBS. Cells were mounted and examined by fluorescence microscopy. Apoptotic cells were identified by the condensation and fragmentation of their nuclei. The percentage of apoptotic cells was calculated as the ratio of apoptotic cells to total cells counted. A minimum of 500 cells were counted for each treatment.

(2) DNA Fragmentation Assay (Panel B of FIG. 1h)

Cells were plated a density of $2\times10^6$ cells/plate in 100-mm plate. After 24 hr, cells incubated in media containing serum-free for 3 hr. Then, cells were treated with U75302 (0.5, 1 μM), LY255283 (5, 10 μM) and incubated at 37° C. for 48 h. Both attached and detached cells were collected and resuspended in a lysis buffer (20 mM Tris/HCl, pH 8.0, 0.1 mM EDTA, 1% SDS, and 0.5 mg/ml proteinase K) and then incubated at 50° C. for overnight. DNA was extracted with phenol/chloroform. DNA sample were electrophoresed on 1.8% agarose gel and visualized by ethidium bromide staining.

(3) Western Blotting (Panel C of FIG. 1h)

Cells were plated a density of $2\times10^6$ cells/plate in 100-mm plate. After 24 h, cells incubated in media containing serum-free for 3 hr. Then, cells were treated with U75302 (0.5, 1 μM), LY255283 (5, 10 M) and incubated at 37° C. for 48 hr. Both attached and detached cells were collected and lysed with buffer (40 mM Tris-HCl pH 8.0, 120 mM NaCl, 0.1% Nonidet-P40, 100 mM phenylmethylsulfonyl fluoride, 1 mM Na orthovanadate, 2 ug/ml leupeptin, 2 ug/ml aprotinin). Proteins were separated by SDS-PAGE and transferred onto a nitrocellulose membrane. The membrane was blocked with 5% nonfat dry milk in Tris-buffered saline and then incubated with primary antibodies against caspase-9, PARP for 1 h at room temperature. Blots were developed with a peroxidase-conjugated secondary antibody and proteins were visualized by enhanced chemiluminescence (ECL) procedures (Amersham, USA) according to the manufacturer's recommendation Treatment of LY255283 (2, 5, 10 μM) induces apoptosis via a dose-dependent manner in MDA-MB-468 cells (A). Consistent with DAPI staining, DNA fragmentation analysis of LY255283-treated MDA-MB-468 cells showed a laddering pattern characteristic of apoptosis (panel B). However, U75302 (0.5, 1 μM) did not induce DNA fragmentation (panel B). Next, to test whether caspase are involved in LY255283-induced apoptosis, activation of caspase-9 and PARP cleavage was analyzed using Western blotting. LY255283 induces a dose-dependent activation of caspase-9 and cleavage of PARP (panel C). However, U75302 did not affect on caspase-9 activation and PARP cleavage (panel C). These results demonstrate that LY255283, BLT2 antagonist, induces apoptosis via caspase-dependent signaling in breast cancer cells.

Example 8

Combined Therapy (LY255283 and Epirubicin) Induced a Synergistic Apoptosis in Breast Cancer MCF7

(1) Cell Culture and Agents

The MCF-10A cells were grown in DMEM/F-12 (50:50, v/v) medium supplemented with 5% (v/v) horse serum, 100 units/ml penicillin, 100 mg/ml streptomycin, 0.5 mg/ml hydrocortisone, 100 ng/ml cholera toxin, 10 mg/ml insulin, 10 ng/ml epidermal growth factor and 1% (w/v) L-glutamine at 37° C. under a humidified 95%/5% (v/v) mixture of air and $CO_2$. MCF-7 cells were grown in RPMI 1640 supplemented with 10% heat inactivated FBS, 100 units/ml penicillin, and 100 μg/ml streptomycin at 37° C. under a humidified 95%/5% (v/v) mixture of air and $CO_2$. BLT2 antagonist (LY255283) was purchased from BIOMOL (Plymouth Meeting, Pa.). Epirubicin was purchase from MP Biomedicals. Cells were cultured for 24 h. After serum-starved for 6 h, cells were treated with 10 μM LY255283, 100 ng/ml epirubicin, or combination treatment in which cells were preincubation with LY255283 for 30 min before epirubicin treatment. In MCF-7 human breast cancer cells, BLT2 mRNA level was highly induced by RT-PCR analysis. However, in MCF-10A human normal breast cells, no induced expression of BLT2 is detected. These results for expression of BLT2 mRNA in human breast cancer cell indicate that the BLT2 may play an important role in breast cancer.

Figure 1I:
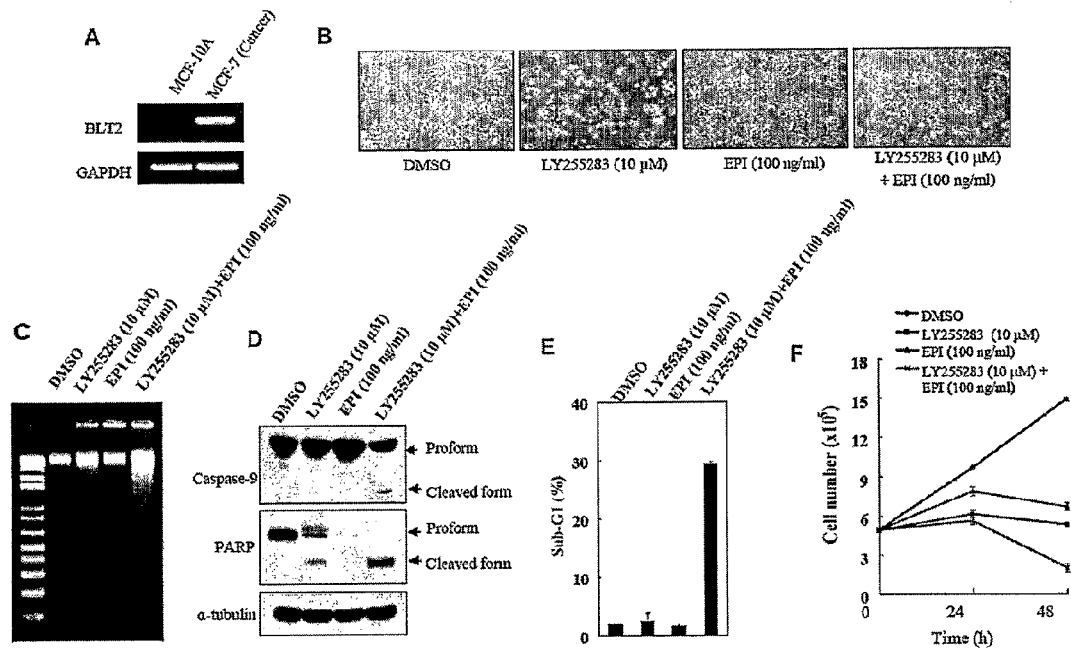
FIG. 1i shows the effect of combined treatment of BLT2 antagonist LY255283 with epirubicin on breast cancer cells. The combined therapy (LY255283 & epirubicin) induced a synergistic apoptosis in breast cancer MCF7.

(2) RT-PCR of BLT2 (A of FIG. 1i)

Total cellular RNA was extracted with Easy Blue™ (Intron, Korea). Thereafter, 1.25 μg of total RNA was reverse transcribed for 1 h at 42° C. and amplified by PCR with specific primers for human BLT2 (sense, 5'-AGCCTG-GAGACTCTGACCGCTTTCG-3' (SEQ ID NO: 9); antisense, 5'-GACGTAGAGCACCGGGTTGACGCTA-3' (SEQ ID NO: 10)). The PCR protocol for BLT2 involved 33 cycles of denaturation at 94° C. for 60 s, annealing at 68° C. for 40 s, an elongation at 72° C. for 45 s. Amplified PCR products were subjected to electrophoresis on 1.5% agarose gel, after which bands were visualized by ethidium bromide staining and visualized under UV illumination.

(3) Morphological Changes Using Light Microscopy (Panel B of FIG. 1i)

Cells were seeded in 6 well-plate. After serum-starved for 6 h, cells were treated with 10 μM LY255283, 100 ng/ml epirubicin, or combination treatment in which cells were preincubation with LY255283 for 30 min before epirubicin treatment. Cells were cultured for 48 hr. Cells were then viewed using light microscopy (×20). The morphology of cells was examined under light microscopy (×20). The treatment with the combination of LY255283 (10 μM) plus epirubicin (100 ng/ml) induced dramatic morphological changes in MCF-7 cells at 48 hr. Over time, the treated cells became rounded and exhibited membrane blebbing, chromatin condensation, and nuclear fragmentation and finally detached from the microplate. These morphological changes are consistent with apoptosis.

(4) DNA Fragmentation Assay (Panel C of FIG. 1i)

After exposure to treatments, both attached and detached cells were harvested and suspended in lysis buffer (10 mM Tris-HCl, pH 8.0, 120 mM NaCl, 1 mM EDTA, and 1% SDS) containing proteinase K (100 μg/ml) on ice. Crude DNA samples were extracted twice with phenol/chloroform/isoamyl alcohol (25:24:1) and precipitated with absolute ethanol. The DNA pellet was resuspended in Tris-EDTA and 10 mg/ml RNase A. DNA samples were electrophoresed on 1.8% agarose gel and visualized by ethidium bromide staining. Epirubicin caused only tiny increase in cell death. However, when LY255283 (10 μM) is treated along with epirubicin (100 ng/ml) together, a sinergistic enhanced DNA fragmentation was observed.

(5) Western Blot Analysis (Panel D of FIG. 1i)

Cellular protein was isolated with a protein extraction buffer containing 120 mM NaCl, 40 mM Tris-HCl (pH 8.0) and 0.1% NP-40. Equal amounts (100 μg/ml) of proteins were fractionated on 10% SDS-PAGE gels and transferred to polyvinylidene difluoride membranes. The membranes were then blocked for 1 hr with TBS containing 0.05% (v/v) Tween 20 plus 5% (w/v) nonfat dry milk and incubated with anti-PARP and casepase-9 primary antibodies, respectively. After washing with TBS containing 0.05% (v/v) Tween 20, the membranes were incubated with HRP-conjugated secondary antibody followed by enhanced chemiluminescent staining using the ECL system (Amersham Biosciences, UK). To assess if the cell death observed above represents apoptosis, a Western blot analysis of apoptotic proteins was performed with epirubicin, LY355283, or a combination of the two drugs. When cells treated with two drugs, casepase-9 has become activated. PARP cleavage was detectable when cells treated with LY255283 alone (10 μM) but epirubicin alone (100 ng/ml). In contrast, the cleaved PARP band was much more noticeable with the combination treatment of two drugs. These results indicated that combination of LY255283 and epirubicin induces apoptosis through caspase-dependent pathway in MCF-7 cells.

(6) Cell Cycle Analysis (E of FIG. 1i)

Flow cytometric analysis was performed to detect and quantify apoptosis. Cells were fixed in PBS with 70% ethanol overnight. After centrifugation, the cells were washed with PBS and resuspended in a solution of PBS with RNase A (100 μg/ml) for 30 min at 37° C. Propidium iodide (50 μg/ml) was then added before FACS.

Acquisition and analysis was performed by FACScan using Cell Quest Alias software (BD Bioscience). Cells with their DNA content less than that of Gi phase cells (sub-Gi) were assumed to be apoptotic. Sub-G1 population is highly increased by the combined treatment of LY255283 (10 μM) with epirubicin (100 ng/ml) by FACS analysis.

(7) Cell Growth (Panel F of FIG. 1i)

To determine the rate of cell growth, cells were seeded at approximately $2.5 \times 10^5$ cells/35-mm. The cell were treated with 10 μM LY255283 and 100 ng/ml epirubicin for 24 h and 48 h. At times indicated, plates were rinsed twice with PBS to remove dead cells and debris. Live cells on the plates were trypsinized and collected separately. Cells from each plate were counted four times using the Coulter cell counter. The average number of cells from plates was used for growth rate determination. Cell number is decreased significantly by the combined therapy of LY255283 (10 μM) with epirubicin (100 ng/ml).

Example 9

Figure 2A:
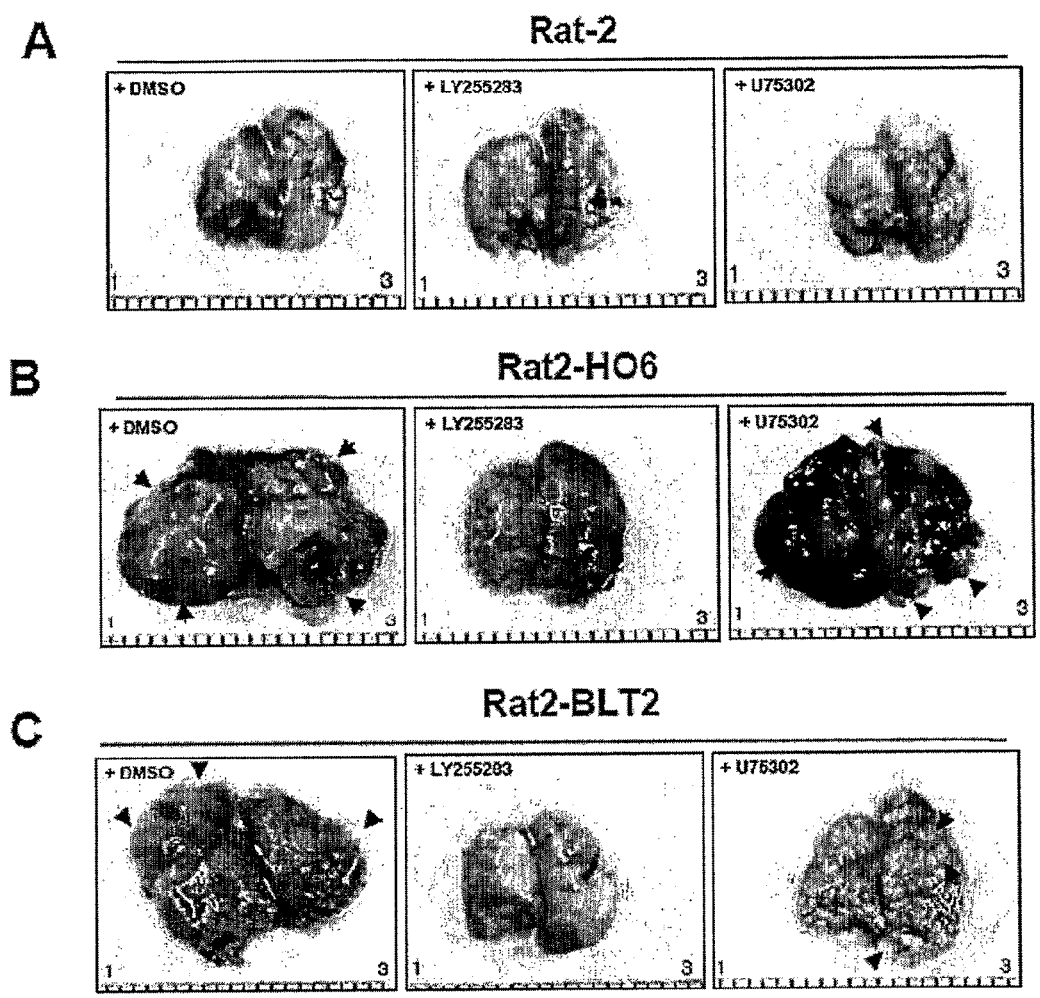
FIG. 2a shows the effect of BLT2 antagonist LY255283 on metastasis of cancer cells. The LY255283 suppressed metastasis of Ras-transformed cancer cells.

LY255283 Suppressed Metastasis of Ras-transformed Cancer Cells (1) Experimental Metastasis Assay (Panels A-C of FIG. 2a)

All experimental animals used in this study were treated according to guidelines approved by the Institutional Animal Care and Use Committee of Korea University. Female nude mice (Charles River, Wilmington, Mass.), four-weeks-old at the time of injection, were used in the experimental metastasis assay. Rat-2, Rat2-HO6, and Rat2-BLT2 cells ($5 \times 10^5$ cells) were prepared for injection from cultures in logarithmic growth at the time of harvest. The cells were briefly treated with 0.025% trypsin and 0.1% EDTA in Hanks' balanced salt solution and quickly removed from trypsin by centrifugation, resuspended in saline containing $LTB_4$, and injected within 1 hr in 0.1 ml into the lateral tail vein with a 26-gauge needle. For inhibitor experiments, U75302 and LY255283 (0.25 mg/kg for BLT1 antagonist and 2.5 mg/kg for BLT2 antagonist) was injected intraperitoneal ~3 and 5 days after injection of cells that were pretreated with inhibitors. The mice were maintained under aseptic barrier conditions until they were sacrificed at 21 days after cell injection (n=8, each group) to identify pulmonary metastasis or to investigate the mortality of mice at the end of the experiment (7 weeks) (n=8, each group).

BLT2 antagonist LY255283 significantly reduced Ras-oncogene expressing transformed cell metastasis in nude mouse. In vivo lung metastasis driven by H-$Ras^{V12}$ (panel B of FIG. 2a) or BLT2 (panel C of FIG. 2a) was reduced by BLT2 inhibition (LY255283) based on the macroscopic and histologic appearance of lung. However, the control Rat-2 cells injection caused no metastasis in lung (panel A of FIG. 2a). Unlike LY255283, DMSO or U75302 caused no suppression on metastasis in response to H-$Ras^{V12}$ or BLT2. Mice were euthanized 21 days after cell injection, and the number of lung metastasis nodules and weight of lung was analyzed in each group. All experimental animals used in this study were treated according to guidelines approved by the Institutional Animal Care and Use Committee of Korea University. Female nude mice (Charles River, Wilmington, Mass.), four weeks old at the time of injection, were used in the experimental metastasis assay. Rat-2, Rat2-HO6, and Rat2-BLT2 cells ($5 \times 10^5$ cells) were prepared for injection from cultures in logarithmic growth at the time of harvest. The cells were briefly treated with 0.025% trypsin and 0.1% EDTA in Hanks' balanced salt solution and quickly removed from trypsin by centrifugation, resuspended in saline containing $LTB_4$, and injected within 1 hr in 0.1 ml into the lateral tail vein with a 26-gauge needle. For inhibitor experiments, DMSO, U75302, or LY255283 (2.5 mg/kg for BLTs antagonist) was injected intraperitoneally 3 and 5 days after injection of cells that were pretreated with inhibitors. The mice were maintained under aseptic barrier conditions until they were sacrificed at 21 days after cell injection (n=8, each group) to identify pulmonary metastasis or to investigate the mortality of mice at the end of the experiment (for 7 weeks) (n=8, each group). The lungs were dissected and fixed in 4% formalin, processed, and embedded in paraffin. Sections (4 μm) were stained with hematoxylin and eosin, and examined and photographed using a BX51 microscope (Olympus, Tokyo, Japan) equipped with a DP71 digital camera (Olympus). Metastasis survival was analyzed in Kaplan-Meyer plots.

Example 10

LY255283 Extended the Survival of Mouse Injected with Ras-cancer Cells (1) Experimental Metastasis Assay and Metastasis Survival Analysis (FIG. 2b)

All experimental animals used in this study were treated according to guidelines approved by the Institutional Animal Care and Use Committee of Korea University. Female nude mice (Charles River, Wilmington, Mass.), four-weeks-old at the time of injection, were used in the experimental metastasis assay. Rat-2, Rat2-HO6, and Rat2-BLT2 cells ($5 \times 10^5$ cells) were prepared for injection from cultures in logarithmic growth at the time of harvest. The cells were briefly treated with 0.025% trypsin and 0.1% EDTA in Hanks' balanced salt solution and quickly removed from trypsin by centrifugation, resuspended in saline containing $LTB_4$, and injected within 1 hr in 0.1 ml into the lateral tail vein with a 26-gauge needle. For inhibitor experiments, U75302 and LY255283 (0.25 mg/kg for BLT1 antagonist and 2.5 mg/kg for BLT2 antagonist) was injected intraperitoneally 3 and 5 days after injection of cells that were pretreated with inhibitors. The mice were maintained under aseptic barrier conditions until they were sacrificed at 21 days after cell injection (n=8, each group) to identify pulmonary metastasis or to investigate the mortality of mice at the end of the experiment (7 weeks) (n=8, each group). Metastasis survival was analyzed in Kaplan-Meyer plots.

BLT2 antagonist LY255283 extended the survival of mouse injected with Ras-oncogene expressing transformed cells. The mortality of mice injected with Rat2-HO6 cells was attenuated by inhibition of BLT2 signaling according to the Kaplan-Meier survival analysis.

Example 11

BLT2 Plays an Important Role in Angiogenesis (1) Preparation and Identification of BLT2 Transgenic (TG) Mice The complete rat BLT2 gene was subcloned from pcDNA3-HA-rBLT2 and inserted into the pCAGGS-B2 vector downstream of the chicken β-actin promoter. The digested and purified construct was injected into fertilized eggs and those eggs were subsequently implanted in foster females. Potential transgenic founder mice were screened by PCR with 2 different primer sets using genomic DNA extracted from the tails of 3-week-old mice to detect transgene integration. Briefly, the mouse tail biopsy was put into 200 μl TES buffer (50 mM Tris-Cl, pH 8.0, 50 mM EDTA, 0.5% SDS). Proteinase K (final concentration: 200 μg/ml) was added and it was incubated overnight at 55° C. Mouse genomic DNA was obtained after phenol extraction and ethanol precipitation. The primers for screening the BLT2 transgenic mice were as follows: forward, 5'-GCGCAGGGACTTC-CTTTGTC-3' (SEQ ID NO: 17) and 5'-GCTCTAGAGC-CTCTGCTAACC-3' (SEQ ID NO: 18); reverse, 5'-CCGATGGGTGGCACAATTGAC-3' (SEQ ID NO: 19). The PCR protocol for BLT2 involved 35 cycles of denaturation at 96° C. for 60 s, annealing at 52° C. for 30 s, and elongation at 72° C. for 120 s, followed by an extension at 72° C. for 10 min. The amplified PCR products (924 bp and 677 bp, respectively) were subjected to electrophoresis on a 1.0% agarose gel, after which the bands were visualized by ethidium bromide staining. The positive founder obtained was bred with female mice of the same strain (FVB). Potential positive litters (F1) were screened by PCR as described above. To verify BLT2 overexpression, total RNA was isolated from 6-wk-old BLT2 transgenic mice and age-matched control mice using Easy Blue™. Thereafter, 1 μg of total RNA was reverse transcribed for 60 minutes at 42° C. and amplified by PCR with primers for mouse BLT2 (forward, 5'-CAGCATGTACGCCAGCGTGC-3' (SEQ ID NO: 20); reverse, 5'-CGATGGCGCTCACCAGACC-3' (SEQ ID NO: 21)). The PCR protocol involved 28 cycles of denaturation at 95° C. for 30 s, annealing at 69° C. for 30 s, and elongation at 72° C. for 45 s, followed by an extension at 72° C. for 10 min. The PCR products were separated by electrophoresis on 1.5% agarose gels and stained with ethidium bromide.

(2) In Vivo Matrigel Plug Assay

FVB wild-type mice or BLT2 TG mice (female, 8-10 wk old) were subcutaneously injected with 400 μl of growth factor-reduced Matrigel from BD Biosciences containing heparin (20 units) and the agents to be tested. After 7 days, the mice were killed, and the solidified Matrigel was excised, fixed in 10% formalin, embedded in paraffin, cut into 5-μm sections and stained with anti-vWF antibody according to the manufacturer's instructions in the Blood Vessel Staining Kit (Chemicon). Each stained Matrigel section was photographed using a BX51 microscope equipped with a DP71 digital camera (Olympus), and the area of vWF-positive blood vessels was calculated using Image J software.

Figure 3A:
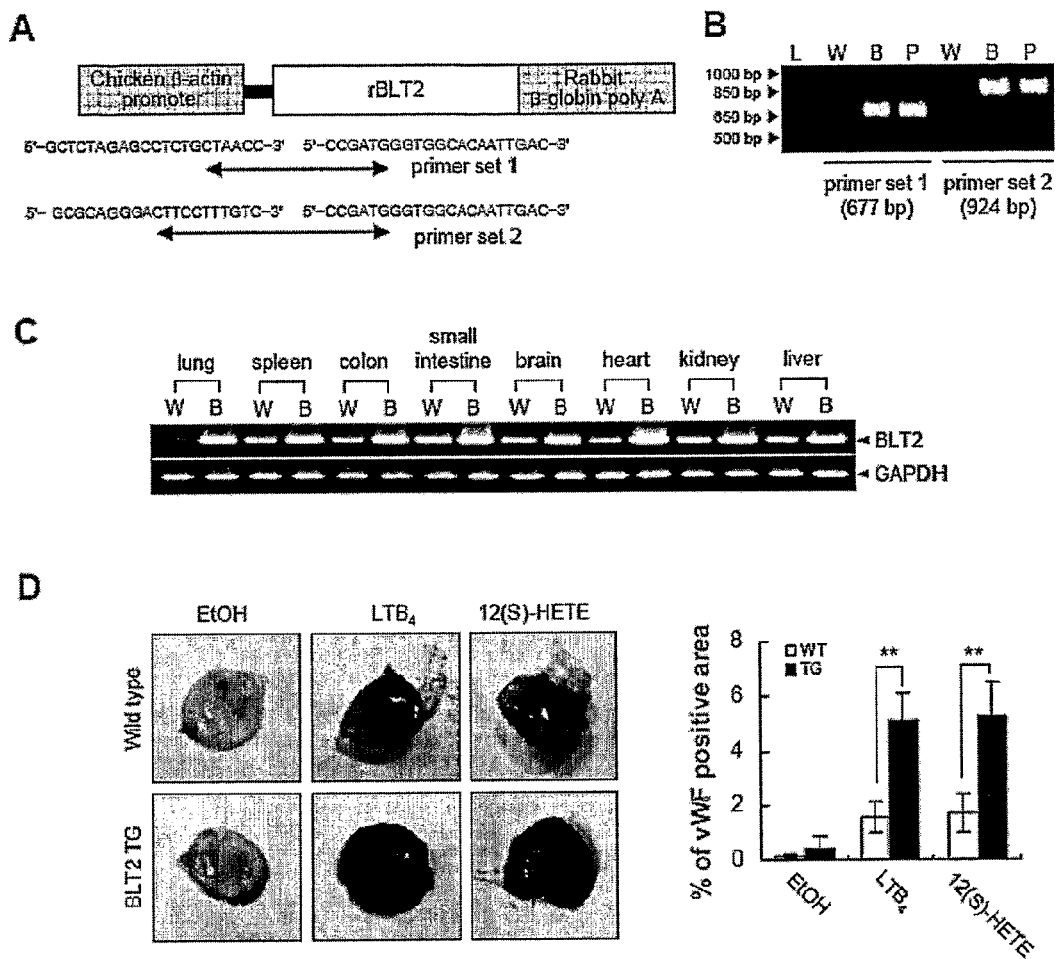
FIG. 3a shows the effect of BLT2 stimulation on tumor angiogenesis BLT2 stimulation induces tumor angiogenesis in vivo.

(3) BLT2 Plays an Important Role in Angiogenesis (Panels A-D of FIG. 3a)

Schematic of the DNA construct used to generate BLT2 TG mice (panels A of FIG. 3a). The two sets of forward and reverse primers are indicated. Identification of founders using PCR (panel B of FIG. 3a). Genomic DNA from a tail biopsy was amplified using the two indicated primer sets. The 677-bp PCR product formed with primer set 1 and the 924-bp product formed with primer set 2 are shown. The DNA construct used to generate BLT2 TG mice was used as a template for the positive control. L: DNA ladder, W: wild-type mice, B: BLT2 TG mice, P: positive control. Overexpression of BLT2 mRNA in various organs of BLT2 TG mice (panel C of FIG. 3a). Total RNA was isolated, reverse transcribed and amplified using specific primers for BLT2 and GAPDH. W: wild type mice, B: BLT2 TG mice. FVB WT and BLT2 TG mice were subcutaneously injected with growth factor-reduced Matrigel containing heparin (20 units) and EtOH, $LTB_4$ (1 μg) or 12(S)-HETE (0.5 μg) (panel D of FIG. 3a). In vivo vessel formation was assayed as described above. Data are expressed as mean fold increases over control.

Example 12

BLT2 Antagonist, LY255283 Suppresses VEGF-Induced Angiogenesis (1) Tube Formation Assay Growth factor-reduced Matrigel (300 μl; BD Biosciences, San Diego, Calif.) was added to each 24-well plate and polymerized for 12 h at 37° C. HUVECs that had been incubated in M199 medium containing 5% FBS for 4 hr were trypsinized and suspended in M199 medium containing 1% FBS. If called for, the cells were pre-treated with inhibitors or antagonists for 30 min before being seeded onto the Matrigel layer to a density of $5 \times 10^4$ cells/well. Cells were then stimulated with $LTB_4$, 12(S)-HETE or VEGF. After 12 hr, five randomly selected areas were photographed using a CKX41 microscope equipped with a DP71 digital camera, and tube lengths were measured and quantified using Image J software, the image processing program developed at the U.S. National Institutes of Health (NIH).

(2) Transmigration Assay

Transmigration assays were performed using Transwell chambers (Corning Costar, Cambridge, Mass.) with 6.5-mm diameter polycarbonate filters (8-1 μm pore size). Confluent HUVECs were incubated for 4 h in M199 medium containing 5% FBS. The lower surfaces of the filters were coated with 10 μl of 1% gelatin for 1 h at 37° C. Cells were trypsinized and suspended in M199 medium containing 1% FBS before being loaded into the upper chambers to a final concentration of $1 \times 10^5$ cells/well.

The cells were then allowed to migrate to the lower side of the chambers, which contained $LTB_4$, 12(S)-HETE or VEGF.

If called for, inhibitors or antagonists were applied to the cells in suspension for 30 min before seeding. After incubation for 3 hr at 37° C. in 5% $CO_2$, the filters were disassembled, and the upper surface of each filter was scraped free of cells by wiping with a cotton swab. Cells that had migrated to the underside of the filter were fixed for 1 min in methanol, stained for 1 min in hematoxylin and finally stained for 30 s in eosin. Cell migration was quantified by counting the cells on the lower side of the filter after they were photographed using a CKX41 microscope equipped with a DP71 digital camera. Five fields were counted in each assay.

Figure 3B:
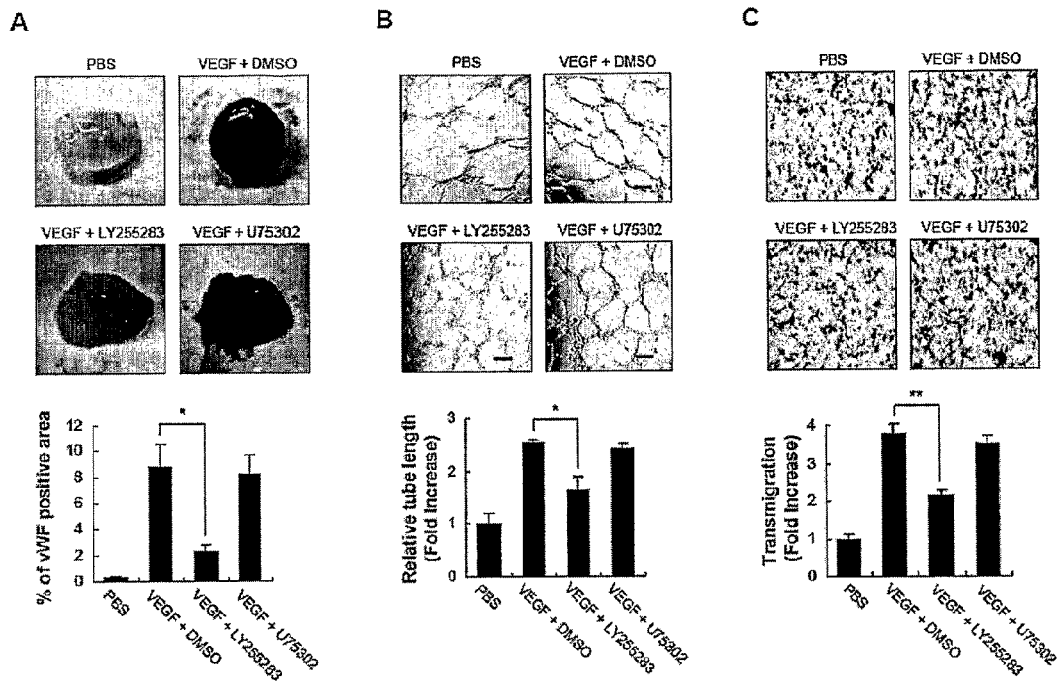
FIG. 3b shows the effect of BLT2 antagonist 255283 on VEGF-induced angiogenesis. The BLT2 antagonist LY255283 suppressed VEGF-induced angiogenesis.

(3) BLT2 Antagonist 255283 Suppresses VEGF-Induced Angiogenesis (Panels A-C of FIG. 3b)

FVB mice were injected subcutaneously with 400 μl of growth factor-reduced matrigel containing heparin (20 units) and PBS, VEGF (100 ng), VEGF+LY255283 (10 μg), VEGF+U75302 (1 μg) or VEGF+DMSO (panels A-C of FIG. 3b). After 7 d, the mice were killed and the solidified matrigel was excised, fixed in 10% formalin, embedded in paraffin, cut into 5 μm sections and stained with anti-von Willebrand factor (vWF) antibody according to the manufacturer's instructions for the Blood Vessel Staining Kit (Chemicon). Each stained matrigel was photographed using a BX51 microscope (Olympus) equipped with a DP71 digital camera and the area of vWF-positive blood vessels was calculated using Image J software. The photographs show representative results that were obtained with each treatment. HUVECs were incubated in M199 medium containing 5% FBS for 4 h and LY255283 and U75302 were added for 30 min to the cells in suspension in M199 medium containing 1% FBS (panel B of FIG. 3b). The cells were plated on growth factor-reduced matrigel-coated 24-well plates and stimulated with VEGF. After 12 h, five randomly selected areas were photographed and tube lengths were measured using Image J software. Bars represent 100 μm. HUVECs were incubated in M199 medium containing 5% FBS for 4 h and LY255283 and U75302 were added for 30 min to cells suspended in M 199 medium containing 1% FBS. The cells were loaded into the upper well and VEGF was present in the lower well (panel C of FIG. 3b). After 3 hr, cells that had migrated to the lower side were stained and counted.

Example 13

Figure 4A:
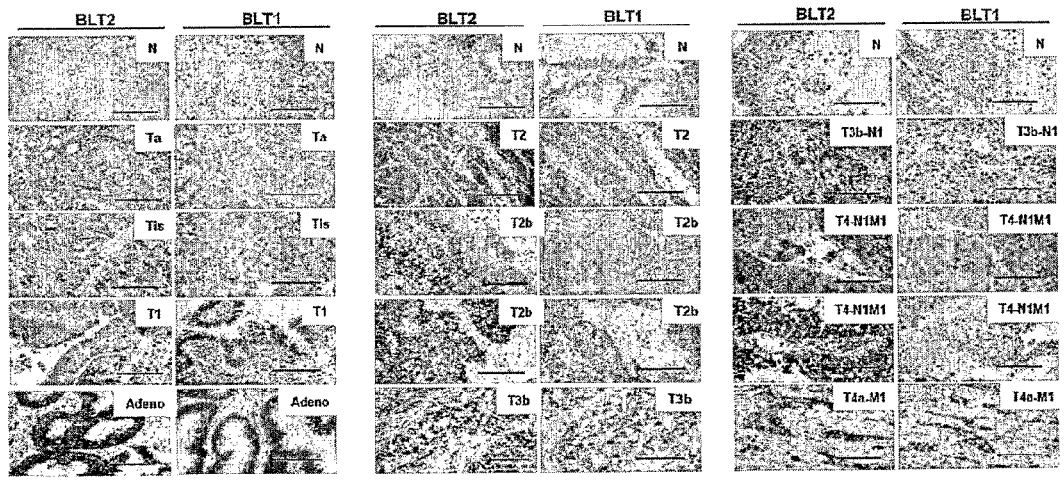
FIG. 4a shows enhanced overexpression of BLT2 in bladder cancer clinical specimens. The expression of BLT2 was Induced in bladder tumor tissue sample: 85 patients.

Immunohistochemical Staining, Histologic Scoring, and Analysis (FIG. 4a)

Various human tumors and corresponding normal tissues/human bladder tumor tissue samples were purchased from Petagen Inc. (Korea). For antigen retrieval, formalin-fixed, paraffin-embedded sections were placed in proteinase K (Biogenex, USA) for 10 min before application of the rabbit polyclonal antibody to BLT1/2 (dilution 1:250) or MMP-9 (dilution 1:250, Sigma-Aldrich, Inc., Saint Louis, Mo.). After incubation with the primary antibody and with the biotinylated secondary antibody, streptavidin-coupled alkaline phosphatase was applied. Fast Red Violet (for BLT1/2 stain; Chemicon, Temecula, Calif., APR150) or Diaminobenzidine (for MMP-9 stain; Chemicon, Temecula, Calif., DAB150) was used as the chromogen. Sections were then counterstained with hematoxylin. Immunoreactivity was independently evaluated by two blinded observers. Cytoplasmic staining was graded for intensity (0-negative, 1-weak, 2-moderate, and 3-strong) and percentage of positive cells [0, 1 (1-24%), 2 (25-49%), 3 (50-74%), and 4 (75-100%)] and discrepancies were resolved by consensus. The grades were then multiplied to determine an H-score (Camp et al., 1999; Ishibashi et al., 2003. The H-scores for tumors with multiple cores were averaged. Protein expression was then defined as low (H-score <130) or high (H-score >130). Chi-square analysis was used to analyze the relationship between BLT2 and MMP-9 expression.

TABLE 1

TMN stage and leukotriene $B_4$ receptors, BLT1 and BLT2, expression levels in bladder tumor tissue sample for 85 patients

| TMN stage | BLT2 groups | | | BLT1 groups | | |
|---|---|---|---|---|---|---|
| (total no.) | 1 | 2 | 3 | 1 | 2 | 3 |
| Stage 0 (18) | 4 (22.2%) | 9 (50%) | 5 (27.8%) | 11 (61.1%) | 7 (38.9%) | 0 (0%) |
| Stage I (28) | 6 (21.4%) | 11 (39.3%) | 11 (39.3%) | 20 (71.4%) | 8 (28.6%) | 0 (0%) |
| Stage II (24) | 0 (0%) | 10 (41.7%) | 10 (41.7%) | 12 (50%) | 8 (33.3%) | 0 (0%) |
| Stage III (13) | 2 (15.4%) | 5 (38.5%) | 6 (46.2%)* | 13 (100%) | 0 (0%) | 0 (0%) |
| Stage IV (6) | 0 (0%) | 0 (0%) | 6 (100%)* | 6 (100%) | 0 (0%) | 0 (0%) |

For consistency of the rating system, BLT1/BLT2 scores were translated as follows "0" and "1+" ="1", "2+"="2", "3+"="3".

Expression patterns in all samples are summarized here. The Pearson chi-square was used for comparisons with normal bladder (p <0.001).

The 85 specimens of bladder tumor were stained anti-BLT1 and anti-BLT2 antibody as shown below.

FIG. 4a shows enhanced expression of BLT2 in bladder tumor tissue of patients. To evaluate expression of BLT2 in various tumors and corresponding neoplastic tissues, immunohistochemical staining (IHC) was carried out using anti-rabbit BLT2 antibody. Various human tumors corresponding normal tissues/human bladder tumor tissue samples were purchased from Petagen Inc. (Korea). Formalin-fixed, paraffin-embedded sections were placed in protenase K (Biogenex, USA) in order to antigen retrieval for 10 min before application of the rabbit polyclonal antibody to BLT1/2 (dilution 1:250). After incubation with the primary antibody, and addition of the biotinylated secondary antibody, streptavidin-coupled alkaline phosphatase was applied. Fast Red Violet (for BLT1/2 stain; Chemicon, Temecula, Calif., APR150) was used as the chromogen. Sections were then counterstained with hematoxylin. The results shown are representative of three independent experiments with similar results. BLT2 expression (red) shows strong cytoplasmic/plasmic membranous staining in various human tumors. Hematoxylin was used for counterstaining (blue). Bar, 100 μm. To examine whether BLTs expression is associated with the pathological potential of tumor, IHC was performed and investigated using scoring analysis. The results shown are representative of three independent experiments with similar results. N, normal bladder tissue; Ta/T is, tumor without invasion; T1, tumors that had invaded the superficial muscle; T2/T2b, tumors with deep muscle invasion; T3b/T3b-N1/T4-N1M1/T4a-M1, tumors that had invaded the perivesical fat or metastasized the lymphatic organs or other adjacent organs (T3b/T3b-N1/T4-N1M1/T4a-M1 are considered as invasive tumors (T3/T4)). Ta/T is, Stage 0; T1, Stage I; T2/T2b, Stage II; T3, Stage III; T3b-N1/T4-N1M1/T4a-M1, Stage IV (according to TNM classifications). Bar, 100 μm. (Bottom) Immunoreactivity was evaluated independently blindly by two observers. Cytoplasmic staining was graded for intensity (0-negative, 1-weak, 2-moderated, and 3-strong) and percentage of positive cells (0, 1 (1-24%), 2 (25-49%), 3 (50-74%), and 4 (75-100%) with discrepancies resolved by consensus and the grades were multiplied to determine an H-score (Camp et al., 1999; Ishibashi et al., 2003. The H-scores for tumors with multiple cores were averaged. Protein expression was then defined as low (H-score <130), or high (H-score >130).

Example 14

Induction of BLT2 in Human Breast Cancer (1) In Situ Hybridization for BLT2 (Panel A of FIG. 4b)

For the preparation of an antisense probe for BLT2 mRNA, the human BLT2 expression plasmid pcDNA3-BLT2 was modified using pcDNA3 vector to prepare pcDNA3-reverse-BLT2, which was confirmed by DNA sequencing. pcDNA3-reverseBLT2 was linearized using Afel restriction endonuclease (MBI Fermentas Ltd), after which the linearized vectors were transcribed using T7 RNA polymerase and DIG (digoxigenin) RNA labeling mix (Roche, Germany). The transcribed probe was ethanol precipitated and quantified by measuring the absorbance at 260 nm. Various breast cancer tissue samples plus matching normal tissue arrays from Petagen Inc. (Korea) were deparaffinized with xylene, after which in situ hybridization was carried out using an in situ hybridization detection kit according to manufacturer's protocol (InnoGenex, San Ramon, Calif., USA). Briefly, deparaffinized tissues were treated with Proteinase K and post-fixed with 1% formaldehyde in RNase-free PBS. After hybridizing the DIG-labeled probes for 16 h at 37° C., they were reacted with anti-DIG antibodies, and BCIP/NBT (bromo-chloro-indolyl-phosphate/nitroblue tetrazolium chloride) reagent was used for color development. Mayer's hematoxylin served as the counter staining. Then, they photographed using a BX51 microscope (Olympus, Tokyo, Japan) equipped with DP71 digital camera (Olympus).

(2) In Situ Hybridization for BLT2 (Panel B of FIG. 4b)

For the preparation of an antisense probe for BLT2 mRNA, the human BLT2 expression plasmid pcDNA3-BLT2 was modified using pcDNA3 vector to prepare pcDNA3-reverse-BLT2, which was confirmed by DNA sequencing. pcDNA3-reverseBLT2 was linearized using Afel restriction endonuclease (MBI Fermentas Ltd), after which the linearized vectors were transcribed using T7 RNA polymerase and DIG (digoxigenin) RNA labeling mix (Roche, Germany). The transcribed probe was ethanol precipitated and quantified by measuring the absorbance at 260 nm. Various cancer tissue samples plus matching normal tissue arrays from Petagen Inc. (Korea) were deparaffinized with xylene, after which in situ hybridization was carried out using an in situ hybridization detection kit according to manufacturer's protocol (InnoGenex, San Ramon, Calif., USA). Briefly, deparaffinized tissues were treated with Proteinase K and post-fixed with 1% formaldehyde in RNase-free PBS. After hybridizing the DIG-labeled probes for 16 h at 37° C., they were reacted with anti-DIG antibodies, and BCIP/NBT (bromo-chloro-indolyl-phosphate/nitroblue tetrazolium chloride) reagent was used for color development. Mayer's hematoxylin served as the counter staining. To examine whether BLTs expression is associated with the pathological potential of tumor, IHC was performed and investigated using Chi-square test. FIG. 4b shows enhanced expression of BLT2 in breast cancer patients.

(3) In Situ Hybridization for BLT2 (FIG. 4c)

For the preparation of an antisense probe for BLT2 mRNA, the human BLT2 expression plasmid pcDNA3-BLT2 was modified using pcDNA3 vector to prepare pcDNA3-reverse-BLT2, which was confirmed by DNA sequencing. pcDNA3-reverseBLT2 was linearized using Afel restriction endonuclease (MBI Fermentas Ltd), after which the linearized vectors were transcribed using T7 RNA polymerase and DIG (digoxigenin) RNA labeling mix (Roche, Germany). The transcribed probe was ethanol precipitated and quantified by measuring the absorbance at 260 nm. Various breast cancer tissue samples plus matching normal tissue arrays from Petagen Inc. (Korea) were deparaffinized with xylene, after which in situ hybridization was carried out using an in situ hybridization detection kit according to manufacturer's protocol (InnoGenex, San Ramon, Calif., USA). Briefly, deparaffinized tissues were treated with Proteinase K and post-fixed with 1% formaldehyde in RNase-free PBS. After hybridizing the DIG-labeled probes for 16 h at 37° C., they were reacted with anti-DIG antibodies, and BCIP/NBT (bromo-chloro-indolyl-phosphate/nitroblue tetrazolium chloride) reagent was used for color development. Mayer's hematoxylin served as the counter staining. To examine whether BLTs expression is associated with the pathological potential of tumor, IHC was performed and investigated using Chi-square test.

Enhanced expression of BLT2 in breast cancer patients was observed (FIG. 4c). Immunoreactivity was evaluated independently blindly by two observers. Cytoplasmic staining was graded for intensity (0-negative, 1-weak, 2-moderated, and 3-strong) and percentage of positive cells (0, 1 (1-24%), 2 (25-49%), 3 (50-74%), and 4 (75-100%) with discrepancies resolved by consensus and the grades were multiplied to determine an H-score (Camp et al., 1999; Ishibashi et al., 2003). The H-scores for tumors with multiple cores were averaged. Protein expression was then defined as low (H-score <130), or high (H-score >130).

Example 15

Figure 4D:
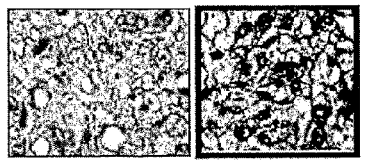
FIG. 4d shows enhanced overexpression of BLT2 in liver, brain, breast, skin, and thyroid cancer clinical specimens. The induced expression of BLT2 was observed in liver, brain, breast, skin, and thyroid tumor tissue.
Figure 4D:
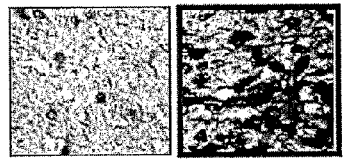
Figure 4D:
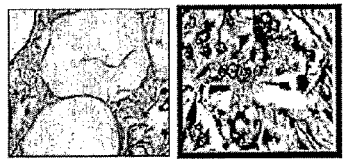
Figure 4D:
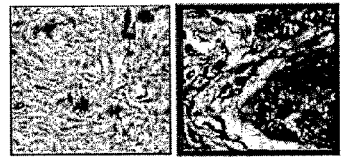
Figure 4D:
Figure 4D:

Induced Expression of BLT2 in Liver, Breast, Skin, and Thyroid Tumor Tissue (1) In Situ Hybridization for BLT2 (FIG. 4d)

For the preparation of an antisense probe for BLT2 mRNA, the human BLT2 expression plasmid pcDNA3-BLT2 was modified using pcDNA3 vector to prepare pcDNA3-reverse-BLT2, which was confirmed by DNA sequencing. pcDNA3-reverseBLT2 was linearized using Afel restriction endonuclease (MBI Fermentas Ltd), after which the linearized vectors were transcribed using T7 RNA polymerase and DIG (digoxigenin) RNA labeling mix (Roche, Germany). The transcribed probe was ethanol precipitated and quantified by measuring the absorbance at 260 nm. Various cancer tissue samples plus matching normal tissue arrays from Petagen Inc. (Korea) were deparaffinized with xylene, after which in situ hybridization was carried out using an in situ hybridization detection kit according to manufacturer's protocol (InnoGenex, San Ramon, Calif., USA). Briefly, deparaffinized tissues were treated with Proteinase K and post-fixed with 1% formaldehyde in RNase-free PBS. After hybridizing the DIG-labeled probes for 16 hr at 37° C., they were reacted with anti-DIG antibodies, and aminoethyl carbazole (AEC) reagent was used for color development. Mayer's hematoxylin served as the counter staining. Then, they photographed using a BX51 microscope (Olympus, Tokyo, Japan) equipped with DP71 digital camera (Olympus). FIG. 4d shows enhanced expression of BLT2 in liver, brain, breast, skin, and thyroid tumor tissue of patients.

Example 16

Figure 5A:
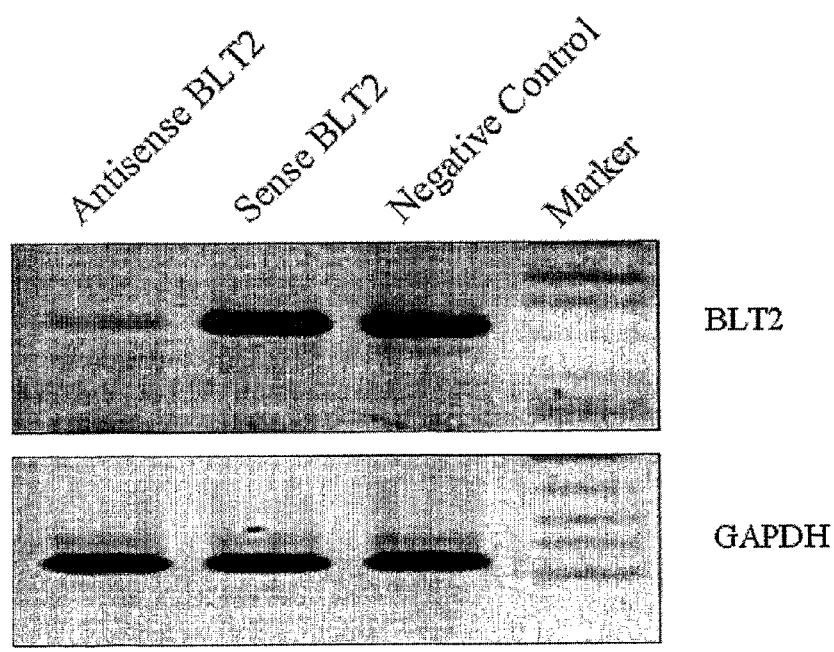
FIG. 5a shows the suppression effect of BLT2 antisense oligonucleotide on BLT2 expression level by RT-PCR.
Figure 5B:
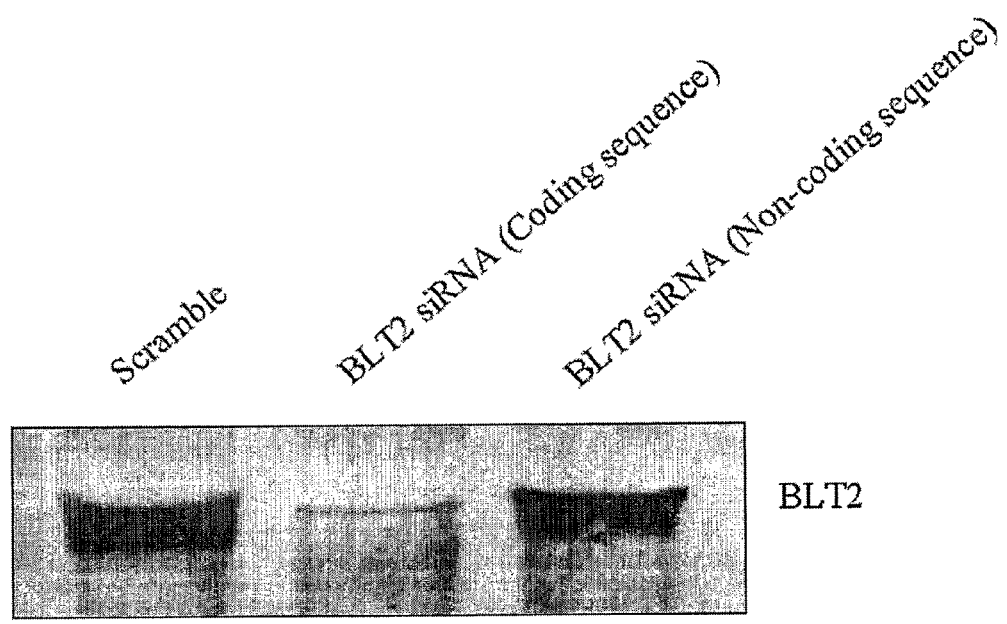
FIG. 5B shows the suppression effect of BLT2 siRNA on BLT2 expression level by Northern blot.

BLT2 Antisense Oligonucleotide Suppression Effect on BLT2 Expression (FIG. 5a)

Suppressed BLT2 expression level was determined by RT-PCR. Rat2-BLT2 stable cells were plated at a density of $5\times10^4$ cells/plate on 6 well plates. After 24 h, cells were transiently transfected with BLT2 specific antisense and sense oligonucleotide plasmid with Lipofectamin reagent and then incubated in fresh
DMEM supplemented with 10% FBS for an additional 24 hr. After additional incubation, the transfected cells were harvested for BLT2 transcripts analysis. Total RNA was reverse-transcribed and PCR amplify were performed with BLT2 forward primer: 5'-tctcatcgggcatcacaggt-3' (SEQ ID NO: 11) and reverse primer: 5'-ccaagctccacaccacgaag-3' (SEQ ID NO: 12). Non-transfected Rat2-BLT2 stable cells cDNA was used the negative control and GAPDH was shown as internal control. The result showed that the level of BLT2 mRNA was reduced by the antisense oligonucleotide, however the level of BLT2 mRNA was not affected by the sense oligonucleotide.

Example 17

BLT2 siRNA Suppression Effect on BLT2 Expression

BLT2 siRNA expression effect on BLT2 expression was addressed by Northern blotting. CHO-BLT2 stable cells were plated at a density of $1\times10^5$ cells/plate on 60-mm dish. After 24 hr, cells were transiently transfected with BLT2 specific siRNA, targeting 1705-1724 bp in NM_019839; 5'-GAAG-GATGTCGGTCTGCTA-3' (SEQ ID NO: 22), with oligofectamin reagent and then incubated in fresh RPMI 1640 supplemented with 10% FBS for an additional 24 h. after additional incubation, total RNA was performed Northern blot with [$^{32}$P]-dCTP labled BLT2 probe. Scramble RNA and non-coding sequence BLT2 siRNA were used the negative control. A 110 bp PCR fragment was amplified with pcDNA3.1-BLT2 clone using the following two primers, forward primer: 5'-cttctcatcgggcatcacag-3' (SEQ ID NO: 23) and reverse primer: 5'-atccttctgggcctacaggt-3' (SEQ ID NO: 24). This probe was located mainly in the BLT2 coding region. Total RNA was extracted with TRIzol reagent and then loaded the ten microgram total RNA for 2 h in MOPS containing agarose gel. After this step, the total RNA was transferred the Hybond N$^+$ membrane for overnight with 20×SSC buffer. The membrane was hybridized with [$^{32}$P]-dCTP labled BLT2 probe in the hybridization buffer for 18 h at 68° C. And then, washed in 0.1×SSC (0.1% SDS) for 1 h at 68° C. and subjected to autoradiography. The result showed that the level of BLT2 mRNA was reduced by the BLT2 siRNA (coding sequence), however the level of BLT2 mRNA was not affected by the BLT2 siRNA (non-coding sequence).

Example 18

Figure 6:
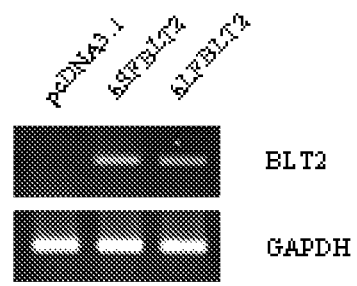
FIGS. 6a and 6b depict similar expression levels of LF-BLT2 or SF-BLT2 when transfected in CHO cells.
Figure 6:
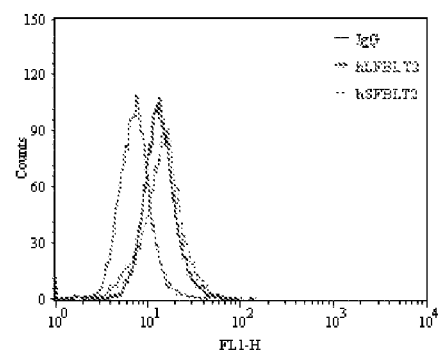
Figure 7:
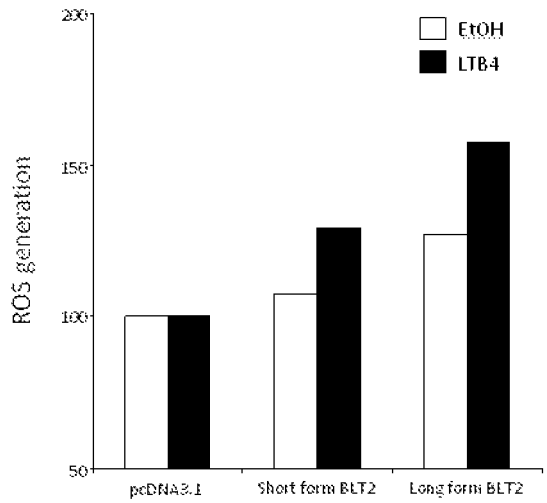
FIGS. 7a and 7b depict that LF-BLT2 is more active in mediating chemotactic signaling and motility in CHO cells compared to SF-BLT2.
Figure 7:
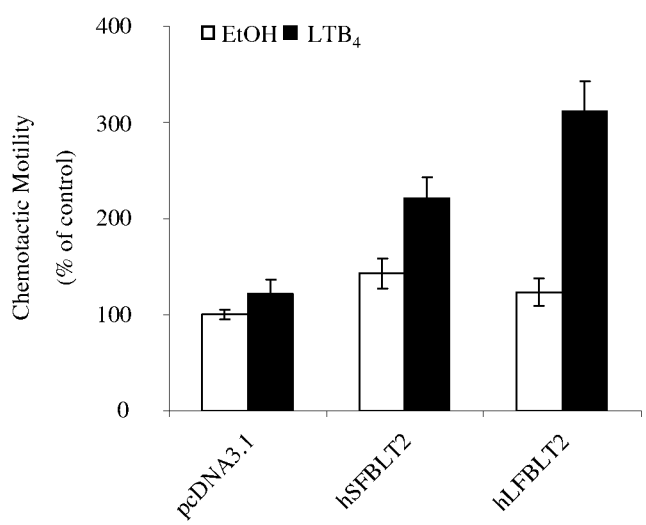
Figure 8:
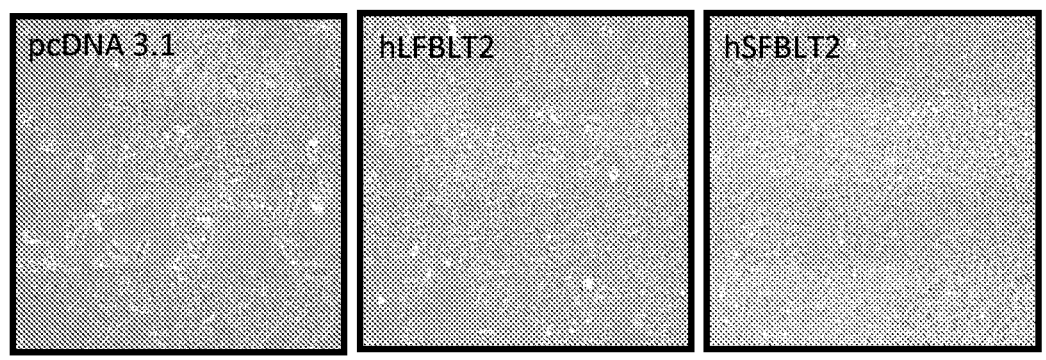
FIGS. 8a and 8b depict that growth and ERK activity were enhanced by LF-BLT2 compared to SF-BLT2.
Figure 8:
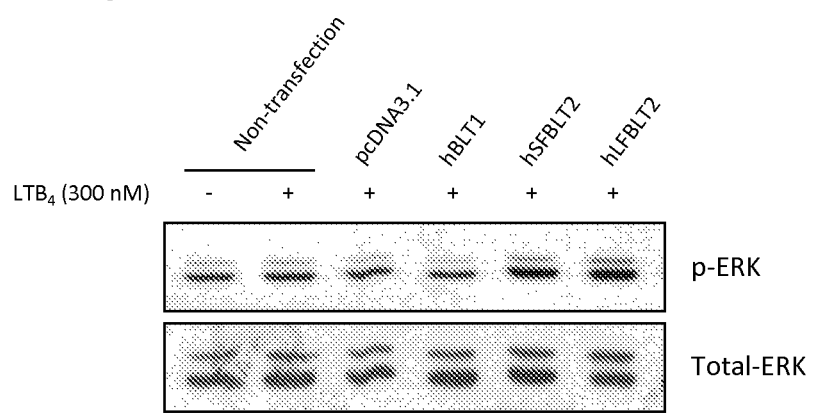

Long form BLT2 is Involved in Chemotactic Signaling, Chemotactic Motility, Cell Growth, ERK Activation, and Cancer Invasive Activity To investigate the roles of long form BLT2 (LF-BLT2) and short form BLT2 (SF-BLT2), experiments were performed to examine their properties. In CHO cells transfected with LF-BLT2 and SF-BLT2 expression constructs (2 µg DNA), levels of mRNA expression were similar as determined by RT-PCR assay using GAPDH transcript levels as a control (FIG. 6a). The RT-PCR was performed under the following conditions: BLT2: lab primer (melting temperature 69° C.) for 30 cycles and GAPDH (melting temperature 58° C.) for 22 cycles. Additionally, FACS analysis of the CHO cells transfected with LF-BLT2 and SF-BLT2 expression constructs indicated similar levels of protein expression (FIG. 6b). FACS was performed under the using non-permeabilization, anti-HA antibody (Roche), and anti-mouse FITC antibody.
CHO cells transfected with LF-BLT2 and SF-BLT2 expression constructs were examined for reactive oxygen species (ROS) generation and chemotactic motility in the presence of LTB$_4$. LF-BLT2 showed a significantly enhanced ROS generation in the presence of LTB4 compared to SF-BLT2 (~25% more ROS generation; FIG. 7a). LF-BLT2 also showed a significantly enhanced chemotactic migration in the presence of LTB4 compared to SF-BLT2 (~30% more chemotactic mobility; FIG. 7b). Thus, LF-BLT2 was observed to be more active or efficient than SF-BLT2 in mediating chemotactic signaling and motility. Rat-2 cells transfected with LF-BLT2 and SF-BLT2 were examined for growth and proliferation and ERK activity in the presence of LTB$_4$. SF-BLT2 transfected cells showed about the same growth as LF-BLT2 transfected cells, but, in the presence of LTB$_4$, significantly enhanced growth was observed by LF-BLT2 compared to SF-BLT2 (FIG. 8a). SF-BLT2 transfected cells showed about the same ERK activity as LF-BLT2, but, in the presence of LTB4, a significantly enhanced ERK activation was observed by LF-BLT2 compared to SF-BLT2 (FIG. 8b).
To examine the roles of long form BLT2 (LF-BLT2) and short form BLT2 (SF-BLT2) in cancer, a role for BLT2 in invasion-enhancing activity in CAOV-3 cells (ovarian cancer cells) was analyzed. Long form BLT2 on invasion activity was testing by transfection with a BLT2 expression construct. Cells were transfected with pcDNA3.1-LFBLT2 or pcDNA3.1-SFBLT2 and incubated with 10% FBS medium for 24 hr, and the loaded into the upper wells of BD Bio-Coat™ Matrigel™ Invasion Chambers (BD Biosciences, San Jose, Calif.) according to the manufacturer's instructions. Complete medium containing 10% FBS was added to the lower chamber and 0.5% FBS medium added on top, and plates were incubated at 37° C. for 48 hr. The filters were fixed in methanol and stained with hematoxylin and eosin (H&E). After removal of the contents of the upper membrane surface, invasive cells were counted microscopically in 5 random high-power fields per filter; each sample was assayed in duplicate, and 5 independent assays were performed. Data are expressed as the mean relative to transfection with pcDNA3.1 cells (control).
For quantitative and real-time PCR analysis, total cellular RNA was extracted from cells using Easy-Blue from Intron Co. (Daejeon, Korea). First-strand cDNA was prepared in buffer containing 0.5 µg of oligo (dT)$_{15}$ primer, 10 mM dithiothreitol, 0.5 mM dNTP mix (TaKaRa), and 200 units of M-MLV Reverse Transcriptase and incubated at 37° C. for 50 min. The primer sequences used are as follows: human BLT1 (forward, 5'-TATGTCTGCGGAGTCAGCATGTACGC-3' (SEQ ID NO: 13); reverse, 5'-CCTGTAGCCGACGC-CCTATGT CCG-3' (SEQ ID NO: 14)); human BLT2 (forward, 5'-AGCCTGGAGACTCTGACCGCTTTCG-3'(SEQ ID NO: 9); reverse, 5'-GACGT AGCACCGGGT-TGACGCTA-3' (SEQ ID NO: 10)); human NOX4 (forward, 5'-CTCAGCGGAATCAATCAGCTGTG-3' (SEQ ID NO: 25); reverse, 5'-AGAGGAACACGACAATCAGCCTTAG-3' (SEQ ID NO: 26)); human MMP-2 (forward, 5'-GCTCA-GATCCGTGGTGAGAT-3' (SEQ ID NO: 27); reverse, 5'-GGTGCTGGCTGAGTAGATCC-3' (SEQ ID NO: 28)); and GAPDH (forward, 5'-CTGCACCACCAACTGCT-TAGC-3' (SEQ ID NO: 29); reverse, 5'-CTTCACCACCT-TCTTGATGTC-3' (SEQ ID NO: 30)). PCR products were purified by 1.5% agarose gel electrophoresis and visualised with ethidium bromide.

For Western blotting analysis, cells were washed with cold PBS and scraped into lysis buffer [20 mM Tris-HCl (pH 7.5), 150 mM NaCl, 0.5% NP-40, 5 mM EDTA, 1% Triton X-100 and protease inhibitors] at 4° C. Harvested protein samples were heated at 95° C. for 5 min for loading onto acrylamide gels, and subjected to SDS-PAGE, followed by transfer to polyvinylidene difluoride (PVDF) membranes for 90 min at 100 V. The membranes were blocked for 1 hr with Tris-buffered saline (TBS) containing 0.05% (vol/vol) Tween 20 plus 5% (wt/vol) nonfat dry milk and then incubated with the appropriate antibodies. pSTAT-3 (Y705, S727) antibodies were obtained from Cell Signaling Technology (Danvers, Mass.) (pSTAT3, 1:2000 dilution; α-tubulin, 1:4000 dilution). Primary antibodies in 5% nonfat milk overnight at 4° C. The membrane-bound protein-antibody complexes were then incubated for 2 hr with horseradish peroxidise (HRP)-conjugated secondary antibody before development with an enhanced chemiluminescence kit (Amersham Biosciences, UK).

Figure 9:
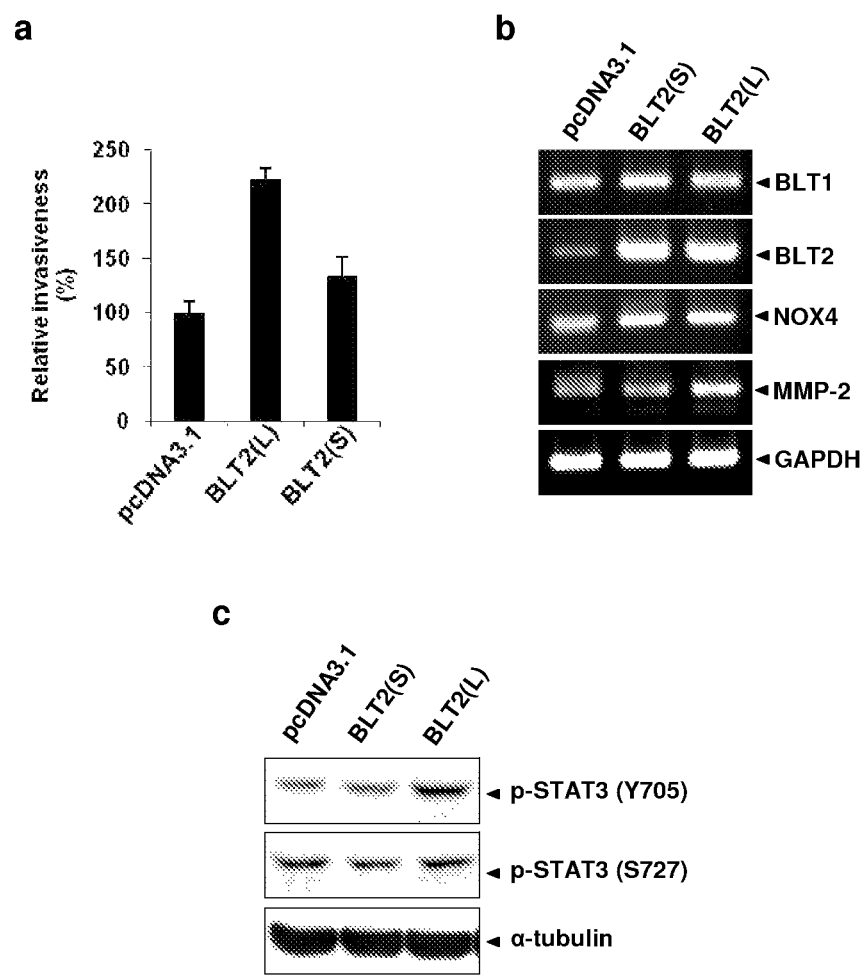
FIGS. 9a-9c show that BLT2 signalling is involved in invasion phenotype of CAOV-3 cells.

The results from the studies were consistent with a role for BLT2 in the invasive activity of CAOV-3 cells. In cell invasion assays, BLT2 expression enhanced invasiveness of CAOV-3 cells (FIG. 9a). The cells were harvested for detection of BLT1, BLT2, NOX4 and MMP-2 transcripts by semiquantitative RT-PCR with specific primers. BLT2 overexpression induced NOX4 and MMP-2 mRNA levels (FIG. 9b). p-STAT3 activated by transient expression of BLT2 in CAOV-3 cells. Cells were transiently transfected with 1 μg of pcDNA3.1-LFBLT2 or pcDNA3.1-SFBLT2, and levels of p-STAT3 (Y705, S727) were detected by Western blot analysis. Transiently transfected LF-BLT2 cells showed increased levels of phospho-STAT3 (FIG. 9c). Thus, the results show that upregulation of MMP-2 and phosphorylation of STAT-3 (Y705), a key transcription factor associated with invasion of CAOV-3 cancer cells, were highly induced by transient transfection with long form BLT2 plasmid, and not by short form BLT2 plasmid. MMP-2 upregulation is well-known as an invasion-associated MMP phenotype in ovarian cancer cells.

Example 12

Generation of Anti-Long Form BLT2 Antibody having BLT2 Neutralizing Activity

To study long form BLT2, a long form BLT2 antibody was generated using a 14-mer peptide present on long form BLT2 (PTPERPLWRLPPTC; peptide Ab-1; N-terminal sequences 14-27 amino acid residues), and not short form BLT2. Mice were immunized intraperitoneally with peptide Ab-1 (PT-PERPLWRLPPTC) conjugated to BSA (peptide 2.0; 100 μg/CFA/head). Mice were immunized every 3 weeks. Four days after the last booster, mice were sacrificed and spleen cells were collected.

Spleen cells were fused with SP2 cells (American Type Culture Collection) by using PEG 4000 (Boehringer) at a 1:1 ratio. The PEG mediated fusion were performed according to the procedures previously described by Harlow and Lane (Harlow, E.; Lane, D., Eds.; Antibodies, a laboratory manual; Cold Spring Harbor Laboratory: New York, 1988; pp 139-243). Fused cells were distributed over 96 well tissue culture plates at 2,000 cells per well in complete DMEM medium containing 100 μM hypoxanthine, 0.4 μM aminopterin, and 16 μM thymidine (HAT; sigma). Medium was replaced weekly.

For the identification of antigen-reacting mAbs, ELISA-based screening was performed. Briefly, microtiter plates were coated at 4° C. overnight with 100 μl per well of peptide Ab-1 conjugated with BSA (peptide 2.0; 10 μg/ml) diluted in PBS. Plates were blocked with blocking buffer (PBS containing 1% BSA (Sigma) and 0.05% Tween 20 (Sigma)) for 1 hr at room temperature. Hybridoma supernatant (100 μl per well) was transferred into the ELISA plates. Binding reaction was carried out at room temperature for 2 h. Subsequently, plates were washed four times with washing buffer (PBS containing 0.05% Tween 20 (Sigma)), and 100 μl of HRP-conjugated goat anti-human Fab (Sigma) diluted 1:10,000 in binding buffer (PBS containing 1% BSA (Sigma)) was added, and reactions were carried out at room temperature for 1 hr. Finally, plates were washed four times, and 100 μl of TMB substrate (Kirkegaard & Perry Laboratories) per well was added. The absorbance was determined at 490 nm.

To analyze the level of BLT2 expression, 253J-BV bladder cancer cells were fixed with 3% paraformaldehyde and permeabilized with 0.1% Triton X-100 in PBS. After being blocked with 2% BSA for 30 min, cells were incubated with the primary BLT2 antibody. Cells were then washed 3 times with PBS and incubated with FITC-conjugated anti-rabbit IgG (Invitrogen, Carlsbad, Calif.). Cells (10,000 per sample) were then analyzed with a flow cytometer (FACSCalibur™) using Cell Quest software, as described previously. Data are expressed as the mean fluorescence intensity. The FACS results shown in FIG. 10a are representative of three independent experiments with similar results.

Of 22 potential candidates, FACS analysis indicated at least 6 LF-BLT2-recognizing positive antibodies were obtained (FIG. 10b). Positive antibodies included: BLT2-LF-38 (#9 in FIG. 10b), BLT2-LF-45 (#10 in FIG. 10b) BLT2-LF-62-5 (#19 in FIG. 10b), BLT2-LF-26-22 (#20 in FIG. 10b), BLT2-LF-20 (#21 in FIG. 10b), BLT2-LF-12-3 (#22 in FIG. 10b). In addition to using or characterizing the 6 positive antibodies, antibody BLT2-LF-13 (#4 in FIG. 10b) which did not recognize LF-BLT2 was used as a negative control.

To test whether anti-LF-BLT2 antibodies have selective inhibitory activity of BLT2 function and, thus, BLT2 neutralizing activity, the effect of anti-LF-BLT2 antibody on the chemotaxis property of stably expressing BLT2 CHO cells, BLT2 transiently transfected CHO cells, and BLT1 transiently transfected CHO cells was examined. BLT2 expressing cells were prepared and maintained in the media with 0.5 mg/mL G418. Transiently transfected CHO cells (CHO-vector, CHO-BLT1, and CHO-BLT2) were transfected with pcDNA3.1, pcDNA3.1-long form BLT2 or pcDNA3.1-BLT1 plasmid. Chemotactic motility was assayed using Transwell chambers with 6.5-mm-diameter polycarbonate filters (8-μm pore size, Corning Costar), as previously described. Briefly, the lower surfaces of the filters were coated with 10 μg/mL fibronectin in serum-free RPMI 1640 medium for 1 hr at 37°

C. Dry, coated filters containing various amounts of $LTB_4$ were placed in the lower wells of the Transwell chambers, after which 100 μL of CHO cells stably expressing BLT2 or transiently expressing BLT1 and BLT2 in serum-free RPMI 1640 were loaded into the top wells, yielding a final concentration of $2.5 \times 10^4$ cells/mL. When assessing the effects of inhibitors, cells were pretreated with the respective inhibitor for 30 min before seeding. After incubation at 37° C. in 5% $CO_2$ for 3 hr, the filters were fixed for 3 min with methanol and stained for 10 min with hematoxylin and eosin. Chemotaxis was quantified by counting the cells on the lower side of the filter under an optical microscope (magnification, ×200). Six fields were counted in each assay; each sample was assayed in duplicate; and the assays were repeated twice.

Figure 11:
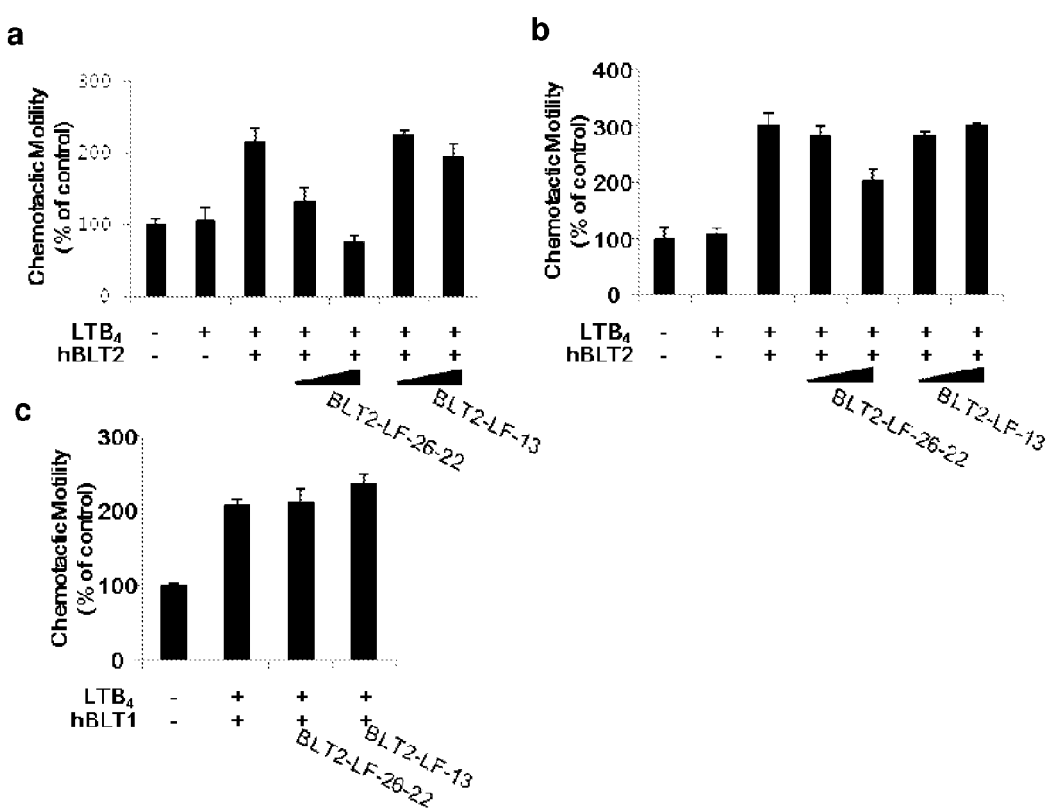
FIGS. 11a-11c are graphs depicting chemotaxis analysis using generated anti-LF BLT2 antibody.

Chemotactic migration was dramatically inhibited by anti-LF-BLT2 antibody (BLT2-LF-26-22; #20 in FIG. 10b) in both CHO-BLT2 stable cells and BLT2-transiently transfected CHO cells (FIG. 11a), but no inhibitory effect by control antibody (BLT2-LF-13) (#4 in FIG. 10b) was detected (FIG. 11b). However, BLT2 neutralizing antibody did not show any inhibitory effect on the chemotactic migration caused by BLT1 transfected CHO cells (FIG. 11c), indicating that the inhibitory effect of anti-LF-BLT2-#26-22 (#20 in FIG. 10b) was specific to BLT2. Thus, anti-LF-BLT2 antibody display neutralizing activity specific for BLT2.

Example 12

Anti-cancer Activities of Anti-long Form BLT2 Neutralizing Antibody

Figure 12:
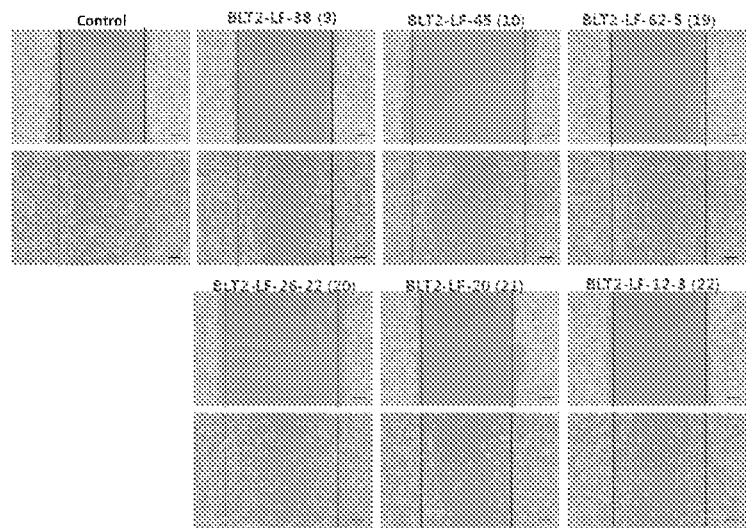
FIG. 12 depicts images showing that blockade of BLT2 by neutralizing antibody inhibited 253J-BV cell migration. Cells were grown to confluence in 24-well plates. Cells were wounded with a pipette tip, and treated with anti-BLT2-neutralizing antibody (BLT2-LF-38, 20 µg/ml; BLT2-LF-45, 20 µg/ml; BLT2-LF-62-5, 20 µg/ml; BLT2-LF-26-22, 20 µg/ml; BLT2-LF-20, 20 µg/ml; and BLT2-LF-12-3, 20 µg/ml). Cells were examined by light microscopy prior to addition of experimental treatments (0 h; upper panels) and at 48 h after treatment (lower panels). Bar represents 100 µm.

LF-BLT2 IgG Ab were tested to determine if they had anti-BLT2-neutralizing effect in a wound healing assay of cancer cells. 253J-BV cells ($2.5 \times 10^5$) were seeded into 24-well plates. When cells reached confluence, a wound was made in the center of each well using a 1000-μl pipette tip. The cells were treated with anti-BLT2-neutralizing antibody (20 μg/ml in 0.5% FBS RPMI medium). Cells were examined by light microscopy prior to addition of experimental treatments at 0 hr (FIG. 12, top panels) and at 48 h (FIG. 12, bottom panels) after treatment. At 48 h after wound formation, cells were washed with PBS, fixed in 100% methanol and images of each wound well were captured on a BX51 microscope (Olympus, Tokyo, Japan) equipped with a DP71 digital camera (Olympus).

Blockade of BLT2 by neutralizing antibody inhibited 253J-BV cell migration. Thus, anti-long form BLT2-neutralizing antibody showed potent inhibitory activities on wound healing phenotype of cancer cells. When wounded 253J-BV bladder cancer cells were treated with various anti-LF-BLT2 neutralizing antibodies (20 μg/ml), wound healing migration motility was significantly diminished compared to control antibody treated cells. In particular, BLT2-LF-45 (#10 in FIG. 10b), BLT2-LF-26-22 (#20 in FIG. 10b) and BLT2-LF-20 (#21 in FIG. 10b) antibodies show more potent inhibitory activity compared to the other antibodies assayed. The negative control antibody (BLT2-LF-13; #4 in FIG. 10b) did not show any anti-migration activity (data now shown). Thus, anti-LF-BLT2 neutralizing antibody treatment inhibited 253J-BV cell migration in a wound healing assay.

LF-BLT2 IgG Ab were also tested to determine if they had anti-BLT2-neutralizing effect in a cancer cell invasion assay. The migration of MDA-MB-231 breast cancer cells through Matrigel matrix gel in the presence of anti-LF-BLT2 was examined. The upper chamber of transwells (8.0-μm membrane pores; Costar) were coated with 2.5 μg/ml Matrigel matrix gel (BD Biosciences) and incubated at 37° C. for 2 hr. A total of $5 \times 10^4$ cells in 100 μl of medium with 0.5% FBS were added to the upper chamber and allowed to migrate toward the bottom chamber, which contained medium with 10% FBS as a chemoattractant. MDA-MB-231 cells were stopped at 48 hr. Cells on the top surface of the membranes were removed using a cotton swab, and cells on the underside were fixed in methanol and stained with hematoxylin and eosin (H&E).

Figure 13:
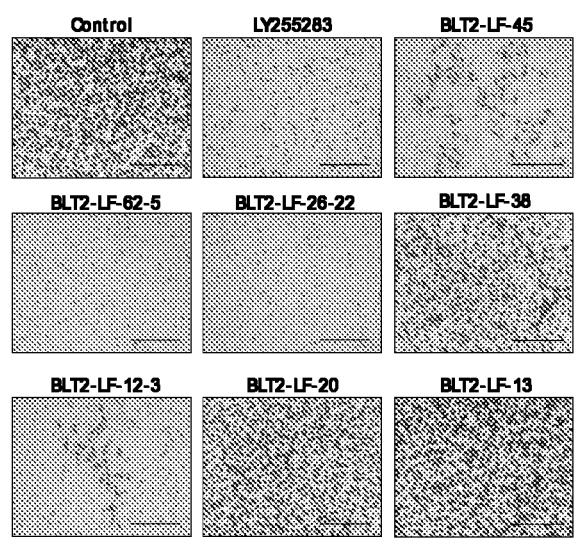
FIG. 13 BLT2 (long form) neutralizing antibody treatment reduced the invasiveness of MDA-MB-231 breast cancer cells. MDA-MB-231 cells were pre-treated with LY255283 (10 µM) and BLT2 (long form) neutralizing antibodies (BLT2-LF-38, 20 µg/ml; BLT2-LF-45, 20 µg/ml; BLT2-LF-62-5, 20 µg/ml; BLT2-LF-26-22, 20 µg/ml; BLT2-LF-20, 20 µg/ml; and BLT2-LF-12-3, 20 µg/ml) for 1 hr before the invasion assays. After 48 h, cells were assayed for invasiveness and photographed. Scale bar, 200 µm.

Anti-LF-BLT2-neutralizing antibodies showed potent inhibitory activity on the invasion phenotype of breast cancer cells. When MDA-MB 231 breast cancer cells were treated with anti-LF (long form)-BLT2 neutralizing antibody (20 μg/ml), invasion activity was significantly diminished compared to control antibody treated cells (FIG. 13). As a positive control, LY255283 (a potent BLT2 inhibitor; antagonist) was tested and showed inhibitory activity. As a negative control, BLT2-LF-13 (#4 in FIG. 10b), an antibody that did not recognize LF-BLT2, did not show any inhibitory activity, as expected. In particular, BLT2-LF-45 (#10 in FIG. 10b), BLT2-LF-62-5 (#19 in FIG. 10b), BLT2-LF-26-22 (#20 in FIG. 10b), and BLT2-LF-12-3 (#22 in FIG. 10b) showed potent anti-invasion activities. Other antibodies including BLT2-LF-20 (#21 in FIG. 10b) and BLT2-LF-38 (#9 in FIG. 10b) did not show any anti-invasion activity, indicating that not all the positive BLT2-recognizing antibodies show anti-BLT2 activity. Thus, anti-LF-BLT2 neutralizing antibody treatment reduced the invasiveness of MDA-MB-231 breast cancer cells.

As disclosed above, the invention makes use of BLT2 inhibitors for (1) inducing apoptosis of cancer cells, (2) suppressing metastatic potential of cancer cells, (3) blocking angiogenesis of cancer cells. Also, this invention include (4) a novel strategy for screeing BLT2 signaling inhibitors by measuring the cell growth of Rat2-BLT2 stable cells. Lastly, this invention includes (5) the novel observation of BLT2 overexpression in various human cancers, which is an important phenomenon in tumorigenesis. Thus, the invention claims the use of strategies targeting against BLT2 verexpression or over-activation as a tool for developing therapeutic composition against human cancer.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991).

All patents and publications mentioned in this specification are herein incorporated by reference to the same extent as if each independent patent and publication was specifically and individually indicated to be incorporated by reference.

REFERENCES

The following documents are cited herein.
1. Samuelsson, B.; Dahlen, S. E.; Lindgren, J. A.; Rouzer, C. A.; Serhan, C. N. Leukotrienes and lipoxins: structures, biosynthesis, and biological effects. Science 237:1171-1176; 1987.
2. Yokomizo, T.; Kato, K.; Terawaki, K.; Izumi, T.; Shimizu, T. A Second Leukotriene $B_4$ Receptor, 'BLT2: A New Therapeutic Target in Inflammation and Immunological Disorders. J. Exp. Med. 192:421-432; 2000.
3. Choi J A, Kim E Y, Song H W, Kim C M, and Kim J H. "ROS are generated through a BLT2-linked cascade in Ras-transformed cells" (2008) Free Radical Biol & Med, AA, 624-634.
4. Woo, C. H.; You, H. J.; Cho, S. H.; Eom, Y. W; Chun, J. S.; Yoo, Y. J.; Kim, J. H. Leukotriene B(4) stimulates Rac-ERK cascade to generate reactive oxygen species that mediates chemotaxis. J. Biol. Chem. 277:8572-8578; 2002.
5. Yokomizo, T.; Izumi, T; Chang, K.; Takuwa, Y; Shimizu, T. A. G-protein-coupled receptor for leukotriene $B_4$ that mediates chemotaxis. Nature 387:620-624; 1997.
6. Chen, X. S.; Sheller, J. R.; Johnson, E. N.; Funk, C. D. Role of leukotrienes revealed by targeted disruption of the 5-lipoxygenase gene. Nature 372:179-182; 1994.
7. Griffiths, R. J.; Pettipher, E. R.; Koch, K.; Farrell, C. A.; Breslow, R.; Conklyn, M. J.; Smith, M. A.; Hackman, B. C; Wimberly, D. J.; Milici, A. J. Leukotriene $B_4$ plays a critical role in the progression of collagen-induced arthritis. Proc. Natl. Acad. ScL USA 92:517-521; 1995.
8. Turner, C. R.; Breslow, R.; Conklyn, M. J.; Andresen, C. J.; Patterson, D. K.; Lopez-Anaya, A.; Owens, B.; Lee, P.; Watson, J. W.; Showell, H. J. In vitro and in vivo effects of leukotriene $B_4$ antagonism in a primate model of asthma. J. Clin. Invest. 97:381-387; 1996.
9. Kamohara, M.; Takasaki, J.; Matsumoto, M.; Saito, T; Ohishi, Y; Ishii, H. M.; Furuichi, K. Molecular cloning and characterization of another leukotriene $B_4$ receptor. J. Biol. Chem. 275:27000-27004; 2000.
10. Blaine, S. A.; Wick, M.; Dessev, C; Nemenoff, R. A. Induction of $cPLA_2$ in lung epithelial cells and non-small cell lung cancer is mediated by SpI and c-Jun. J. Biol. Chem. 276:42737-42743; 2001.
11. Heasley, L. E.; Thaler, S.; Nicks, M.; Price, B.; Skorecki, K.; Nemenoff, R. A. Induction of cytosolic phospholipase $A_2$ by oncogenic Ras in human non-small cell lung cancer. J. Biol. Chem. 272:14501-14504; 1997.
12. Gupta, S.; Srivastava, M.; Ahmad, N.; Sakamoto, K.; Bostwick, D. G.; Mukhtar, H. Lipoxygenase-5 is overexpressed in prostate adenocarcinoma. Cancer 91:737-743; 2001.
13. Hennig, R.; Ding, X. Z.; Tong, W. G; Schneider, M. B.; Standop, J.; Friess, H.; Buchler, M. W.; Pour, P. M.; Adrian, T. E. 5-Lipoxygenase and leukotriene B(4) receptor are expressed in human pancreatic cancers but not in pancreatic ducts in normal tissue. Am. J. Pathol. 161:421-428; 2002.
14. Jiang, W. G; Douglas-Jones, A.; Mansel, R. E. Levels of expression of lipoxygenases and cyclooxygenase-2 in human breast cancer. Prostaglandins Leuko. Essent. Fatty Acids 69:275-281; 2003.
15. Matsuyama, M.; Yoshimura, R.; Mitsuhashi, M.; Hase, T.; Tsuchida, K.; Tkemoto, Y.; Kawahito, Y.; Sano, H.; Nakatani, T. Expression of lipoxygenase in human prostate cancer and growth reduction by its inhibitors. Int. J. Oncol. 24:821-827; 2004.
16. Ding, X. Z.; Talamonti, M. S.; Bell, R. H.; Adrian, T. E. A novel anti-pancreatic cancer agent, LY2931U. Anticancer Drugs 16:467-473; 2005.
17. Tong, W. G; Ding, X. Z.; Hennig, R.; Witt, R. C; Standop, J.; Pour, P. M.; Adrian, T. E. Leukotriene $B_4$ receptor antagonist LY293111 inhibits proliferation and induces apoptosis in human pancreatic cancer cells. CHn. Cancer Res. 8:3232-3242; 2002

---

What is claimed is:

1. A method of treating cancer in a patient, the method comprising administering to the patient a therapeutically effective amount of an agent that inhibits the intracellular signaling of long-form BLT2, wherein the agent is an antibody or fragment thereof that specifically binds long-form BLT-2, in the region set forth by amino acids 1-31 of SEQ ID NO: 3.

2. The method of claim 1, wherein the agent selectively reduces the intracellular signaling of long-form BLT2 to the patient while the intracellular signaling of short-form BLT2 is not disrupted.

3. The method of claim 1, wherein the antibody or fragment thereof specifically binds long-form BLT-2 in the region set forth by amino acids 14-27 of SEQ ID NO: 3.

4. The method of claim 1, wherein the antibody is a polyclonal or monoclonal antibody.

5. A method of reducing activity of long-form BLT2 in a cancer cell, the method comprising contacting the cancer cell with an effective amount of an agent that inhibits the intracellular signaling of long-form BLT2, wherein the agent is an antibody or fragment thereof that specifically binds long-form BLT-2, in the region set forth by amino acids 1-31 of SEQ ID NO: 3.

6. The method of claim 5, wherein the antibody or fragment thereof specifically binds long-form BLT-2 in the region set forth by amino acids 14-27 of SEQ ID NO: 3.

7. The method of claim 5, wherein the antibody is a polyclonal or monoclonal antibody.

* * * * *

SEQUENCE LISTING

```
<160> NUMBER OF SEQ ID NOS: 30

<210> SEQ ID NO 1
<211> LENGTH: 2798
<212> TYPE: DNA
<213> ORGANISM: homo sapiens

<400> SEQUENCE: 1
aaactggccc tggccctgaa ccaaatacct tgaaccctcg taaactccat accctgaccc      60
ccttgttttg gatataccca ggtagaacaa ctctctctca ctgtctgttg tgaggatacg     120
ctgtagccca ctcattaagt acattctcct aataaatgct ttggactgat caccctgcca     180
gtcttttgtc ttgggcaatc tatacttttc tcagaggttc ccaaggccta ctgaagggac     240
ttaacatact cttaatggct ttcctctctc ttgtttacc  ttatgccctc acttcctgag     300
ttaacctccc aaatacagga tcacctgtac ccaagccctt agctcaagaa tacaggatca     360
cctgtaccca agcccttagc tcaagctctg ctttggaaga acccaaacta agacagtgct     420
cctggtgccc tccccaagca acctcaagtt ctggctgtta cttgagcaga ggcctttctt     480
ttcccttccc ccagctctat ccatctgcca ggcccccctc aaatctcttc atttccaagt     540
```

```
tttgcttgac ttttccaaga ggagagggct gcttcttagt atgtccctac tcatcctttc    600
ctttcttgtc ttgtatcctg gtgcagcctg gtaatgggc ctcttcatgg ttgtgtgtca    660
tgactcccta accattatgc ctccatgcat cccctgttcc tcctggaacc tagcaccatg    720
ccttacatgg aaaagctgtc attgacagcc cggtgagagc cctgagggtg gagtgactgg    780
ggcagggcct gaggcaagag gtgggaggag gtaggaggcc aggggctcag ccggaccagg    840
agactggaaa caggcaagga taaggcaggt ggggactga gttgtttggg tcacctctgc    900
aggccagaga gaccaggcaa catacacact gcagaaggtg ggctgggagg attggggcca    960
gagctggggg agggatgaga acagaagcag gaccaggatt cagcagagtc ctcctatttc   1020
cttccaccac cagggaatct tactgcccca cttcagcttg tgctgttttcc tggcaaggca   1080
ggctctcaca tgcctggacg cctgggtgcg ttggtgatgg aaggagcag ggtgagggag    1140
gggcccagg agaggcccag gatgagcctc atcttgtccc tccccattct tgtcttaccc    1200
tctgcaaatg tgataggcac aggacaggag taggcacctc gcctactgct gcttaacctt   1260
tcagcttctc caggccccca atcctgcttg ctcccagctt ggtaagtaga tctgtgcacg   1320
tcccttttaca ccccaccatc cagttttgcc cagatgtgct agaatggggc tggacaaaga   1380
aggagggggcc agactagagg agtggtggta gagatagtga cagcctgggg tgaggacttt   1440
atgcctgttt accactgagc tctgggaagg aggccaggag tggggcaggt caactgactg   1500
ggagcagggg atctgggttc caagaaggag ttgtgtttga ggtggggtct gggtcctcgt   1560
ggaagtcagg actcccaggc agaaaagagg caggctgcag ggaagtaagg aggaggcatg   1620
gcaccttctc atcgggcatc acaggtgggg ttttgcccca cccctgaacg ccctctgtgg   1680
cgccttccac ccacctgtag gcccagaagg atgtcggtct gctaccgtcc cccagggaac   1740
gagacactgc tgagctggaa gacttcgcgg gccacaggca cagccttcct gctgctggcg   1800
gcgctgctgg ggctgcctgg caacggcttc gtggtgtgga gcttggcggg ctggcggcct   1860
gcacggggggc gaccgctggc ggccacgctt gtgctgcacc tggcgctggc cgacggcgcg   1920
gtgctgctgc tcacgccgct cttttgtggcc ttcctgaccc ggcaggcctg gccgctgggc   1980
caggcgggct gcaaggcggt gtactacgtg tgcgcgctca gcatgtacgc cagcgtgctg   2040
ctcaccggcc tgctcagcct gcagcgctgc ctcgcagtca cccgccccctt cctggcgcct   2100
cggctgcgca gcccggccct ggcccgccgc ctgctgctgg cggtctggct ggccgccctg   2160
ttgctcgccg tcccggccgc cgtctaccgc cacctgtgga gggaccgcgt atgccagctg   2220
tgccacccgt cgccggtcca cgccgccgcc cacctgagcc tggagactct gaccgctttc   2280
gtgcttcctt tcgggctgat gctcggctgc tacagcgtga cgctggcacg gctgcggggc   2340
gcccgctggg gctccgggcg gcacggggcg cgggtgggcc ggctggtgag cgccatcgtg   2400
cttgccttcg gcttgctctg ggccccctac cacgcagtca accttctgca ggcggtcgca   2460
gcgctggctc caccggaagg ggccttggcg aagctgggcg gagccggcca ggcggcgcga   2520
gcgggaacta cggccttggc cttcttcagt tctagcgtca accggtgct ctacgtcttc   2580
accgctggag atctgctgcc ccgggcaggt ccccgttccc tcacgcggct cttcgaaggc   2640
tctggggagg cccgagggggg cggccgctct agggaaggga ccatggagct ccgaactacc   2700
cctcagctga aagtggtggg gcagggccgc ggcaatggag accggggggg tgggatggag   2760
aaggacggtc cggaatggga cctttgacag cagaccct                          2798
```

<210> SEQ ID NO 2
<211> LENGTH: 1170
<212> TYPE: DNA

```
<213> ORGANISM: homo sapiens
<220> FEATURE:
<221> NAME/KEY: CDS
<222> LOCATION: (1)..(1167)

<400> SEQUENCE: 2 atg gca cct tct cat cgg gca tca cag gtg ggg ttt tgc ccc acc cct      48
Met Ala Pro Ser His Arg Ala Ser Gln Val Gly Phe Cys Pro Thr Pro
 1               5                  10                  15 gaa cgc cct ctg tgg cgc ctt cca ccc acc tgt agg ccc aga agg atg      96
Glu Arg Pro Leu Trp Arg Leu Pro Pro Thr Cys Arg Pro Arg Arg Met
             20                  25                  30 tcg gtc tgc tac cgt ccc cca ggg aac gag aca ctg ctg agc tgg aag     144
Ser Val Cys Tyr Arg Pro Pro Gly Asn Glu Thr Leu Leu Ser Trp Lys
         35                  40                  45 act tcg cgg gcc aca ggc aca gcc ttc ctg ctg ctg gcg gcg ctg ctg     192
Thr Ser Arg Ala Thr Gly Thr Ala Phe Leu Leu Leu Ala Ala Leu Leu
     50                  55                  60 ggg ctg cct ggc aac ggc ttc gtg gtg tgg agc ttg gcg ggc tgg cgg     240
Gly Leu Pro Gly Asn Gly Phe Val Val Trp Ser Leu Ala Gly Trp Arg
 65                  70                  75                  80 cct gca cgg ggg cga ccg ctg gcg gcc acg ctt gtg ctg cac ctg gcg     288
Pro Ala Arg Gly Arg Pro Leu Ala Ala Thr Leu Val Leu His Leu Ala
                 85                  90                  95 ctg gcc gac ggc gcg gtg ctg ctc acg ccg ctc ttt gtg gcc ttc         336
Leu Ala Asp Gly Ala Val Leu Leu Thr Pro Leu Phe Val Ala Phe
            100                 105                 110 ctg acc cgg cag gcc tgg ccg ctg ggc cag gcg ggc tgc aag gcg gtg     384
Leu Thr Arg Gln Ala Trp Pro Leu Gly Gln Ala Gly Cys Lys Ala Val
        115                 120                 125 tac tac gtg tgc gcg ctc agc atg tac gcc agc gtg ctg ctc acc ggc     432
Tyr Tyr Val Cys Ala Leu Ser Met Tyr Ala Ser Val Leu Leu Thr Gly
    130                 135                 140 ctg ctc agc ctg cag cgc tgc ctc gca gtc acc cgc ccc ttc ctg gcg     480
Leu Leu Ser Leu Gln Arg Cys Leu Ala Val Thr Arg Pro Phe Leu Ala
145                 150                 155                 160 cct cgg ctg cgc agc ccg gcc ctg gcc cgc cgc ctg ctg ctg gcg gtc     528
Pro Arg Leu Arg Ser Pro Ala Leu Ala Arg Arg Leu Leu Leu Ala Val
                165                 170                 175 tgg ctg gcc gcc ctg ttg ctc gcc gtc ccg gcc gcc gtc tac cgc cac     576
Trp Leu Ala Ala Leu Leu Leu Ala Val Pro Ala Ala Val Tyr Arg His
            180                 185                 190 ctg tgg agg gac cgc gta tgc cag ctg tgc cac ccg tcg ccg gtc cac     624
Leu Trp Arg Asp Arg Val Cys Gln Leu Cys His Pro Ser Pro Val His
        195                 200                 205 gcc gcc gcc cac ctg agc ctg gag act ctg acc gct ttc gtg ctt cct     672
Ala Ala Ala His Leu Ser Leu Glu Thr Leu Thr Ala Phe Val Leu Pro
    210                 215                 220 ttc ggg ctg atg ctc ggc tgc tac agc gtg acg ctg gca cgg ctg cgg     720
Phe Gly Leu Met Leu Gly Cys Tyr Ser Val Thr Leu Ala Arg Leu Arg
225                 230                 235                 240 ggc gcc cgc tgg ggc tcc ggg cgg cac ggg gcg cgg gtg ggc cgg ctg     768
Gly Ala Arg Trp Gly Ser Gly Arg His Gly Ala Arg Val Gly Arg Leu
                245                 250                 255 gtg agc gcc atc gtg ctt gcc ttc ggc ttg ctc tgg gcc ccc tac cac     816
Val Ser Ala Ile Val Leu Ala Phe Gly Leu Leu Trp Ala Pro Tyr His
            260                 265                 270 gca gtc aac ctt ctg cag gcg gtc gcg ctg gct cca ccg gaa ggg         864
Ala Val Asn Leu Leu Gln Ala Val Ala Leu Ala Pro Pro Glu Gly
        275                 280                 285 gcc ttg gcg aag ctg ggc gga gcc ggc cag gcg gcg cga gcg gga act     912
```

```
                Ala Leu Ala Lys Leu Gly Gly Ala Gly Gln Ala Ala Arg Ala Gly Thr
                    290                 295                 300 acg gcc ttg gcc ttc ttc agt tct agc gtc aac ccg gtg ctc tac gtc      960
Thr Ala Leu Ala Phe Phe Ser Ser Ser Val Asn Pro Val Leu Tyr Val
305                 310                 315                 320 ttc acc gct gga gat ctg ctg ccc cgg gca ggt ccc cgt ttc ctc acg     1008
Phe Thr Ala Gly Asp Leu Leu Pro Arg Ala Gly Pro Arg Phe Leu Thr
                    325                 330                 335 cgg ctc ttc gaa ggc tct ggg gag gcc cga ggg ggc ggc cgc tct agg     1056
Arg Leu Phe Glu Gly Ser Gly Glu Ala Arg Gly Gly Gly Arg Ser Arg
                340                 345                 350 gaa ggg acc atg gag ctc cga act acc cct cag ctg aaa gtg gtg ggg     1104
Glu Gly Thr Met Glu Leu Arg Thr Thr Pro Gln Leu Lys Val Val Gly
            355                 360                 365 cag ggc cgc ggc aat gga gac ccg ggg ggt ggg atg gag aag gac ggt     1152
Gln Gly Arg Gly Asn Gly Asp Pro Gly Gly Gly Met Glu Lys Asp Gly
370                 375                 380 ccg gaa tgg gac ctt tga                                             1170
Pro Glu Trp Asp Leu
385

<210> SEQ ID NO 3
<211> LENGTH: 389
<212> TYPE: PRT
<213> ORGANISM: homo sapiens

<400> SEQUENCE: 3

Met Ala Pro Ser His Arg Ala Ser Gln Val Gly Phe Cys Pro Thr Pro
1               5                   10                  15

Glu Arg Pro Leu Trp Arg Leu Pro Pro Thr Cys Arg Pro Arg Arg Met
            20                  25                  30

Ser Val Cys Tyr Arg Pro Pro Gly Asn Glu Thr Leu Leu Ser Trp Lys
        35                  40                  45

Thr Ser Arg Ala Thr Gly Thr Ala Phe Leu Leu Ala Ala Leu Leu
    50                  55                  60

Gly Leu Pro Gly Asn Gly Phe Val Val Trp Ser Leu Ala Gly Trp Arg
65                  70                  75                  80

Pro Ala Arg Gly Arg Pro Leu Ala Ala Thr Leu Val Leu His Leu Ala
                85                  90                  95

Leu Ala Asp Gly Ala Val Leu Leu Thr Pro Leu Phe Val Ala Phe
            100                 105                 110

Leu Thr Arg Gln Ala Trp Pro Leu Gly Gln Ala Gly Cys Lys Ala Val
        115                 120                 125

Tyr Tyr Val Cys Ala Leu Ser Met Tyr Ala Ser Val Leu Leu Thr Gly
    130                 135                 140

Leu Leu Ser Leu Gln Arg Cys Leu Ala Val Thr Arg Pro Phe Leu Ala
145                 150                 155                 160

Pro Arg Leu Arg Ser Pro Ala Leu Ala Arg Arg Leu Leu Ala Val
                165                 170                 175

Trp Leu Ala Ala Leu Leu Leu Ala Val Pro Ala Ala Val Tyr Arg His
            180                 185                 190

Leu Trp Arg Asp Arg Val Cys Gln Leu Cys His Pro Ser Pro Val His
        195                 200                 205

Ala Ala Ala His Leu Ser Leu Glu Thr Leu Thr Ala Phe Val Leu Pro
    210                 215                 220

Phe Gly Leu Met Leu Gly Cys Tyr Ser Val Thr Leu Ala Arg Leu Arg
225                 230                 235                 240
```

-continued

```
Gly Ala Arg Trp Gly Ser Gly Arg His Gly Ala Arg Val Gly Arg Leu
            245                 250                 255

Val Ser Ala Ile Val Leu Ala Phe Gly Leu Leu Trp Ala Pro Tyr His
        260                 265                 270

Ala Val Asn Leu Leu Gln Ala Val Ala Leu Ala Pro Pro Glu Gly
    275                 280                 285

Ala Leu Ala Lys Leu Gly Gly Ala Gln Ala Arg Ala Gly Thr
    290                 295                 300

Thr Ala Leu Ala Phe Phe Ser Ser Val Asn Pro Val Leu Tyr Val
305                 310                 315                 320

Phe Thr Ala Gly Asp Leu Leu Pro Arg Ala Gly Pro Arg Phe Leu Thr
                325                 330                 335

Arg Leu Phe Glu Gly Ser Gly Glu Ala Arg Gly Gly Arg Ser Arg
            340                 345                 350

Glu Gly Thr Met Glu Leu Arg Thr Thr Pro Gln Leu Lys Val Val Gly
                355                 360                 365

Gln Gly Arg Gly Asn Gly Asp Pro Gly Gly Met Glu Lys Asp Gly
        370                 375                 380

Pro Glu Trp Asp Leu
385
```

```
<210> SEQ ID NO 4
<211> LENGTH: 1077
<212> TYPE: DNA
<213> ORGANISM: homo sapiens
<220> FEATURE:
<221> NAME/KEY: CDS
<222> LOCATION: (1)..(1074)

<400> SEQUENCE: 4 atg tcg gtc tgc tac cgt ccc cca ggg aac gag aca ctg ctg agc tgg        48
Met Ser Val Cys Tyr Arg Pro Pro Gly Asn Glu Thr Leu Leu Ser Trp
 1               5                  10                  15 aag act tcg cgg gcc aca ggc aca gcc ttc ctg ctg ctg gcg gcg ctg        96
Lys Thr Ser Arg Ala Thr Gly Thr Ala Phe Leu Leu Leu Ala Ala Leu
             20                  25                  30 ctg ggg ctg cct ggc aac ggc ttc gtg gtg tgg agc ttg gcg ggc tgg       144
Leu Gly Leu Pro Gly Asn Gly Phe Val Val Trp Ser Leu Ala Gly Trp
         35                  40                  45 cgg cct gca cgg ggg cga ccg ctg gcg gcc acg ctt gtg ctg cac ctg       192
Arg Pro Ala Arg Gly Arg Pro Leu Ala Ala Thr Leu Val Leu His Leu
     50                  55                  60 gcg ctg gcc gac ggc gcg gtg ctg ctc acg ccg ctc ttt gtg gcc              240
Ala Leu Ala Asp Gly Ala Val Leu Leu Leu Thr Pro Leu Phe Val Ala
 65                  70                  75                  80 ttc ctg acc cgg cag gcc tgg ccg ctg ggc cag gcg ggc tgc aag gcg       288
Phe Leu Thr Arg Gln Ala Trp Pro Leu Gly Gln Ala Gly Cys Lys Ala
                 85                  90                  95 gtg tac tac gtg tgc gcg ctc agc atg tac gcc agc gtg ctg ctc acc       336
Val Tyr Tyr Val Cys Ala Leu Ser Met Tyr Ala Ser Val Leu Leu Thr
            100                 105                 110 ggc ctg ctc agc ctg cag cgc tgc ctc gca gtc acc cgc ccc ttc ctg       384
Gly Leu Leu Ser Leu Gln Arg Cys Leu Ala Val Thr Arg Pro Phe Leu
        115                 120                 125 gcg cct cgg ctg cgc agc ccg gcc ctg gcc cgc ctg ctg ctg gcg            432
Ala Pro Arg Leu Arg Ser Pro Ala Leu Ala Arg Leu Leu Leu Ala
    130                 135                 140 gtc tgg ctg gcc gcc ctg ttg ctc gcc gtc ccg gcc gcc gtc tac cgc       480
Val Trp Leu Ala Ala Leu Leu Leu Ala Val Pro Ala Ala Val Tyr Arg
145                 150                 155                 160
```

| | |
|---|---|
| cac ctg tgg agg gac cgc gta tgc cag ctg tgc cac ccg tcg ccg gtc<br>His Leu Trp Arg Asp Arg Val Cys Gln Leu Cys His Pro Ser Pro Val<br>               165                    170                  175 | 528 |
| cac gcc gcc gcc cac ctg agc ctg gag act ctg acc gct ttc gtg ctt<br>His Ala Ala Ala His Leu Ser Leu Glu Thr Leu Thr Ala Phe Val Leu<br>  180                        185                    190 | 576 |
| cct ttc ggg ctg atg ctc ggc tgc tac agc gtg acg ctg gca cgg ctg<br>Pro Phe Gly Leu Met Leu Gly Cys Tyr Ser Val Thr Leu Ala Arg Leu<br>             195                    200                  205 | 624 |
| cgg ggc gcc cgc tgg ggc tcc ggg cgg cac ggg gcg cgg gtg ggc cgg<br>Arg Gly Ala Arg Trp Gly Ser Gly Arg His Gly Ala Arg Val Gly Arg<br>210                    215                    220 | 672 |
| ctg gtg agc gcc atc gtg ctt gcc ttc ggc ttg ctc tgg gcc ccc tac<br>Leu Val Ser Ala Ile Val Leu Ala Phe Gly Leu Leu Trp Ala Pro Tyr<br>225                    230                    235                  240 | 720 |
| cac gca gtc aac ctt ctg cag gcg gtc gca gcg ctg gct cca ccg gaa<br>His Ala Val Asn Leu Leu Gln Ala Val Ala Ala Leu Ala Pro Pro Glu<br>             245                    250                  255 | 768 |
| ggg gcc ttg gcg aag ctg ggc gga gcc ggc cag gcg gcg cga gcg gga<br>Gly Ala Leu Ala Lys Leu Gly Gly Ala Gly Gln Ala Ala Arg Ala Gly<br>  260                        265                    270 | 816 |
| act acg gcc ttg gcc ttc ttc agt tct agc gtc aac ccg gtg ctc tac<br>Thr Thr Ala Leu Ala Phe Phe Ser Ser Ser Val Asn Pro Val Leu Tyr<br>         275                    280                  285 | 864 |
| gtc ttc acc gct gga gat ctg ctg ccc cgg gca ggt ccc cgt ttc ctc<br>Val Phe Thr Ala Gly Asp Leu Leu Pro Arg Ala Gly Pro Arg Phe Leu<br>  290                        295                    300 | 912 |
| acg cgg ctc ttc gaa ggc tct ggg gag gcc cga ggg ggc ggc cgc tct<br>Thr Arg Leu Phe Glu Gly Ser Gly Glu Ala Arg Gly Gly Gly Arg Ser<br>305                    310                    315                  320 | 960 |
| agg gaa ggg acc atg gag ctc cga act acc cct cag ctg aaa gtg gtg<br>Arg Glu Gly Thr Met Glu Leu Arg Thr Thr Pro Gln Leu Lys Val Val<br>             325                    330                  335 | 1008 |
| ggg cag ggc cgc ggc aat gga gac ccg ggg ggt ggg atg gag aag gac<br>Gly Gln Gly Arg Gly Asn Gly Asp Pro Gly Gly Gly Met Glu Lys Asp<br>  340                        345                    350 | 1056 |
| ggt ccg gaa tgg gac ctt    tga<br>Gly Pro Glu Trp Asp Leu<br>         355 | 1077 |

<210> SEQ ID NO 5
<211> LENGTH: 358
<212> TYPE: PRT
<213> ORGANISM: homo sapiens

<400> SEQUENCE: 5

Met Ser Val Cys Tyr Arg Pro Pro Gly Asn Glu Thr Leu Leu Ser Trp
 1               5                  10                  15

Lys Thr Ser Arg Ala Thr Gly Thr Ala Phe Leu Leu Leu Ala Ala Leu
            20                  25                  30

Leu Gly Leu Pro Gly Asn Gly Phe Val Val Trp Ser Leu Ala Gly Trp
        35                  40                  45

Arg Pro Ala Arg Gly Arg Pro Leu Ala Ala Thr Leu Val Leu His Leu
    50                  55                  60

Ala Leu Ala Asp Gly Ala Val Leu Leu Leu Thr Pro Leu Phe Val Ala
65                  70                  75                  80

Phe Leu Thr Arg Gln Ala Trp Pro Leu Gly Gln Ala Gly Cys Lys Ala
                85                  90                  95

Val Tyr Tyr Val Cys Ala Leu Ser Met Tyr Ala Ser Val Leu Leu Thr

```
                    100                 105                 110
Gly Leu Leu Ser Leu Gln Arg Cys Leu Ala Val Thr Arg Pro Phe Leu
        115                 120                 125

Ala Pro Arg Leu Arg Ser Pro Ala Leu Ala Arg Arg Leu Leu Leu Ala
    130                 135                 140

Val Trp Leu Ala Ala Leu Leu Ala Val Pro Ala Ala Val Tyr Arg
145                 150                 155                 160

His Leu Trp Arg Asp Arg Val Cys Gln Leu Cys His Pro Ser Pro Val
                165                 170                 175

His Ala Ala His Leu Ser Leu Glu Thr Leu Thr Ala Phe Val Leu
        180                 185                 190

Pro Phe Gly Leu Met Leu Gly Cys Tyr Ser Val Thr Leu Ala Arg Leu
        195                 200                 205

Arg Gly Ala Arg Trp Gly Ser Gly Arg His Gly Ala Arg Val Gly Arg
        210                 215                 220

Leu Val Ser Ala Ile Val Leu Ala Phe Gly Leu Leu Trp Ala Pro Tyr
225                 230                 235                 240

His Ala Val Asn Leu Leu Gln Ala Val Ala Ala Leu Ala Pro Pro Glu
                245                 250                 255

Gly Ala Leu Ala Lys Leu Gly Gly Ala Gly Gln Ala Ala Arg Ala Gly
            260                 265                 270

Thr Thr Ala Leu Ala Phe Phe Ser Ser Val Asn Pro Val Leu Tyr
        275                 280                 285

Val Phe Thr Ala Gly Asp Leu Leu Pro Arg Ala Gly Pro Arg Phe Leu
        290                 295                 300

Thr Arg Leu Phe Glu Gly Ser Gly Glu Ala Arg Gly Gly Arg Ser
305                 310                 315                 320

Arg Glu Gly Thr Met Glu Leu Arg Thr Thr Pro Gln Leu Lys Val Val
                325                 330                 335

Gly Gln Gly Arg Gly Asn Gly Asp Pro Gly Gly Met Glu Lys Asp
            340                 345                 350

Gly Pro Glu Trp Asp Leu
        355

<210> SEQ ID NO 6
<211> LENGTH: 15
<212> TYPE: DNA
<213> ORGANISM: Artificial Sequence
<220> FEATURE:
<223> OTHER INFORMATION: hBLT2 anti-sense sequence

<400> SEQUENCE: 6
cagcagtgtc tcgtt                                                     15

<210> SEQ ID NO 7
<211> LENGTH: 21
<212> TYPE: RNA
<213> ORGANISM: Artificial Sequence
<220> FEATURE:
<223> OTHER INFORMATION: hBLT2 siRNA sense sequence

<400> SEQUENCE: 7
gaaggauguc ggucugcuau u                                              21

<210> SEQ ID NO 8
<211> LENGTH: 21
<212> TYPE: RNA
<213> ORGANISM: Artificial Sequence
<220> FEATURE:
```

-continued

<223> OTHER INFORMATION: hBLT2 siRNA antisense sequence

<400> SEQUENCE: 8
uagcagaccg acauccuucu u                                             21

<210> SEQ ID NO 9
<211> LENGTH: 25
<212> TYPE: DNA
<213> ORGANISM: Artificial Sequence
<220> FEATURE:
<223> OTHER INFORMATION: forward primer for hBLT2

<400> SEQUENCE: 9
agcctggaga ctctgaccgc tttcg                                         25

<210> SEQ ID NO 10
<211> LENGTH: 25
<212> TYPE: DNA
<213> ORGANISM: Artificial Sequence
<220> FEATURE:
<223> OTHER INFORMATION: reverse primer for hBLT2

<400> SEQUENCE: 10
gacgtagagc accgggttga cgcta                                         25

<210> SEQ ID NO 11
<211> LENGTH: 20
<212> TYPE: DNA
<213> ORGANISM: Artificial Sequence
<220> FEATURE:
<223> OTHER INFORMATION: forward primer for re-hBLT2

<400> SEQUENCE: 11
tctcatcggg catcacaggt                                               20

<210> SEQ ID NO 12
<211> LENGTH: 20
<212> TYPE: DNA
<213> ORGANISM: Artificial Sequence
<220> FEATURE:
<223> OTHER INFORMATION: reverse primer for re-hBLT2

<400> SEQUENCE: 12
ccaagctcca caccacgaag                                               20

<210> SEQ ID NO 13
<211> LENGTH: 26
<212> TYPE: DNA
<213> ORGANISM: Artificial Sequence
<220> FEATURE:
<223> OTHER INFORMATION: forward primer for hBLT1

<400> SEQUENCE: 13
tatgtctgcg gagtcagcat gtacgc                                        26

<210> SEQ ID NO 14
<211> LENGTH: 24
<212> TYPE: DNA
<213> ORGANISM: Artificial Sequence
<220> FEATURE:
<223> OTHER INFORMATION: reverse primer for hBLT1

<400> SEQUENCE: 14
cctgtagccg acgccctatg tccg                                          24

<210> SEQ ID NO 15

```
<211> LENGTH: 20
<212> TYPE: DNA
<213> ORGANISM: Artificial Sequence
<220> FEATURE:
<223> OTHER INFORMATION: forward primer for 18S RNA

<400> SEQUENCE: 15
ttcggaactg aggccatgat                                                        20

<210> SEQ ID NO 16
<211> LENGTH: 20
<212> TYPE: DNA
<213> ORGANISM: Artificial Sequence
<220> FEATURE:
<223> OTHER INFORMATION: reverse primer for 18S RNA

<400> SEQUENCE: 16
tttcgctctg gtccgtcttg                                                        20

<210> SEQ ID NO 17
<211> LENGTH: 20
<212> TYPE: DNA
<213> ORGANISM: Artificial Sequence
<220> FEATURE:
<223> OTHER INFORMATION: forward primer for hBLT2 transgenic mouse

<400> SEQUENCE: 17
gcgcagggac ttcctttgtc                                                        20

<210> SEQ ID NO 18
<211> LENGTH: 21
<212> TYPE: DNA
<213> ORGANISM: Artificial Sequence
<220> FEATURE:
<223> OTHER INFORMATION: forward primer for hBLT2 transgenic mouse

<400> SEQUENCE: 18
gctctagagc ctctgctaac c                                                      21

<210> SEQ ID NO 19
<211> LENGTH: 21
<212> TYPE: DNA
<213> ORGANISM: Artificial Sequence
<220> FEATURE:
<223> OTHER INFORMATION: reverse primer for hBLT2 transgenic mouse

<400> SEQUENCE: 19
ccgatgggtg gcacaattga c                                                      21

<210> SEQ ID NO 20
<211> LENGTH: 20
<212> TYPE: DNA
<213> ORGANISM: Artificial Sequence
<220> FEATURE:
<223> OTHER INFORMATION: forward primer for mouse BLT2

<400> SEQUENCE: 20
cagcatgtac gccagcgtgc                                                        20

<210> SEQ ID NO 21
<211> LENGTH: 19
<212> TYPE: DNA
<213> ORGANISM: Artificial Sequence
<220> FEATURE:
<223> OTHER INFORMATION: reverse primer for mouse BLT2

<400> SEQUENCE: 21
```

```
cgatggcgct caccagacc                                                  19
```

<210> SEQ ID NO 22
<211> LENGTH: 19
<212> TYPE: DNA
<213> ORGANISM: Artificial Sequence
<220> FEATURE:
<223> OTHER INFORMATION: hBLT2 siRNA target sequence

<400> SEQUENCE: 22

```
gaaggatgtc ggtctgcta                                                  19
```

<210> SEQ ID NO 23
<211> LENGTH: 20
<212> TYPE: DNA
<213> ORGANISM: Artificial Sequence
<220> FEATURE:
<223> OTHER INFORMATION: forward primer for hBLT2 coding region fragment

<400> SEQUENCE: 23

```
cttctcatcg ggcatcacag                                                 20
```

<210> SEQ ID NO 24
<211> LENGTH: 20
<212> TYPE: DNA
<213> ORGANISM: Artificial Sequence
<220> FEATURE:
<223> OTHER INFORMATION: reverse primer for hBLT2 coding region fragment

<400> SEQUENCE: 24

```
atccttctgg gcctacaggt                                                 20
```

<210> SEQ ID NO 25
<211> LENGTH: 23
<212> TYPE: DNA
<213> ORGANISM: Artificial Sequence
<220> FEATURE:
<223> OTHER INFORMATION: forward primer for NOX4

<400> SEQUENCE: 25

```
ctcagcggaa tcaatcagct gtg                                             23
```

<210> SEQ ID NO 26
<211> LENGTH: 25
<212> TYPE: DNA
<213> ORGANISM: Artificial Sequence
<220> FEATURE:
<223> OTHER INFORMATION: reverse primer for NOX4

<400> SEQUENCE: 26

```
agaggaacac gacaatcagc cttag                                           25
```

<210> SEQ ID NO 27
<211> LENGTH: 20
<212> TYPE: DNA
<213> ORGANISM: Artificial Sequence
<220> FEATURE:
<223> OTHER INFORMATION: forward primer for MMP-2

<400> SEQUENCE: 27

```
gctcagatcc gtggtgagat                                                 20
```

<210> SEQ ID NO 28
<211> LENGTH: 20
<212> TYPE: DNA
<213> ORGANISM: Artificial Sequence
<220> FEATURE:

```
<223> OTHER INFORMATION: reverse primer for MMP-2

<400> SEQUENCE: 28
ggtgctggct gagtagatcc                                                  20

<210> SEQ ID NO 29
<211> LENGTH: 21
<212> TYPE: DNA
<213> ORGANISM: Artificial Sequence
<220> FEATURE:
<223> OTHER INFORMATION: forward primer for GADPH

<400> SEQUENCE: 29
ctgcaccacc aactgcttag c                                                21

<210> SEQ ID NO 30
<211> LENGTH: 21
<212> TYPE: DNA
<213> ORGANISM: Artificial Sequence
<220> FEATURE:
<223> OTHER INFORMATION: reverse primer for GADPH

<400> SEQUENCE: 30
cttcaccacc ttcttgatgt c                                                21
```